US009943564B2

(12) United States Patent
Van Der Weerden et al.

(10) Patent No.: US 9,943,564 B2
(45) Date of Patent: Apr. 17, 2018

(54) ANTI-PATHOGENIC METHODS
(71) Applicant: Hexima Limited, La Trobe University, Victoria (AU)
(72) Inventors: Nicole Van Der Weerden, Coburg (AU); Marilyn Anne Anderson, Keilor (AU)
(73) Assignee: Hexima Limited, Victoria (AU)
( * ) Notice: Subject to any disclaimer, the term of this patent is extended or adjusted under 35 U.S.C. 154(b) by 0 days. days.
(21) Appl. No.: 14/646,579
(22) PCT Filed: Nov. 22, 2013
(86) PCT No.: PCT/AU2013/001346
§ 371 (c)(1),
(2) Date: May 21, 2015
(87) PCT Pub. No.: WO2014/078900
PCT Pub. Date: May 30, 2014

(65) Prior Publication Data
US 2015/0283204 A1 Oct. 8, 2015

Related U.S. Application Data
(60) Provisional application No. 61/729,467, filed on Nov. 23, 2012.

(51) Int. Cl.
A01N 65/38 (2009.01)
A01N 65/08 (2009.01)
C12N 15/82 (2006.01)
A01N 65/44 (2009.01)
A01N 65/12 (2009.01)
A01N 65/28 (2009.01)
A01N 65/40 (2009.01)
C07K 14/415 (2006.01)
A61K 9/00 (2006.01)
A01N 65/20 (2009.01)
A61K 38/16 (2006.01)
A01N 37/46 (2006.01)
A01N 65/00 (2009.01)
A61K 45/06 (2006.01)

(52) U.S. Cl.
CPC ............ A61K 38/168 (2013.01); A01N 37/46 (2013.01); A01N 65/00 (2013.01); A01N 65/08 (2013.01); A01N 65/12 (2013.01); A01N 65/20 (2013.01); A01N 65/28 (2013.01); A01N 65/38 (2013.01); A01N 65/385 (2013.01); A01N 65/40 (2013.01); A01N 65/44 (2013.01); A61K 9/0014 (2013.01); A61K 45/06 (2013.01); C07K 14/415 (2013.01); C12N 15/8279 (2013.01); C12N 15/8282 (2013.01); C12N 15/8286 (2013.01)

(58) Field of Classification Search
None
See application file for complete search history.

(56) References Cited

U.S. PATENT DOCUMENTS 6,512,166 B1 1/2003 Harman et al.
6,605,698 B1 * 8/2003 Van Amerongen .... A01N 65/08
435/252.3
7,041,877 B2 5/2006 Anderson et al.
7,297,840 B2 11/2007 Anderson et al.
7,544,861 B2 6/2009 Anderson et al.
8,252,898 B2 8/2012 Anderson et al.
8,722,968 B2 5/2014 Anderson et al.
2003/0217382 A1 11/2003 Anderson et al.
2005/0150004 A1 7/2005 Anderson et al.
2006/0150276 A1 7/2006 Anderson et al.
2006/0156433 A1 7/2006 Anderson et al.
2007/0277263 A1 11/2007 Anderson et al.
2008/0109924 A1 5/2008 Ali et al.
2009/0069545 A1 3/2009 Anderson et al.
2010/0095408 A1 4/2010 Heath et al.
2010/0104552 A1 4/2010 Mygind et al.
2010/0218280 A1 8/2010 Anderson et al.
2013/0047299 A1 2/2013 Anderson et al.
2013/0263326 A1 10/2013 Heath et al.
2013/0267459 A1 10/2013 Heath et al.
2013/0269059 A1 10/2013 Heath et al.
2014/0130209 A1 5/2014 Van Der Weerden et al.
2014/0208461 A1 7/2014 Anderson et al.
2015/0067917 A1 3/2015 Heath et al.

FOREIGN PATENT DOCUMENTS

WO 2003000863 1/2003
WO 2005018701 3/2005
WO 2005094579 10/2005
WO 2008128289 10/2008
(Continued)

OTHER PUBLICATIONS

Dictionary.com (accessed Jun. 24, 2016).*
Stotz et al. ("Plant Defensins"; Plant Signal Behav. Nov. 2009; 4(11):1010-1012).*
HPSC (accessed Jun. 2, 2016).*
Olsen et al. "Fungal Diseases: An emerging threat to human, animal and plant health" The National Academies Press. 2011.*
American Diabetes Association (accessed Feb. 2, 2017).*
George, John T et al. "Host-anti-microbial response to Helicobacter pylori infection" Molecular Immunology (2003), 40(7), 451-456, XP002755710—Abstract.
Lehrer, Robert I et al. "Synergistic activity of rabbit granulocyte peptides against Candida albicans" Infection and Immunity (1986), 52(3), 902-4, XP002755709—Abstract.
Levy, Ofer et al. "Individual and synergistic effects of rabbit granulocyte proteins on Escherichia coli" Journal of Clinical Investigation (1994), 94(2), 672-82, XP002755706—Abstract.
Lichtenstein, Alan K et al. "Synergistic cytolysis mediated by hydrogen peroxide combined with peptide defensins" Cellular Immunology (1988), 114(1), 104-16, XP002755707—Abstract.
Lichtenstein, Alan et al. "In vitro tumor cell cytolysis mediated by peptide defensins of human and rabbit granuloyctes" Blood (1986), 68(6), 1407-10, XP002755708—Abstract.
(Continued)

Primary Examiner — James H Alstrum-Acevedo
Assistant Examiner — Tara L Martinez
(74) Attorney, Agent, or Firm — Knobbe Martens Olson & Bear LLP

(57) ABSTRACT

The present disclosure teaches the protection of plants and human and non-human subjects from pathogens. The present disclosure enables a multivalent approach to inhibiting pathogen infection in plant and human and non-human animal subjects and to ameliorate damage to susceptible subjects.

13 Claims, 2 Drawing Sheets

(56) References Cited

FOREIGN PATENT DOCUMENTS

| | | |
|---|---|---|
| WO | 2007137329 | 1/2009 |
| WO | 2009094719 | 8/2009 |
| WO | 2010015024 | 2/2010 |
| WO | 2012106759 | 8/2012 |

OTHER PUBLICATIONS

Phattarataratip E et al. "*Streptococcus mutans* strains recovered from caries-active or caries-free individuals differ in sensitivity to host antimicrobial peptides" Molecular Oral Microbiology (2011) 26:187-199.

Wu, Minhao et al. ".beta.—Defensins 2 and 3 Together Promote Resistance to Pseudomonas aeruginosa Keratitis" Journal of Immunology (2009), 183(12), 8054-8060, XP002755705—Abstract.

Yanagi, S et al. "Significance of human .beta.—defensins in the epithelial lining fluid of patients with chronic lower respiratory tract infections" Clinical Microbiology and Infection (2007), 13(1), 63-69, XP002755711—Abstract.

Non-Final Office Action issued for U.S. Appl. No. 13/983,941, dated Mar. 2, 2016, 17 pages.

Almeida et al., "Characterization of Two Novel Defense Peptides from Pea (*Pisum sativum*) Seeds" Arch Biochem Biophys 378:278-286, 2000.

Balandin et al. (2005) "A protective role for the embryo surrounding region of the maize endosperm, as evidenced by the characterisation of ZmESR-6, a defensin gene specifically expressed in this region," Plant. Mol. Biol. 58:269-282.

Chen et al. (2005) "Cloning and Characterization of a Plant Defensin VaD1 from Azuki Bean," J. Agric. Food Chem. 53:982-988.

EMBL-EBI [online] (1995) "*Solanum lycopersicum* (tomato) flower-specific gamma-thionin-like protein/acidic protein precursor," Accession No. AAA80496. Accessible on the Internet at URL: http://www.ebi.ac.uk/ena/data/view/AAA80496. [Last Accessed Oct. 22, 2015].

GenBank (1995) "Defensin Dm-AMP1=cysteine-rich antimicrobial protein [*Dahlia merckii*, seeds, Peptide, 50 aa]," Accession No. AAB34972. Accessible on the Internet at URL: http://www.ncbi.nlm.nih.gov/protein/AAB34972. [Last Accessed Oct. 22, 2015].

GenBank (1995) "Defensin Hs-AFP1=cysteine-rich antifungal protein [*Heuchera sanguinea*, seeds, Peptide, 54 aa]," Accession No. AAB34974. Accessible on the Internet at URL: http://www.ncbi.nlm.nih.gov/protein/AAB34974. [Last Accessed Oct. 22, 2015].

GenBank (2005) "Defensin [*Zea mays*]," Accession No. CAH61275. Accessible on the Internet at URL: http://www.ncbi.nlm.nih.gov/protein/CAH61275. [Last Accessed Oct. 22, 2015].

GenBank (2005) "Medicago truncatula defensin (Def2.1) gene, complete cds," AY313169. Accessible on the Internet at URL: http://www.ncbi.nlm.nih.gov/nuccore/AY313169. [Last Accessed Oct. 22, 2015].

GenBank (2005) "Putative defensin 1.1 precursor [Medicago sativa]," Accession No. AAV85437. Accessible on the Internet at URL: http://www.ncbi.nlm.nih.gov/protein/AAV85437. [Last Accessed Oct. 22, 2015].

GenBank (Oct. 10, 2012) "Chain A, Nmr Solution Structure of Vigna Radiata Defensin 2 (Vrd2)," Accession No. 2GL1_A. Accessible on the Internet at URL: http://www.ncbi.nlm.nih.gov/protein/2GL1A. [Last Accessed Oct. 22, 2015].

Hanks et al. (2005) "Defensin gene family in Medicago truncatula: structure, expression and induction by signal molecules," Plant Mol. Biol. 58:385-399.

International Search Report with Written Opinion corresponding to International Patent Application No. PCT/AU2013/001346, dated Apr. 15, 2014.

International Preliminary Report on Patentability and claim amendments corresponding to International Patent Application No. PCT/AU2013/001346, completed Sep. 4, 2014.

Kushmerick et al. (1998) "Functional and structural features of γ-zeathionins, a new class of sodium channel blockers," FEBS Letters 440:302-306.

Lay et al. (2003) "The three-dimensional solution structure of NaD1, a new floral defensin from Nicotiana alata and its application to a homology model of the crop defense protein alfAFP," J. Mol. Biol. 325:175-188.

Lin et al. (2007) "Structure-based protein engineering for alpha-amylase inhibitory activity of plant defensing," Proteins. 68:530-540.

Mendez et al. (1990) "Primary structure and inhibition of protein synthesis in eukaryotic cell-free system of a novel thionin, gamma-hordothionin, from barley endosperm," Eur. J. Biochem. 194:533-539.

Milligan et al. (1995) "Nature and regulation of pistil-expressed genes in tomato," Plant Mol. Biol. 28:691-711.

Osborn et al. (1995) "Isolation and characterisation of plant defensins from seeds of *Asteraceae, Fabaceae, Hippocastanaceae* and *Saxifragaceae*," FEBS Lett. 368:257-262.

Sagaram et al. (Apr. 13, 2011) "Structure-activity determinants in antifungal plant defensins MsDef1 and MtDef4 with different modes of action against Fusarium graminearum," PLoS One 6(4):e18550.

Spelbrink et al. (2004) "Differential antifungal and calcium channel-blocking activity among structurally related plant defensins," Plant Physiol. 135:2055-2067.

Terras et al. (1992) "Analysis of two novel classes of plant antifungal proteins from radish (*Raphanus sativus* L.) seeds," J. Biol. Chem. 267:15301-15309.

UniProt [online] (1991) "Defensin-like protein 1," Accession No. P20230. Accessible on the Internet at URL: http://www.uniprot.org/uniprot/P20230. [Last Accessed Oct. 22, 2015].

UniProt [online] (1996) "Defensin-like protein 2," Accession No. P30230. Accessible on the Internet at URL: http://www.uniprot.org/uniprot/P30230. [Last Accessed Oct. 22, 2015].

UniProt [online] (1997) "Defensin-like protein 2," Accession No. P81009. Accessible on the Internet at URL: http://www.uniprot.org/uniprot/P81009. [Last Accessed Oct. 22, 2015].

UniProt [online] (2002) "Defensin-1," Accession No. P81929. Accessible on the Internet at URL: http://www.uniprot.org/uniprot/P81929. [Last Accessed Oct. 22, 2015].

UniProt [online] (2003) "Floral defensin-like protein 1," Accession No. Q8H6Q1. Accessible on the Internet at URL: http://www.uniprot.org/uniprot/Q8H6Q1. [Last Accessed Oct. 22, 2015].

UniProt [online] (2003) "Floral defensin-like protein 2," Accession No. Q8H6Q0. Accessible on the Internet at URL: http://www.uniprot.org/uniprot/Q8H6Q0. [Last Accessed Oct. 22, 2015].

UniProt [online] (2003) "Flower-specific defensing," Accession No. Q8GTM0. Accessible on the Internet at URL: http://www.uniprot.org/uniprot/Q8GTM0. [Last Accessed Oct. 22, 2015].

\* cited by examiner

ANTI-PATHOGENIC METHODS

CROSS-REFERENCE TO RELATED APPLICATIONS

This application is the U.S. National Stage of International Application No. PCT/AU2013/001346, filed Nov. 22, 2013, which claims the benefit of U.S. Provisional Patent Application No. 61/729,467, filed Nov. 23, 2012; both of which are hereby incorporated by reference to the extent not inconsistent with the disclosure herewith.

FILING DATA

This application is associated with and claims priority from U.S. Provisional Application No. 61/729,467, filed on 23 Nov. 2012, entitled "Anti-pathogenic methods", the entire contents of which, are incorporated herein by reference.

FIELD

The present disclosure teaches the protection of plants and human and non-human subjects from pathogens. The present disclosure enables a multivalent approach to inhibiting pathogen infection in plant and human and non-human animal subjects and to ameliorate damage to susceptible subjects.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Crop losses due to infection by plant pathogens (phytopathogens) such as fungal and insect pathogens are a major problem in the agricultural industry and each year, millions of dollars are spent on the application of fungicides to curb these losses (Oerke and Dehne (2004) *Crop Protection* 23:275-285). There is a need to identify new anti-phytopathogen strategies. This is particularly important given the propensity for pathogens to develop resistance. Fungal infection of human and non-human subjects can also lead to significant discomfort and major health issues. Pathogenic fungi are also a serious concern for human health and for the economy. Human fungal pathogens cause life-threatening hospital-acquired diseases with high mortality rates as well as less severe superficial infections.

Plants have evolved to produce peptides to protect against pathogens. Their specificity is likely influenced by the evolutionary in response to exposure to various pathogens.

Plant defensins represent one type of anti-pathogen molecule. There is a wide variety of defensins with differing spatial and temporal patterns of expression and spectra of activity. Generally, plant defensins are divided into two major classes. Class I defensins consist of an endoplasmic reticulum (ER) sequence followed by a mature defensin domain. Class II defensins are produced as larger precursors with C-terminal pro-domains or pro-peptides (CTPPs) of about 33 amino acids in addition to the ER signal sequence and mature domain.

The mechanism underlying the specificity of these peptides is yet to be fully elucidated, although interactions with plasma membrane components are presumed to be involved. Since membrane permeabilization is a common activity of many anti-pathogen peptides and the membrane composition of various cell types is highly variable, the presence of specific lipids is postulated in some cases to be responsible for the efficacy of anti-pathogen peptides.

Plant pathogens induce significant plant yield loss and current strategies for pathogen control are both expensive and potentially damaging to the environment. Given the need to improve the economy of agriculture production, new strategies are required for protecting agronomic and ornamentally important plants from a range of diseases, especially fungal disease. Pathogenic fungi are also a serious concern for human health and for the economy. Current therapies require long treatment regimes and patients often suffer from associated liver toxicity. Resistance to current therapies is also developing creating a need for novel therapeutics.

SUMMARY

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include singular and plural aspects unless the context clearly dictates otherwise. Thus, for example, reference to "a permeabilizing defensin" includes a single permeabilizing defensin, as well as two or more permeabilizing defensins; reference to "an agent" includes a single agent, as well as two or more agents; reference to "the invention" includes a single or multiple aspects taught by the disclosure. Aspects disclosed herein are encompassed by the term "invention". All aspects of the invention are enabled within the width of the claims.

Nucleotide and amino acid sequences are referred to by a sequence identifier number (SEQ ID NO). The SEQ ID NOs correspond numerically, to the sequence identifiers <400>1 (SEQ ID NO:1), <400>2 (SEQ ID NO:2), etc. A summary of sequence identifiers is provided in Table 1.

Disclosed herein is a method for reducing damage to crops and ornamental plants caused by pathogens such as fungal and insect agents. The traditional method of control involves application of chemical fungicides. This adds to the cost of crop and flower production. In accordance with the present disclosure, a surprising synergy is identified between a Class I defensin and a permeabilizing defensin resulting in increased efficacy in preventing and ameliorating fungal and insect disease conditions in plants. The method is also applicable to treating or preventing pathogen infestation in human and non-human animal subjects. Reference to a "Class I" defensin includes permeabilizing and non-permeabilizing defensins. Hence, one or more permeabilizing defensins may be employed. Reference to a "permeabilizing defensin" includes a Class I defensin, a Class II defensin and a variant defensin, which is a permeabilizing defensin. A "variant" defensin includes a defensin wherein a Loop 1B region from a Class II defensin is replaced by a Loop 1B region from a Class I defensin or the Class II Loop 1B region is otherwise subject to one or more amino acid substitutions, additions or deletions. The Loop 1B region is located between the first β-strand (β-strand 1) and the α-helix on the defensin N-terminal end portion (also referred to as the first flexible loop).

As indicated above, plant defensins are divided into two major classes. Class I defensins consist of an endoplasmic reticulum (ER) signal sequence followed by a mature defensin domain. Class II defensins are produced as larger precursors with C-terminal pro-domains or pro-peptides (CTPPs) of about 33 amino acids in addition to the ER signal sequence and mature domain.

Synergy is classified as the difference between the observed % fungal growth inhibition caused by the combination of two defensins (Io value) and the expected % fungal growth inhibition of the two defensins based on the sum of the % fungal growth inhibition of each defensin on its own (Ee value calculated according to the Limpel formula used by Richer et al. (1987) *Pestic Sci* 19:309-315). The difference, Io-Ee, is the synergy value. A synergy value up to 15 means no significant synergy; 15-30 is a low level of synergy; 30-60 is a medium level of synergy; and >60 is a high level of synergy.

Accordingly, the present disclosure teaches a method for protecting a plant from a disease associated with infection by a pathogen, the method comprising providing cells with a Class I plant defensin and a permeabilizing defensin or a precursor or a functional homolog, analog, derivative or variant thereof of either or both. In an embodiment, the plant pathogen is a fungus. In another embodiment, the plant pathogen is an insect. Reference to a "plant" includes in one aspect, a genetically modified plant comprising cells which produce the Class I defensin and a permeabilizing defensin wherein cells, prior to genetic modification, do not produce either defensin. Reference to a "plant" includes, progeny of the genetically modified plant which comprise cells which produce one or other or both of the defensins as a result of the genetic modification of the parent. The production of the two defensins resulting from the genetic modification of the parent and this trait passed on to the progeny confers a resistance to the fungal or insect pathogen to a level not observed in plants which do not produce both defensins. A Class I defensin may be a permeabilizing defensin or a non-permeabilizing defensin. The present disclosure further teaches a method for protecting a human or non-human animal subject from a disease associated with infection by a pathogen, the method comprising providing cells with a Class I plant defensin and a permeabilizing defensin or a precursor or a functional homolog, analog, derivative or variant thereof of either or both. In an embodiment, the pathogen is a fungus. Reference to a non-human animal subject includes a farm animal (e.g. cow, sheep, pig, horse, donkey, Llama, alpaca, avian animal), domestic animal (e.g. dogs, cat), laboratory test animal (e.g. mouse, rat, guinea pig, rabbit, hamster, non-human primate) and captured wild animal.

The term "genetic modification" means that a plant or plant cell is genetically modified by recombinant DNA technology to introduce genetic material encoding both defensins. Alternatively, this technology is used to introduce genetic material encoding at least one defensin, and conventional breeding is used to introduce another defensin gene.

In an embodiment, the Class I defensin is a permeabilizing defensin. In another embodiment, the Class I defensin is a non-permeabilizing defensin. In an embodiment, the second permeabilizing defensin is selected from a Class I, Class II or variant defensin.

The present disclosure enables a method for protecting a plant from infection by a fungal or insect pathogen and/or for reducing the incidence of severity of fungal or insect pathogen-associated disease. The instant disclosure is also useful for reducing fungal or insect infestation on the plant and/or its surrounding root system or soil to an acceptable level. The method encompasses a multivalent approach of using a combination of at least one Class I defensin and one permeabilizing defensin. An example of the latter permeabilizing defensin is a Class I, Class II or variant defensin. Variant defensins are taught in PCT/AU2012/000112, the contents of which are incorporated herein by reference. Unexpectedly, the combined action of a given Class I defensin and a given permeabilizing defensin on a given fungal or insect pathogen is synergistic, i.e. the anti-pathogen activity of the (at least) two components is greater than the sum of the inhibitory effects of either defensin acting alone when they are combined in the plant environment. The level of synergy is from low to high.

Hence, the present disclosure is instructional for a method for protecting a plant from a disease associated with infection by a fungal or insect pathogen, the method comprising providing cells of the plants with a Class I defensin and a permeabilizing defensin or a precursor or a functional homolog, analog, derivative or variant thereof of either or both in a synergistically effective amount to reduce infection by the pathogen.

Reference to a "method" in this context includes a plant management system, a protocol and a procedure. As indicated above, in an embodiment, the pathogen is a fungal pathogen. In another embodiment, the pathogen is an insect pathogen.

Reference to "providing cells of the plant" includes providing the two defensins from an exogenous source, or providing both from within the cell (via genetic modification) or providing one exogenously and one intracellularly. Hence, topical application and genetic engineering may be used and optionally further including conventional breeding to genetic plants exposed to both defensins. Further enabled herein is a topical seed coating comprising the combination of two defensins or the topical application of one defensin to a plant or plant seed engineered to express the other defensin.

Further enabled herein is a method for protecting a human or non-human animal subject from a disease associated with infection by a fungal or insect pathogen, the method comprising providing cells of the human or non-human animal with a Class I defensin and a permeabilizing defensin or a precursor or a functional homolog, analog, derivative or variant thereof of either or both in a synergistically effective amount to reduce infection by the pathogen.

The present disclosure further contemplates the use of a Class I defensin and a permeabilizing defensin or a precursor form of either or both in, the manufacture of a genetically modified plant which is less susceptible to fungal or insect infestation or exhibits less fungal or insect infestation-associated damage.

The present disclosure further contemplates the use of a Class I defensin and a permeabilizing defensin or a precursor form of either or both in the manufacture of a medicament for the treatment of a fungal infestation in a human or non-human animal subject.

In an embodiment, a method is provided for protecting crop or ornamental plants from fungal or insect challenge, comprising providing to the plant a Class I defensin and a permeabilizing defensin or functional homologs, analogs or variants or equivalents thereof. In this embodiment, the extent of fungal or insect inhibition by both components is considered synergistic compared to the combined separate effects of each component alone. In an embodiment, there is synergistic inhibition of *Fusarium* species by a combination of at least one Class I defensin, and at least one permeabilizing defensin. Examples of Class I defensins include hordothionin (γ1-H), zeathionin (γ-Zea2), PsD1, DmAMP1, SBI6, VP42, VP45, VP135, RsAFP2, MsDef1, MtDef2, MtDef4, HsAFP1, VaD2, VrD2, ZmESR6 and a HXL defensin (see Table 2). Examples of a permeabilizing defensin include NaD1, TPP3, PhD1A, PhD2, HXL001, HXL002, HXL004, HXL007, HXL008, HXP4, HXP34 and HXP35 and NoD173 (see Table 2). The subject method may also additionally include the use of a proteinase inhibitor or a precursor form thereof such as a cysteine or serine proteinase inhibitor (e.g. potato StPin1A [previously referred to as Pot1A (U.S. Pat. No. 7,462,695)]), HvCPI6, SlCys9, At2g38870, bovine pancreatic trypsin inhibitor (BPTI) or bovine trypsin inhibitor I-P. Any fungus or insect individually susceptible to inhibition by each of the components of the system can be more effectively controlled by using the combination than by either component used by itself. Particularly useful combinations include HXP4, NaD1, HXL004, HXL001 and/or HXL008 as a permeabilizing defensin and HXL012, HXL015, SB16, HXL009, HXL008 and/or HXL021 as the Class I defensin.

The instant disclosure further provides a method for protecting a plant from a disease associated with infection by a fungal or insect pathogen. The method comprises providing cells of a plant with a Class I defensin and a permeabilizing defensin and optionally a proteinase inhibitor or a precursor or a functional homolog, analog, derivative or variant thereof of any one or all of these components.

The multivalent approach of the present method comprises a Class I defensin and a permeabilizing defensin acting synergistically together or further comprising a proteinase inhibitor or a precursor form thereof. These components may be produced by recombinant means within a plant cell or may be provided to a plant cell topically such as in the form of a spray, aerosol, powder or as part of fertilizer or plant food. As indicated above, in yet another alternative, one component is provided by recombinant means and another component is provided exogenously. Topical seed coatings, are enabled herein. Both defensins may be applied to the seed coat or one defensin is topically applied to a plant or seed which has been engineered to express another defensin. In an embodiment, one or other defensin is provided by genetic engineering means and the other defensin is introduced by conventional breeding.

Another aspect taught herein is a method for inhibiting fungal or insect growth, replication, infection and/or maintenance, the method comprising exposing the fungus or insect to a combination of a Class I defensin and a permeabilizing defensin. A proteinase inhibitor or precursor form thereof may also be used. This applies to plants and human and non-human animal subjects.

Again, the extent of fungal or insect inhibition in the presence of both defensins is synergistic as compared to the sum of inhibition provided by either component in individual contact with the fungus at the same dose used for the combined exposure.

A fungus or an insect is "susceptible to inhibition" by each of the individual components of the system if it can be shown that each component individually exerts an inhibitory activity against the fungus or insect, or the components in combination exert a combined inhibitory effect that is synergistic.

Chimeric defensin molecules and/or defensin variants which retain anti-fungal activity can also be employed in the present method for plant protection based on whether the chimeric defensin is regarded as a Class I defensin or a permeabilizing defensin or both.

Further enabled herein is a multigene expression vehicle (MGEV) comprising a polynucleotide having 2 to 8 domain segments, each domain encoding a functional protein wherein at least one domain encodes a Class I defensin and at least one other domain encodes a permeabilizing defensin, each domain being joined to the next in a linear sequence by a linker sequence encoding a linker peptide having the amino acid sequence set forth in SEQ ID NO:86. The MGEV vector is disclosed in USSN 2007-0277263, the contents of which are incorporated herein by reference.

In an embodiment, at least one other domain encodes a proteinase inhibitor or a precursor form thereof.

The linker peptide comprises the amino acid sequence $X_1X_2X_3X_4X_5$ (SEQ ID NO:86) wherein:
$X_1$=E or D
$X_2$=E or D
$X_3$=K or R
$X_4$=K or R
$X_5$=N or Q.

The present disclosure further teaches the use of a Class I defensin and a permeabilizing defensin and optionally a proteinase inhibitor or a functional homolog, analog, derivative or variant thereof of any one or all of these components in the manufacture of a genetically modified plant or its progeny resistant to fungal or insect pathogen infestation.

The present disclosure further teaches the use of a Class I defensin and a permeabilizing defensin and optionally a proteinase inhibitor or a functional homolog, analog, derivative or variant thereof of any one or all of these components in a human or non-human animal subject or its progeny resistant to fungal or insect pathogen infestation.

Proteinase inhibitors useful in embodiments of the present method include but are not limited to cysteine and serine proteinase inhibitors.

Plants which can be protected from fungal or insect infestation by the instant method include those which are susceptible to a fungus or insect which is sensitive to a proteinase inhibitor and a plant defensin which can be expressed as transgenes in that plant or to which a composition comprising the defensin and proteinase inhibitor, can be applied.

A combined transgene and topical application approach is also contemplated herein. A "topical application approach" includes seed coatings. The proteinase inhibitor is generally a protein or a peptide or a chemical analog thereof. The plant can be a monocotyledonous plant or dicotyledonous plant. Particular plants include corn (maize), soybean, cotton, canola and wheat and the like, as well as plants of the families Solanaceae, Brassicaceae, Malvaceae, and Fabaceae.

Infection and damage from many fungal pathogens, especially those which are filamentous fungi, can be controlled in many plant species using the present system. Examples of controllable fungal and oomycete pathogens include, but are not limited to, *Fusarium, Verticillium, Pythium, Rhizoctonia, Sclerotinia, Leptosphaeria, Phytophthora, Colletotrichum, Cercospora* and *Alternaria* species, and rust fungi. Important applications include, without being limiting, the synergistic combinations of a proteinase inhibitor and an antifungal defensin used, e.g. to protect plants from *Fusarium graminearum* (Fgr), *Fusarium oxysporum* f. sp. *vasinfectum* (Fov), *Colletotrichum graminicola* (Cgr), *Leptosphaeria* maculans, *Alternaria brassicicola*, *Alternaria alternata*, *Aspergillus nidulans*, *Botrytis cinerea*, *Cercospora beticola*, *Cercospora zeae maydis*, *Cochliobolus heterostrophus*, *Exserohilum turcicum*, *Fusarium culmorum*, *Fusarium oxysporum*, *Fusarium oxysporum* f. sp. *dianthi*, *Fusarium oxysporum* f. sp. *lycopersici*, *Fusarium solani*, *Fusarium pseudograminearum*, *Fusarium verticilloides* (Fve), *Gaeumannomyces graminis* var. *tritici*, *Plasmodiophora brassicae*, *Sclerotinia sclerotiorum*, *Stenocarpella* (*Diplodia*) *maydis;* *Thielaviopsis basicola*, *Verticillium dahliae*, *Ustilago zeae*, *Puccinia sorghi*, *Macrophomina phaseolina*, *Phialophora gregata*, *Diaporthe phaseolorum*, *Cercospora sojina*, *Phytophthora sojae*, *Rhizoctonia solani*, *Phakopsora pachyrhizi*, *Alternaria macrospora*, *Cercospora gossypina*, *Phoma exigua*, *Puccinia schedonnardii*, *Puccinia cacabata*, *Phymatotrichopsis omnivora*, *Fusarium avenaceum*, *Alternaria brassicae*, *Alternaria raphani*, *Erysiphe graminis* (*Blumeria graminis*), *Septoria tritici*, *Septoria nodorum;* *Mycosphaerella zeae*, *Rhizoctonia cerealis*, *Ustilago tritici*, *Puccinia graminis*, *Puccinia triticina*, *Tilletia indica*, *Tilletia caries*, and *Tilletia controversa*.

Insect pathogens include *Diatraea grandiosella*, *Ostrinia nubilalis*, *Rhopalosiphum* spp, *Helicoverpa* spp, *Plutella xylostella* and *Lygus* spp.

Agronomic compositions comprising a Class I defensin and a permeabilizing defensin or anti-fungal or anti-insect homologs, analogs, variants and functional equivalents thereof or their precursor forms are also contemplated herein. The compositions may also include a proteinase inhibitor or a precursor form thereof. An agronomic composition includes a seed coating formulation.

A protocol for managing plant pathogen infection of plants is further contemplated herein comprising the manipulation of a plant environment to provide a Class I defensin and a permeabilizing defensin in amounts which inhibit the pathogen.

Reference to "plant pathogen" in a particular embodiment includes a fungus and an insect or other related organisms. A fungus includes a rust. Generally, when the method comprises genetically modifying plants to express both defensins, the term "plant" includes its progeny. When the method comprises topically applying a combination of defensins, the effect is generally limited to a particular plant.

Whilst the instant disclosure is particularly directed to anti-phytopathogenic methods, the multivalent approach may also be used in human and non-human subjects, including farm animals, domestic animals, laboratory test animals and captured wild animals. Generally, a topical approach is used in these circumstances. Commonly, the multivalent approach in human and non-human subjects target inter alia yeasts such as *Candida* and *Cryptococcus*, dermatophytes such as *Trichophyton* including *Trichophyton interdigitale* and *Trichophyton rubrum* and other filamentous fungi including *Aspergillus* spp such as *Aspergillus niger*.

Further enabled herein is a method for protecting a plant from a disease associated with infection by a pathogen, the method comprising providing cells of the place with a Class I defensin having a mature domain comprising an amino acid sequence selected from SEQ ID NOs:81, 83, 85, 3, 6, 9, 12, 15, 18, 21, 24, 27, 30, 33, 36, 39, 42, 45, 48, 51, 54, 57, 60, 63, 66 and 69, a permeabilizing defensin having a mature domain selected from the listing consisting of NaD1, TPP3; PhD1A, PhD2, NoD173, SEQ ID NOs:3, 6, 12, 21, 24, 70, 71 and 72 or a precursor or a functional homolog, analog, derivative or variant thereof of either or both.

Further enabled herein is a method for protecting a plant from a disease associated with infection by a pathogen, the method comprising providing cells of the place with a Class I defensin having a mature domain comprising an amino acid sequence selected from SEQ ID NOs:81, 83, 85, 3, 6, 9, 12, 15, 18, 21, 24, 27, 30, 33, 36, 39, 42, 45, 48, 51, 54, 57, 60, 63, 66 and 69, a permeabilizing defensin having a mature domain selected from the listing consisting of SEQ ID NOs:3, 6, 12, 21, 24, 70, 71 and 72 or a precursor or a functional homolog, analog, derivative or variant thereof of either or both.

Further enabled herein is a method for protecting a human or non-human animal subject from a disease associated with infection by a pathogen, the method comprising providing cells of the place with a Class I defensin having a mature domain comprising an amino acid sequence selected from SEQ ID NOs:81, 83, 85, 3, 6, 9, 12, 15, 18, 21, 24, 27, 30, 33, 36, 39, 42, 45, 48, 51, 54, 57, 60, 63, 66 and 69, a permeabilizing defensin having a mature domain selected from the listing consisting of NaD1, TPP3, PhD1A, PhD2, NoD173, SEQ ID NOs:3, 6, 12, 21, 24, 70, 71 and 72 or a precursor or a functional homolog, analog, derivative or variant thereof of either or both.

TABLE 1

Summary of Sequence Identifiers

| Peptide | Source | Sequence type | Sequence ID |
|---|---|---|---|
| HXL001 | Zea mays | Full length nucleic acid (NA) | SEQ ID NO: 1 |
| | | Full length protein | SEQ ID NO: 2 |
| | | Mature domain | SEQ ID NO: 3 |
| HXL002 | Triticum aestivum | Full length NA | SEQ ID NO: 4 |
| | | Full length protein | SEQ ID NO: 5 |
| | | Mature domain | SEQ ID NO: 6 |
| HXL003 | Triticum aestivum | Full length NA | SEQ ID NO: 7 |
| | | Full length protein | SEQ ID NO: 8 |
| | | Mature domain | SEQ ID NO: 9 |
| HXL004 | Nicotiana benthamiana | Full length NA | SEQ ID NO: 10 |
| | | Full length protein | SEQ ID NO: 11 |
| | | Mature domain | SEQ ID NO: 12 |
| HXL005 | Taraxacum kok-saghyz | Full length NA | SEQ ID NO: 13 |
| | | Full length protein | SEQ ID NO: 14 |
| | | Mature domain | SEQ ID NO: 15 |
| HXL006 | Triticum aestivum | Full length NA | SEQ ID NO: 16 |
| | | Full length protein | SEQ ID NO: 17 |
| | | Mature domain | SEQ ID NO: 18 |
| HXL007 | Cyamopsis tetragonoloba | Full length NA | SEQ ID NO: 19 |
| | | Full length protein | SEQ ID NO: 20 |
| | | Mature domain | SEQ ID NO: 21 |
| HXL008 | Picramnia pentandra | Full length NA | SEQ ID NO: 22 |
| | | Full length protein | SEQ ID NO: 23 |
| | | Mature domain | SEQ ID NO: 24 |
| HXL009 | Zea mays | Full length NA | SEQ ID NO: 25 |
| | | Full length protein | SEQ ID NO: 26 |
| | | Mature domain | SEQ ID NO: 27 |
| HXL010 | Triticum aestivum | Full length NA | SEQ ID NO: 28 |
| | | Full length protein | SEQ ID NO: 29 |
| | | Mature domain | SEQ ID NO: 30 |
| HXL011 | Eucalyptus grandis | Full length NA | SEQ ID NO: 31 |
| | | Full length protein | SEQ ID NO: 32 |
| | | Mature domain | SEQ ID NO: 33 |
| HXL012 | Amaranthus retroflexus | Full length NA | SEQ ID NO: 34 |
| | | Full length protein | SEQ ID NO: 35 |
| | | Mature domain | SEQ ID NO: 36 |
| HXL013 | Glycine max | Full length NA | SEQ ID NO: 37 |
| | | Full length protein | SEQ ID NO: 38 |
| | | Mature domain | SEQ ID NO: 39 |
| HXL014 | Tulipa gesneriana | Full length NA | SEQ ID NO: 40 |
| | | Full length protein | SEQ ID NO: 41 |
| | | Mature domain | SEQ ID NO: 42 |
| HXL015 | Oryza sativa | Full length NA | SEQ ID NO: 43 |
| | | Full length protein | SEQ ID NO: 44 |
| | | Mature domain | SEQ ID NO: 45 |

TABLE 1-continued

Summary of Sequence Identifiers

| Peptide | Source | Sequence type | Sequence ID |
|---|---|---|---|
| HXL016 | Triticum aestivum | Full length NA | SEQ ID NO: 46 |
| | | Full length protein | SEQ ID NO: 47 |
| | | Mature domain | SEQ ID NO: 48 |
| HXL017 | Zea mays | Full length NA | SEQ ID NO: 49 |
| | | Full length protein | SEQ ID NO: 50 |
| | | Mature domain | SEQ ID NO: 51 |
| HXL018 | Parthenium argentatum | Full length NA | SEQ ID NO: 52 |
| | | Full length protein | SEQ ID NO: 53 |
| | | Mature domain | SEQ ID NO: 54 |
| HXL019 | Nicotiana benthamiana | Full length NA | SEQ ID NO: 55 |
| | | Full length protein | SEQ ID NO: 56 |
| | | Mature domain | SEQ ID NO: 57 |
| HXL020 | Triticum aestivum | Full length NA | SEQ ID NO: 58 |
| | | Full length protein | SEQ ID NO: 59 |
| | | Mature domain | SEQ ID NO: 60 |
| HXL021 | Arachis hypogaea | Full length NA | SEQ ID NO: 61 |
| | | Full length protein | SEQ ID NO: 62 |
| | | Mature domain | SEQ ID NO: 63 |
| HXL022 | Cyamopsis tetragonoloba | Full length NA | SEQ ID NO: 64 |
| | | Full length protein | SEQ ID NO: 65 |
| | | Mature domain | SEQ ID NO: 66 |
| HXL023 | Triticum aestivum | Full length NA | SEQ ID NO: 67 |
| | | Full length protein | SEQ ID NO: 68 |
| | | Mature domain | SEQ ID NO: 69 |
| HXP4 | Artificial | Protein | SEQ ID NO: 70 |
| HXP34 | Artificial | Protein | SEQ ID NO: 71 |
| HXP35 | Artificial | Protein | SEQ ID NO: 72 |
| HXP37 | Artificial | Protein | SEQ ID NO: 73 |
| HXP58 | Artificial | Protein | SEQ ID NO: 74 |
| HXP72 | Artificial | Protein | SEQ ID NO: 75 |
| HXP91 | Artificial | Protein | SEQ ID NO: 76 |
| HXP92 | Artificial | Protein | SEQ ID NO: 77 |
| HXP95 | Artificial | Protein | SEQ ID NO: 78 |
| HXP107 | Artificial | Protein | SEQ ID NO: 79 |
| VP42 | Triticum aestivum | Full length protein | SEQ ID NO: 80 |
| VP42 | Triticum aestivum | Mature domain | SEQ ID NO: 81 |
| VP45 | Zea mays | Full length protein | SEQ ID NO: 82 |
| VP45 | Zea mays | Mature domain | SEQ ID NO: 83 |
| VP135 | Picramnia pentandra | Full length protein | SEQ ID NO: 84 |
| VP135 | Picramnia pentandra | Mature domain | SEQ ID NO: 85 |
| Linker (for a MGEV) | Artificial | — | SEQ ID NO: 86 |
| HXL032 | Triticum aestivum | Full length NA | SEQ ID NO: 87 |
| HXL032 | Triticum aestivum | Full length protein | SEQ ID NO: 88 |
| HXL032 | Triticum aestivum | Mature domain | SEQ ID NO: 89 |
| HXL033 | Parthenium argentatum | Full length NA | SEQ ID NO: 90 |
| HXL033 | Parthenium argentatum | Full length protein | SEQ ID NO: 91 |
| HXL033 | Parthenium argentatum | Mature domain | SEQ ID NO: 92 |
| HXL034 | Nicotiana benthamiana | Full length NA | SEQ ID NO: 93 |
| HXL034 | Nicotiana benthamiana | Full length protein | SEQ ID NO: 94 |
| HXL034 | Nicotiana benthamiana | Mature domain | SEQ ID NO: 95 |
| NoD173 | Nicotiana occidentalis | Full length NA | SEQ ID NO: 96 |
| NoD173 | Nicotiana occidentalis | Full length protein | SEQ ID NO: 97 |
| NoD173 | Nicotiana occidentalis | Mature domain | SEQ ID NO: 98 |

TABLE 2

Examples of plant defensins

| Peptide | Source | Accession number | Type (Class I, Class II or variant) | Permeabilizing | Reference |
|---|---|---|---|---|---|
| NaD1 | Nicotiana alata | Q8GTM0 | Class II | Yes | Lay et al, 2003 |
| PhD1A | Petunia hybrida | Q8H6Q1 | Class II | Yes | Lay et al, 2003 |
| PhD2 | Petunia hybrida | Q8H6Q0 | Class II | Yes | Lay et al, 2003 |
| TPP3 | Solanum lycopersicum | AAA80496 | Class II | Yes | Milligan & Gasser, 1995 |
| MtDef4 | Medicago truncatula | | Class I | | Sagaram et al, 2011 |
| VP42 | Triticum aestivum | | Class I | No | SEQ ID NO: 81 |
| VP45 | Zea mays | | Class I | No | SEQ ID NO: 83 |
| VP135 | Picramnia pentandra | | Class I | No | SEQ ID NO: 85 |
| SBI6 | Glycine max | | Class I | | SEQ ID NO: 39 |
| γ1-H | Hordeum vulgare | P20230 | Class I | No | Mendez et al, 1990 |
| γ-Zea2 | Zea mays | P81009 | Class I | | Castro et al, 1996 |
| RsAFP2 | Raphanus sativus | P30230 | Class I | No | Terras et al, 1992 |
| DmAMP1 | Dahlia merckii | AAB34972 | Class I | No | Osborn et al, 1995 |
| MsDef1 | Medicago sativa | AAV85437 | Class I | | Hanks et al, 2005 |
| MtDef2 | Medicago truncatula | AY313169 | Class I | | Spelbrink et al, 2004 |
| PsD1 | Pisum sativum | P81929 | Class I | | Almeida et al, 2000 |
| HsAFP1 | Heuchera sanguinea | AAB34974 | Class I | | Osborn et al, 1995 |
| VaD1 | Vigna angularis | n/a | Class I | | Chen et al, 2005 |
| VrD2 | Vigna radiata | 2GL1_A | Class I | | Lin et al, 2007 |
| ZmESR6 | Zea mays | CAH61275 | Class I | | Balandin et al, 2005 |
| HXL001 | Zea mays | — | Class I | Yes | SEQ ID NO: 3 |
| HXL002 | Triticum aestivum | — | Class I | Yes | SEQ ID NO: 6 |
| HXL003 | Triticum aestivum | — | Class I | | SEQ ID NO: 9 |
| HXL004 | Nicotiana benthamiana | — | Class I | Yes | SEQ ID NO: 12 |
| HXL005 | Taraxacum kok-saghyz | — | Class I | No | SEQ ID NO: 15 |
| HXL006 | Triticum aestivum | — | Class I | | SEQ ID NO: 18 |
| HXL007 | Cyamopsis tetragonoloba | — | Class I | Yes | SEQ ID NO: 21 |
| HXL008 | Picramnia pentandra | — | Class I | Yes | SEQ ID NO: 24 |
| HXL009 | Zea mays | — | Class I | No | SEQ ID NO: 27 |
| HXL010 | Triticum aestivum | — | Class 1 | | SEQ ID NO: 30 |
| HXL011 | Eucalyptus grandis | — | Class I | | SEQ ID NO: 33 |
| HXL012 | Amaranthus retroflexus | — | Class I | | SEQ ID NO: 36 |
| HXL013 | Glycine max | — | Class I | Yes | SEQ ID NO: 39 |
| HXL014 | Tulipa gesneriana | — | Class I | | SEQ ID NO: 42 |
| HXL015 | Oryza sativa | — | Class I | No | SEQ ID NO: 45 |

TABLE 2-continued

Examples of plant defensins

| Peptide | Source | Accession number | Type (Class I, Class II or variant) | Permeabilizing | Reference |
|---|---|---|---|---|---|
| HXL016 | *Triticum aestivum* | — | Class I | | SEQ ID NO: 48 |
| HXL017 | *Zea mays* | — | Class I | | SEQ ID NO: 51 |
| HXL018 | *Parthenium argentatum* | — | Class I | | SEQ ID NO: 54 |
| HXL019 | *Nicotiana benthamiana* | — | Class I | | SEQ ID NO: 57 |
| HXL020 | *Triticum aestivum* | — | Class I | | SEQ ID NO: 60 |
| HXL021 | *Arachis hypogaea* | — | Class I | No | SEQ ID NO: 63 |
| HXL022 | *Cyamopsis tetragonoloba* | — | Class I | | SEQ ID NO: 66 |
| HXL023 | *Triticum aestivum* | — | Class I | | SEQ ID NO: 69 |
| HXP4 | Artificial | | Variant | Yes | SEQ ID NO: 70 |
| HXP34 | Artificial | | Variant | Yes | SEQ ID NO: 71 |
| HXP35 | Artificial | | Variant | Yes | SEQ ID NO: 72 |
| HXP37 | Artificial | | Variant | | SEQ ID NO: 73 |
| HXP58 | Artificial | | Variant | | SEQ ID NO: 74 |
| HXP72 | Artificial | | Variant | | SEQ ID NO: 75 |
| HXP91 | Artificial | | Variant | | SEQ ID NO: 76 |
| HXP92 | Artificial | | Variant | | SEQ ID NO: 77 |
| HXP95 | Artificial | | Variant | | SEQ ID NO: 78 |
| HXP107 | Artificial | | Variant | | SEQ ID NO: 79 |
| HXL032 | *Triticum aestivum* | | Class I | | SEQ ID NO: 89 |
| HXL033 | *Parathenium argentatum* | | Class I | | SEQ ID NO: 92 |
| HXL034 | *Nicotiana benthamiana* | | Class I | | SEQ ID NO: 95 |
| NoD173 | *Nicotiana occidentalis sppoblique* | | Class II | Yes | SEQ ID NO: 98 |

DETAILED DESCRIPTION

Figure 1:
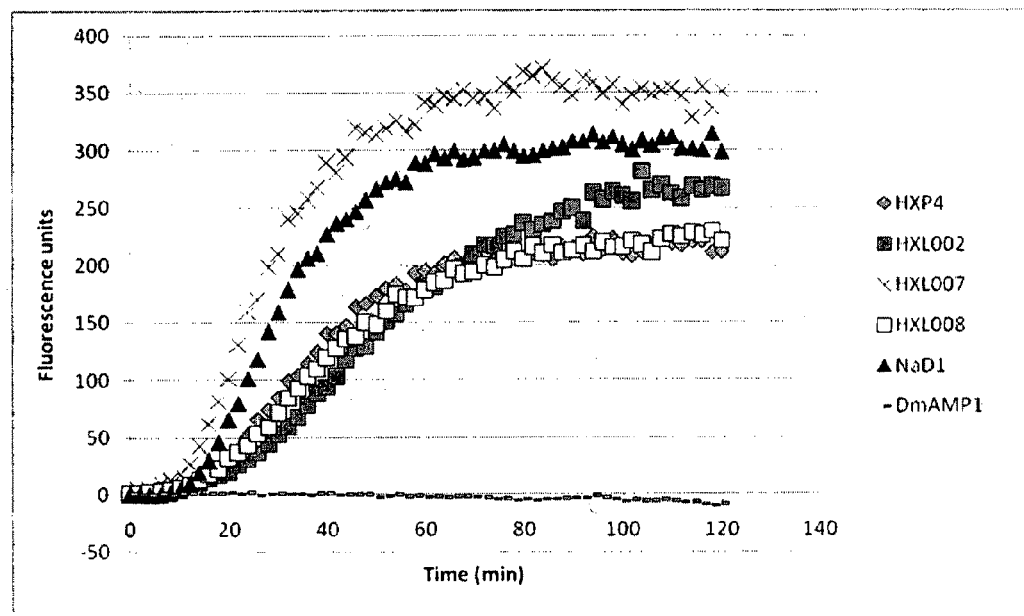
FIG. 1 is a graphical representation showing the results of a permeabilization assay on Fov hyphae demonstrating the difference between permeabilizing (NaD1, HXP4, HXL002, HXL007 and HXL008) and non-permeabilizing (DmAMP1) defensins.

A phytopathogenic fungus includes but is not limited to *Fusarium graminearum* (Fgr), *Fusarium oxysporum* f. sp. *vasinfectum* (Fov), *Colletotrichum graminicola* (Cgr), *Leptosphaeria maculans*, *Alternaria brassicicola*, *Alternaria alternata*, *Aspergillus nidulans*, *Botrytis cinerea*, *Cercospora beticola*, *Cercospora zeae maydis*, *Cochliobolus heterostrophus*, *Exserohilum turcicum*, *Fusarium culmorum*, *Fusarium oxysporum*, *Fusarium oxysporum* f. sp. *dianthi*, *Fusarium oxysporum* f. sp. *lycopersici*, *Fusarium solani*, *Fusarium pseudograminearum*, *Fusarium verticilloides* (Fve), *Gaeumannomyces graminis* var. *tritici*, *Plasmodiophora brassicae*, *Sclerotinia sclerotiorum*, *Stenocarpella* (*Diplodia*) *maydis*, *Thielaviopsis basicola*, *Verticillium dahliae*, *Ustilago zeae*, *Puccinia sorghi*, *Macrophomina phaseolina*, *Phialophora gregata*, *Diaporthe phaseolorum*, *Cercospora sojina*, *Phytophthora sojae*, *Rhizoctonia solani*, *Phakopsora pachyrhizi*, *Alternaria macrospora*, *Cercospora gossypina*, *Phoma exigua*, *Puccinia schedonnardii*, *Puccinia cacabata*, *Phymatotrichopsis omnivora*, *Fusarium avenaceum*, *Alternaria brassicae*, *Alternaria raphani*, *Erysiphe graminis* (*Blumeria graminis*), *Septoria tritici*, *Septoria nodorum*, *Mycosphaerella zeae*, *Rhizoctonia cerealis*, *Ustilago tritici*, *Puccinia graminis*, *Puccinia triticina*, *Tilletia indica*, *Tilletia caries* and *Tilletia*.

A fungal pathogen of human and non-human subjects includes yeasts such as *Candida* and *Cryptococcus*, dermatophytes such as *Trichophyton* such as *Trichophyton interdigitale* and *Trichophyton rubrum* and other filamentous fungi including *Aspergillus* spp such as *Aspergillus niger*.

A phytopathogenic insect includes *Diatraea grandiosella*, *Ostrinia nubialis*, *Rhopalosiphum* spp, *Helicoverpa* spp, *Plutella xylostella* and *Lygus* spp.

Reference to "variant" includes a derivative of a particular sequence as well as a natural variant such as a polymorphic variant. It also includes synthetic variants such as defensins comprising a heterologous domain or loop such as from another defensin, such as described in PCT/AU2012/000112, the contents of which are incorporated herein by reference.

The inhibitory effect of a given pair of defensins is proposed herein to be synergistic. Greco et al. (1995) *Pharmacol Rev* 47:331-385 has defined different categories of synergy, according to whether one, both or neither of the two components has measurable activity when assayed in the absence of the other component. The definition adopted herein includes all such situations provided that the combined effect of the two components acting together is greater than the sum of the individual components acting alone. It will be understood that a synergistic combination of two or more components may yield greater than additive activity only under certain conditions; e.g. when one or more of the components is present at a lower concentration than is maximal for individual efficacy. A combination of components is deemed synergistic, as the term is intended herein, if there exists a set of conditions, including but not limited to concentrations, where the combined effect of the components acting together is greater than the sum of the individual components acting alone. Richer (1987) supra describes a mathematical approach to establish proof of synergy. This approach uses Limpel's formula which is defined in Richer (1987) supra and was used by Harman et al. U.S. Pat. No. 6,512,166 to prove synergy between fungal cell wall degrading enzymes and fungal cell membrane affecting compounds on the growth of plant pathogenic fungi. A similar approach can be used for insects.

Synergy is classified as the difference between the observed % fungal growth inhibition caused by the combination of two defensins (Io value) and the expected % fungal growth inhibition of the two defensins based on the sum of the % fungal growth inhibition of each defensin on its own (Ee value calculated according to the Limpel formula used by Richer et al. (1987) supra). The difference, Io-Ee, is the synergy value. A synergy value up to 15 means no significant synergy; 15-30 is a low level of synergy; 30-60 is a medium level of synergy; and >60 is a high level of synergy.

"Fungal inhibition" includes both fungicidal and fungi static activity, as measured by reduction of fungal growth (or loss of viability) compared to a control. Fungal growth can be measured by many different methods known in the art. A commonly used method of measuring growth of a filamentous fungus entails germinating spores in a suitable growth medium, incubating for a time sufficient to achieve measurable growth, and measuring increased optical density in the culture after a specified incubation time. The optical density is increased with increased growth. Typically, fungal growth is necessary for pathogenesis. Therefore, inhibition of fungal growth provides a suitable indicator for protection from fungal disease, i.e. the greater the inhibition, the more effective the protection. Similarly, "insect inhibition" include both insecticidal and insectistatic activity. Anti-insect activity can be usefully measured in feeding trials.

"Preventing infection" in the present context, means that the plants or human or non-human animal subjects treated by the method of the present invention, avoid pathogen infection or disease symptoms or all of the above, or exhibit reduced or minimized or less frequent pathogen infection or disease symptoms or all of the above, that are the natural outcome of the subject-pathogen interactions when compared to plants not expressing the two defensin transgenes or treated with the two defensins. That is to say, pathogens are prevented or reduced from causing disease and/or the associated disease symptoms. Infection and/or symptoms are reduced at least about 10%, 20%, 30%, 40%, 50%, 60%, 70% or 80% or greater as compared to a plant not so treated with the method taught herein. In an aspect, the method herein disclosed results in reduced sporulation of the pathogenic fungus to a greater extent in the presence of both defensins.

Hence, the combined action of the defensins is to inhibit fungal growth, replication, infection and/or maintenance, amongst other inhibitory activities and/or to inhibit insect infestation.

Plant protection (disease resistance or reduction) can be evaluated by methods known in the art. See, Uknes (1993) *Molecular Plant Microbe Interactions* 6:680-685; Gorlach et al. (1996) *Plant Cell* 8:629-643; Alexander et al. (1993) *Proc Natl Acad Sci USA* 90:7327-7331. The skilled artisan will recognize that methods for determining plant infection and disease by a plant pathogen depends on the pathogen and plant being tested.

Reference to a "Class I" defensin includes permeabilizing and non-permeabilizing defensins. Reference to a "permeabilizing defensin" includes a Class I defensin, a Class II defensin and a variant defensin, which is a permeabilizing defensin. A "variant" defensin includes a defensin wherein a Loop 1B region from a Class II defensin is replaced by a Loop 1B region on a Class I defensin or the Class II Loop 1B region is otherwise subject to one or more amino acid substitutions, additions or deletions. The Loop 1B region is located between the first n-strand (β-strand 1) and the α-helix on the defensin N-terminal end portion (also referred to as the first flexible loop). As indicated above, plant defensins are divided into two major classes. Class I defensins consist of an endoplasmic reticulum (ER) sequence followed by a mature defensin domain. Class II defensins are produced as larger precursors with C-terminal pro-domains or pro-peptides (CTPPs) of about 33 amino acids in addition to the ER signal sequence and mature domain.

A permeabilizing defensin is one which permits entry of a DNA-binding dye such as SYTOX (Registered Trade Mark) into hyphal cells. For example, hyphae are grown and incubated with the DNA binding dye for 10 minutes prior to addition of a peptide to be tested for its ability to be permeabilizing. DNA-binding dye-uptake is then measured. In the case of SYTOX, measurement is by fluorescence with excitation and emission wavelengths of 488 nm and 538 nm, respectively. Conveniently, the permeabilizing assay is conducted using *Fusarium oxysporum* f. sp. *vasinfectum* (Fov). In this assay, the permeabilizing defensin NaD1 is set as 1.0 and any defensin peptide giving a permeability index greater than 0.12 is regarded as a permeabilizing defensin. See FIG. 1 and Table 12a. More information can be found in PCT/AU2009/000106.

Another assay involves *Fusarium graminearum* (Fgr), again using NaD1 as the positive control, set at a permeabilization index of 1.0. See FIG. 2 and Table 12b.

Reference to a Class I defensin includes hordothionin (γ1-H), zeathionin (γ-Zea2), PsD1, DmAMP1, SBI6, VP42, VP45, VP135, RsAFP2, MsDef1, MtDef2, MtDef4, HsAFP1, VaD2, VrD2, ZmESR6 or a HXL defensin (see Table 2). Reference to a permeabilizing defensin includes Class II defensins such as NaD1, TPP3, PhD1A or PhD2, NoD173, Class I defensins such as HXL001, HXL002, HXL004, HXL007 or HXL008 or variant defensins such as HXP4, HXP34 or HXP35 (see Table 2). Particularly useful combinations include HXP4, NaD1, HXL004, HXL001 and/or HXL008 as a permeabilizing defensin and HXL012, HXL015, SB16, HXL009, HXL008 and/or HXL021 as the Class I defensin.

Further enabled herein is a method for protecting a plant or human or non-human animal subject from a disease associated with infection by a pathogen, the method comprising providing cells of the place with a Class I defensin having a mature domain comprising an amino acid sequence selected from SEQ ID NOs:81, 83, 85, 3, 6, 9, 12, 15, 18, 21, 24, 27, 30, 33, 36, 39, 42, 45, 48, 51, 54, 57, 60, 63, 66 and 69, a permeabilizing defensin having a mature domain selected from the listing consisting of NaD1, TPP3, PhD1A, PhD2, NoD173, SEQ ID NOs:3, 6, 12, 21, 24, 70, 71 and 72 or a precursor or a functional homolog, analog, derivative or variant thereof of either or both.

Further enabled herein is a method for protecting a plant or human or non-human animal subject from a disease associated with infection by a pathogen, the method comprising providing cells of the place with a Class I defensin having a mature domain comprising an amino acid sequence selected from SEQ ID NOs:81, 83, 85, 3, 6, 9, 12, 15, 18, 21, 24, 27, 30, 33, 36, 39, 42, 45, 48, 51, 54, 57, 60, 63, 66 and 69, a permeabilizing defensin having a mature domain selected from the listing consisting of SEQ ID NOs:3, 6, 12, 21, 24, 70, 71 and 72 or a precursor or a functional homolog, analog, derivative or variant thereof of either or both.

The term "proteinase inhibitor" is used herein to include proteins or peptides used to inhibit the activity of fungal or insect proteinases and to protect plants or human or non-human animal subjects from fungal or insect disease.

Chemical analogs or functional equivalents of the proteinase inhibitors are also encompassed herein.

The proteinase inhibitor may also be provided in a precursor form which is processed into an active form prior to being effective.

Cysteine proteinase inhibitors, or cystatins, are tight and reversibly binding inhibitors of cysteine proteases. They comprise a super family subdivided into three families: the stefins, the cystatins and the kininogens (Turk and Bode (1991) *FEBS Lett.* 285:213-219).

Serine proteinase inhibitors, or serine endopeptidases, cleave peptide bonds in which serine serves as the nucleophilic amino acid. There are generally two categories: chymotrypsin-like, which includes trypsin-like chymotroypsin-like and elastase-like; and subtilisin-like (Madala et al. (2010) *Chem Rev* 110(6):1-31).

A "synergistic effect" occurs where two or more components within the method produce a combined effect that is greater than the sum of the individual effects of each component acting alone. The effect may be one or more of efficacy, stability, rate, and/or level of toxicity. As described herein, synergistic pathogen growth inhibition measured in the combined presence of a Class I defensin and a permeabilizing defensin is greater than the summed inhibition measured in the presence of a particular concentration range of each defensin component, individually, under otherwise identical conditions. It will be understood that it is not necessary that a greater than additive effect be observed with every combination of concentrations of the two components in order to be deemed synergistic. The synergistic effect of two components can be observed under certain concentration combinations, but not in others. For example, if the inability to enter the fungal cell limits toxicity, the presence of a permeabilizing defensin can result in synergy with respect to a second defensin, especially if the concentration of defensin is sub-maximal with respect to inhibition. In an embodiment, the concentration of one or both of the defensin(s) is sub-maximal. By the same token, synergy can be masked if one or both components is present at such a high level (maximum level) as to result in maximum observable inhibition. The general system for a defensin-defensin combination is, therefore, termed "synergistic" because the potential for synergy is present even if synergy is not observed under all conditions. The synergy between two plant defensins provides greater fungal inhibition than can be obtained by either component acting alone, for at least some dosages. The present disclosure teaches increased protection of plants from fungal disease and insect infestation with reduced dependence on chemical fungicides or insecticides. This means decreased input cost to growers, a broader spectrum of activity against plant pathogens and reduced potential for environmental damage. In addition, the selection pressure for development of pathogenicide-resistant pathogen strains is greatly reduced, which allows for an extended commercial life as well as reduced proliferation of resistant fungus strains and reduced likelihood of emergence of multiple-resistant strains.

Hence, the method of the present disclosure is useful for reducing economic loss due to fungal or insect infection or infestation. It also facilitates amelioration of disease or symptoms of disease following pathogen exposure to human and non-human animal subjects.

In an aspect taught herein, a method is provided for the protection of a plant from a disease associated with a pathogen such as a fungal or insect agent, and that prevention or treatment results in decreased need for pathogenicide treatment of plants or plant parts, thus lowering costs of material, labor, and environmental pollution, or prolonging shelf-life of products (e.g. fruit, seed, and the like) of such plants.

In an embodiment, the pathogen is a fungus. Reference to a non-human animal subject includes a farm animal (e.g. cow, sheep, pig, horse, donkey, Llama, alpaca, avian animal), domestic animal (e.g. dogs, cat), laboratory test animal (e.g. mouse, rat, guinea pig, rabbit, hamster, non-human primate) and captured wild animal.

The term "plant" includes whole plants and parts thereof, including, but not limited to, shoots, vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, and the like), and progeny of same. The plants that can be protected using the method herein described include higher and lower plants, including angiosperms (monocotyledonous and dicotyledonous plants), gymnosperms, ferns, horsetails, psilophytes, lycophytes, bryophyte, and multicellular algae. Plants for use in the subject method include any vascular plant, for example monocotyledons or dicotyledons or gymnosperms, including, but not limited to, corn (and maize), soybean, cotton, cottonseed, canola, wheat, alfalfa, apple, *Arabidopsis*, banana, barley, castor bean, *chrysanthemum*, clover, cocoa, coffee, *crambe*, cranberry, cucumber, dendrobium, *dioscorea, eucalyptus*, fescue, flax, *gladiolus*, liliacea, linseed, millet, muskmelon, mustard, oat, oil palm, oilseed rape (rape, *rapa*), *papaya*, peanut, pineapple, ornamental plants, *Phaseolus*, potato, rapeseed, rice, rye, ryegrass, safflower, sesame, sorghum, sugarbeet, sugarcane, sunflower, strawberry, tobacco, tomato, turfgrass and vegetable crops such as lettuce, celery, broccoli, cauliflower, cucurbits, onions (including garlic, shallots, leeks, and chives); fruit and nut trees, such as apple, pear, peach, orange, grapefruit, lemon, lime, almond, pecan, walnut, hazelnut; vines, such as grapes, kiwifruit, hops; fruit shrubs and brambles, such as raspberry, blackberry, gooseberry; and forest trees, such as ash, pine, fir, maple, oak, chestnut and poplar.

Particular plants contemplated herein include corn, soybean, cotton, canola and wheat.

Reference to "insect pathogen" includes insects of the following phyla: *Diatraea grandiosella, Ostrinia nubialis, Rhopalosiphum* spp, *Helicoverpa* spp, *Plutella xylostella* and *Lygus* spp.

A "transgenic plant" refers to a plant, or seed thereof or its progeny, that contains genetic material not found (i.e. "exogenous") in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes. The term "genetically modified plant" may also be used which has the same meaning as a "transgenic plant" in this context. In an embodiment, the plant or part thereof such as a seed is genetically modified to express one defensin and the second defensin is exogenously supplied such as a seed coating or a topical formulation.

A transgenic plant may contain an expression vector or cassette. The expression cassette typically comprises a polypeptide-encoding sequence operably linked (i.e. under regulatory control of) to appropriate inducible or constitutive regulatory sequences that allow for the expression of the polypeptide. The expression cassette can be introduced into a plant by transformation or by breeding after transformation of a parent plant. An example of a suitable expression cassette is disclosed in U.S. patent application Ser. No. 11/753,072 [equivalent of PCT/AU2007/000712] the contents of which are incorporated herein by reference.

The plant or plant part for use in the present method includes plants of any stage of plant development. Conveniently, the application occurs during the stages of germination, seedling growth, vegetative growth, and reproductive growth. Particular, applications of the present method occur during vegetative and reproductive growth stages. The stages of vegetative and reproductive growth are also referred to herein as "adult" or "mature" plants. A combination of plant genetic engineering and topical application of a defensin is also taught herein. Furthermore, one or other of the defensins may be introduced by genetic engineering means and the other is introduced by conventional breeding practices.

Whilst the present disclosure provides a method for protecting plants from fungal or insect infection using the synergistic action between a Class I defensin and a permeabilizing defensin, it is understood that additional materials can be added to the combination to achieve even more benefit with respect to the health of the plant, for example, by incorporating a proteinase inhibitor, or a fungicidal or insecticidal protein, or by utilizing more than one of either or both of the two types of defensins. For example, the spectrum of activity against plant pathogens can potentially be expanded by using additional agents.

The defensin components are conveniently supplied by the plant that is to be protected after genetic modification, although the present method extends to surface sprays or seed coatings as well as incorporation in fertilizers and plant food. In an embodiment, the plant is genetically modified to express the desired two defensins using methods well-known in the art.

Plant protection (disease resistance or reduction) can be evaluated by methods known in the art. See, Uknes (1993) *Molecular Plant Microbe Interactions* 6-680-685; Gorlach et al. (1996) supra; Alexander et al. (1993) supra. The skilled artisan will recognize that methods for determining plant infection and disease by a plant pathogen depends on the pathogen and plant being tested.

Further enabled herein is a method for protecting a human or non-human animal subject from a disease associated with infection by a fungal or insect pathogen, the method comprising providing cells of the human or non-human animal with a Class I defensin and a permeabilizing defensin or a precursor or a functional homolog, analog, derivative or variant thereof of either or both in a synergistically effective amount to reduce infection by the pathogen.

The present disclosure further contemplates the use of a Class I defensin and a permeabilizing defensin or a precursor form of either or both in the manufacture of a medicament for the treatment of a fungal infestation in a human or non-human animal subject.

As indicated above, the Class I defensin may be a permeabilizing or non-permeabilizing defensin. Hence, one or two permeabilizing defensins may be used.

In an embodiment, the nucleic acid is operably linked to a promoter and introduced into the genome of a plant cell. Upon appropriate conditions, the promoter enables expression of the nucleic acid molecule to produce an mRNA which is then translated into the defensin protein. The plant cell is used to regenerate a plant which is referred to as a "genetically modified plant". The genetic modification is the introduction of an expressible nucleic acid molecule to enable production of a defensin which in turn confers on cells of the plant, resistance to fungal pathogen infestation.

The nucleic acid sequences can be expressed in a plant cell. It is expected that those of skill in the art are knowledgeable in the numerous expression systems available for expression of a nucleic acid encoding a defensin protein. No attempt will be made to describe in detail the various methods known for the expression of proteins in plant cells.

As used herein, "heterologous" in reference to a nucleic acid is a nucleic acid that originates from a plant species or strain different to the intended recipient plant of the nucleic acid. For example, a promoter operably linked to a heterologous nucleotide sequence can be from a plant species different from that from which the nucleotide sequence was derived.

By a "genetically modified plant" is meant a plant comprising cells which comprise a heterologous nucleic acid sequence. It may be derived directly from a regenerated plant, its progeny or by a combination of genetic engineering and conventional breeding. A "heterologous" nucleic acid in this context means a nucleic acid encoding, one or other or both defensins and optionally a proteinase inhibitor or precursor form thereof.

The defensin sequences are generally provided in expression cassettes or DNA constructs for expression in the plant of interest. The cassette will include 5' and 3' regulatory sequences operably linked to a defensin sequence of the invention. By "operably linked" a functional linkage between a promoter and a second sequence, wherein the promoter sequence initiates and mediates transcription of the DNA sequence corresponding to the second sequence is intended. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the defensin sequence to be under the transcriptional regulation of the regulatory regions. The expression cassette may additionally contain selectable marker genes.

The expression cassette includes in the 5'-3' direction of transcription, a transcriptional and translational initiation region, a defensin DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

Whilst it may be useful to express the sequences using heterologous promoters, native promoter sequences may also be use.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant cell. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477-498.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126-6130); potyvirus leaders, for example, TEV leader (Tobacco Etch Virus) [Allison et al. (1986); MDMV leader (Maize Dwarf Mosaic Virus); *Virology* 154:9-20], and human immunoglobulin heavy-chain binding protein (BiP), (Macejak et al. (1991) *Nature* 353:90-94); untranslated leader from the coat protein mRNA of alfalfa mosaic virus (AMV RNA 4) [Jobling et al. (1987) *Nature* 325:622-625]; tobacco mosaic virus leader (TMV) (Gallie et al. (1989) In *Molecular Biology of RNA*, ed. Cech (Liss, New York), pp. 237-256); and maize chlorotic mottle virus leader (MCMV) [Lommel et al. (1991) *Virology* 81:382-385]. See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318.

The above list of selectable marker genes is not meant to be limiting. Any selectable marker gene can be used.

A number of promoters can be used in the generation of expression constructs. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J* 3:2723-2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611. These references are incorporated herein by reference.

Further enabled herein is a multigene expression vehicle (MGEV) comprising a polynucleotide having 2 to 8 domain segments, each domain encoding a functional protein wherein at least one domain encodes a Class I defensin and at least one other domain encodes a permeabilizing defensin, each domain being joined to the next in a linear sequence by a linker sequence encoding a linker, peptide having the amino acid sequence set forth in SEQ ID NO:86.

In an embodiment, at least one other domain encodes a proteinase inhibitor or a precursor form thereof. As indicated above, the MGEV vector is described in USSN 2007-0277263 which is incorporated herein by reference.

The linker peptide comprises the amino acid sequence $X_1X_2X_3X_4X_5$ (SEQ ID NO:86) wherein:
$X_1$=E or D
$X_2$=E or D
$X_3$=K or R
$X_4$=K or R
$X_5$=N or Q.

The method of transformation/transfection is not critical to the instant disclosure; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation. (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050;

Tomes et al., U.S. Pat. No. 5,879,918; Tomes et al., U.S. Pat. No. 5,886,244; Bidney et al., U.S. Pat. No. 5,932,782; McCabe et al. (1988) *Biotechnology* 6:923-926); and Lec1 transformation (WO 00/28058). Also see Weising et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) supra (soybean); Finer and McMullen (1991) In *Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al. U.S. Pat. Nos. 5,322,783 and 5,324,646; Tomes et al. (1995) "*Direct DNA Transfer into Intact Plant Cells via Microprojectile Bombardment,*" in Plant Cell, Tissue, and Organ Culture: Fundamental Methods, ed. Gamborg (Springer-Verlag, Berlin) (maize); Klein et al. (1989) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Ishida et al. (1996) *Nature Biotechnology* 14:745-750 (maize via *Agrobacterium tumefaciens*). These references are incorporated herein by reference, together with USSN 2010-0095408.

Purified defensin proteins can, if desired, be used or optionally combined with a proteinase inhibitor as a mixture, provided they can be formulated together or sequentially by separate application means. In a further embodiment, a multiplex approach is used where one of the components is engineered to be produced by the plant and the other component is exogenously supplied. These may be liberally applied or used on selected sites such as seed coatings or around the root tissue or surrounding soil.

In an aspect, the present disclosure teaches a method for the protection of a plant from a disease associated with a fungal pathogen and that prevention or treatment results in decreased need for pathogenicide treatment of plants or plant parts, thus lowering costs of material, labor, and environmental pollution, or prolonging shelf-life of products (e.g. fruit, seed, and the like) of such plants. The method requires genetically modifying a plant to express a Class I defensin and a permeabilizing defensin or applying these defensins topically. The term "plant" includes whole plants and parts thereof, including, but not limited to, shoots, vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, and the like), and progeny of same.

Agronomically useful compositions suitable for use in the system disclosed herein include compositions wherein the active ingredient(s) are contained in an effective amount to achieve the intended purpose such compositions include seed coatings. Determination of the effective amounts is well within the capability of those skilled in the art, especially in light of the disclosure provided herein.

In addition to the active ingredients, these compositions for use in the antifungal method may contain suitable agronomically acceptable carriers comprising excipients and auxiliaries which facilitate processing of the active compounds into preparations which can be used in the field, in greenhouses or in the laboratory setting.

Antifungal formulations include aqueous solutions of the active compounds in water-soluble form. Additionally, suspensions of the active compounds may be prepared as appropriate oily suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Further components can include viscosifiers, gels, wetting agents, ultraviolet protectants, among others.

Preparations for surface application can be obtained by combining the active compounds with solid excipient, optionally grinding a resulting mixture, and processing the mixture of granules, after adding suitable auxiliaries, if desired, to obtain powders for direct application or for dissolution prior to spraying on the plants to be protected. Suitable excipients are, in particular, fillers such as sugars, including lactose, sucrose, mannitol, or sorbitol; cellulose or starch preparations, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Whilst the instant disclosure is particularly directed to anti-phytopathogenic methods, the multivalent approach may also be used in human and non-human subjects, including farm animals and domestic animals. Generally, a topical approach is used in these circumstances. Commonly, the multivalent approach in human and non-human subjects target inter alia yeasts such as *Candida* and *Cryptococcus*, dermatophytes such as *Trichophyton* and other filamentous fungi including *Aspergillus* spp such as *Aspergillus niger.*

The present disclosure further teaches the use of a Class I defensin and a permeabilizing defensin and optionally a proteinase inhibitor or a functional homolog, analog, derivative or variant thereof of any one or all of these components in a human or non-human animal subject or its progeny resistant to fungal or insect pathogen infestation.

Further enabled herein is a method for protecting a human or non-human animal subject from a disease associated with infection by a pathogen, the method comprising providing cells of the place with a Class I defensin having a mature domain comprising an amino acid sequence selected from SEQ ID NOs:81, 83, 85, 3, 6, 9, 12, 15, 18, 21, 24, 27, 30, 33, 36, 39, 42, 45, 48, 51, 54, 57, 60, 63, 66 and 69, a permeabilizing defensin having a mature domain selected from the listing consisting of NaD1, TPP3, PhD1A, PhD2, NoD173, SEQ ID NOs:3, 6, 12, 21, 24, 70, 71 and 72 or a precursor or a functional homolog, analog, derivative or variant thereof of either or both.

Further enabled herein is a method for protecting a human or non-human animal subject from a disease associated with infection by a pathogen, the method comprising providing cells of the place with a Class I defensin having a mature domain comprising an amino acid sequence selected from SEQ ID NOs:81, 83, 85, 3, 6, 9, 12, 15, 18, 21, 24, 27, 30, 33, 36, 39, 42, 45, 48, 51, 54, 57, 60, 63, 66 and 69, a permeabilizing defensin having a mature domain selected from the listing consisting of SEQ ID NOs:3, 6, 12, 21, 24, 70, 71 and 72 or a precursor or a functional homolog, analog, derivative or variant thereof of either or both.

A topical composition for treating plants and human and non-human animal subjects is contemplated herein comprising a Class I defensin and a permeabilizing defensin or a precursor or functional homolog, analog, derivative or variant thereof or either or both. Additional excipients or carriers may also be included.

EXAMPLES

The present invention is further described in the following non-limiting Examples.

Methods,

Purification of Defensins from *Pichia pastoris*

A single pPINK-defensin *P. pastoris* PichiaPink (Trademark) strain 1 colony was used to inoculate 25 mL of BMG medium (described in the Invitrogen *Pichia* Expression Manual) in a 250 mL flask and that was incubated over for 2-3 days in a 30° C. shaking incubator (140 rpm). The culture was used to inoculate. 200 mL of BMG in a 1 L baffled flask which was placed in a 30° C. shaking incubator (140 rpm) overnight. The cells were harvested by centrifugation (2,500×g, 10 min, 4° C.) and resuspended into 1 L of BMM medium in a 5 L baffled flask and incubated in a 28° C. shaking incubator for 3 days. The cultures were induced at t=24 and 48 h. The expression medium was separated from cells by centrifugation (6000 rpm, 20 min). The medium was adjusted to pH 3.0 before it was applied to an SP Sepharose column (1 cm×1 cm, Amersham Biosciences) pre-equilibrated with 100 mM potassium phosphate buffer, pH 6.0. The column was then washed with 100 mL of 100 mM potassium phosphate buffer, pH 6.0 and bound protein was eluted in 10×10 mL of 100 mM potassium phosphate buffer containing 500 mM NaCl. Eluted proteins were concentrated down to 1 mL using a centrifugal column and washed 5× using sterile milli Q ultrapure water. The protein concentration of *Pichia*-expressed defensin was determined using the bicinchoninic acid (BCA) protein assay (Pierce Chemical Co.) with bovine serum albumin (BSA) as the protein standard.

Analysis of Antifungal Activity of Defensins

The inhibitory effects of each defensin on the growth of *Fusarium graminearum* (*Giberellazea*) (Fgr, Pioneer Hybrid International (PHI) isolate 73B1A), *Fusarium oxysporum* f. sp. *vasinfectum* (Fov, Australian isolate VCG01111 isolated from cotton; from Farming Systems Institute, Department of Agriculture, Fisheries & Forestry, Queensland, Australia) or *Colletotrichum graminicola* (Cgr, PHI isolate Carroll-1A-9), *Stenocarpella maydis* (DAR51549) (NSW Department of Primary Industries Agricultural Scientific Collections Trust (ASCU) or *Aspergillus niger* (from School of Molecular and Microbial Biosciences, University of Sydney, NSW, Australia) was measured essentially as described by Broekaert et al. (1990) *FEMS Microbiol Lett* 69:55-59.

Spores were isolated from sporulating fungus spp. growing on synthetic nutrient poor agar (Fgr), V8 agar (Cgr, Fve), ½ strength potato dextrose broth agar (Fov, *Aspergillus niger*), yeast extract peptone dextrose agar (*Candida albicans*, *Cryptococcus gattii*) or ½ strength Sabouraud dextrose agar (*Trichophyton interdigitale*, *Trichophyton rubrum*). Spores were removed from the plates by the addition of ½ strength potato dextrose broth (PDB). Spore concentrations were measured using a haemocytometer.

10× stock solutions of each defensin were prepared in sterile water. The Tecan liquid handling robot was used to serially dilute each defensin and transfer 20 µl of each concentration in triplicate to a 96 well microtitre plate. Spores were added to each plate, 80 µl 5×$10^4$ spores/ml in ½ strength PDB. The plates were incubated at 25° C. (Fgr, Cgr, Fve, Fov, *F. solani*, *S. maydis*, *Aspergillus niger*) or 30° C. (*C. albicans*, *C. gattii*, *T. interdigitale*, *T. rubrum*). Fungal growth was assayed by measuring optical density at 595 nm (A595) using a microtitre plate reader (SpectraMax Pro M2; Molecular Devices. Growth was allowed to proceed until the optical density (OD) of the fungus in the absence of any test defensin reached an OD of 0.2. Each test was performed in quadruplicate.

Permeabilization Assay

*Fusarium oxysporum* f. sp *vasinfectum* (Fov) or *Fusarium graminearum* (Fgr) were grown in half-strength PDB from a starting concentration of 5×$10^4$ spores/mL for 18 hours at 25° C. Hyphal suspension (90 µL) was then transferred to 96-well microtitre plates and incubated with SYTOX (Registered Trade Mark) green (0.5 µM) for 10 minutes prior to the addition of 10 µL of peptide solution to give final protein concentration, of 10 µM (Fov) or 5 (Fgr). SYTOX green uptake (indicating permeabilization) was quantified by measuring fluorescence using a microtitre plate reader (SpectraMax M5e; Molecular Devices) with excitation and emission wavelengths of 488 nm and 538 nm, respectively. Readings were taken every 2 minutes for 2 hours. Example results of a permeabilization assay are shown in FIG. 1 and Table 12a.

A relative permeability index is herein defined wherein the degree of permeabilisation of a fungal strain induced by a defined concentration of a defensin is addressed, relative to a value of 1.0 for NaD1 at the same concentration.

FIG. 1 illustrates the relative uptake of SYTOX green into Fov hyphae after treatment with 10 µM NaD1, HXP4, HXL002, HXL007, HXL008 and DmAMP1. See also Table 12a. The defensins NaD1, HXP4, HXL002, HXL007 and HXL008 were able to permeabilize Fov hyphae while the defensin DmAMP1 was not. The relative permeability index of each defensin is presented in Table 12a. For the purposes of this invention, defensins with a relative permeability index of greater than 0.2 on Fov are considered permeabilizing.

Figure 2:
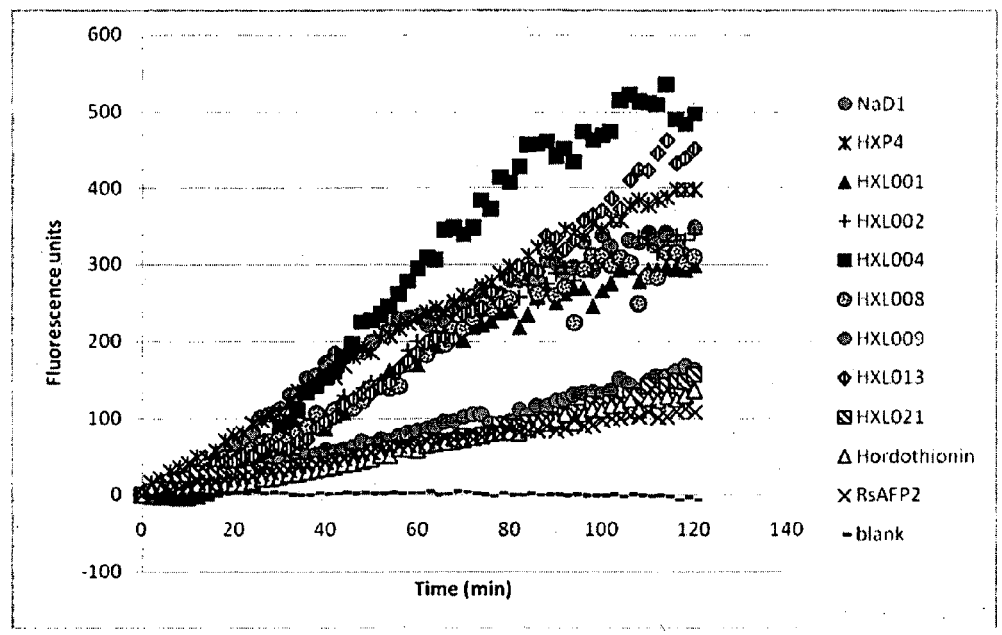
FIG. 2 is a graphical representation showing the results of a permeabilization assay on Fgr hyphae demonstrating the difference between permeabilizing (NaD1, HXP4, HXL002, HXL004, HXL008 and HXL013) and non-permeabilizing (Hordothionin, RsAFP2, HXL009 and HXL021) defensins.

FIG. 2 illustrates the relative uptake of SYTOX green into Fgr hyphae after treatment with 5 µM NaD1, HXP4, HXL001, HXL002, HXL004, HXL008, HXL009, HXL013, HXL021, Hordothionin and RsAFP2. The defensins NaD1, HXP4, HXL002, HXL004 and HXL008 caused significantly more permeabilisation of Fgr hyphae than the defensins HXL009, HXL021, hordothionin and RsAFP2. The relative permeability index of each defensin is presented in Table 12b. For the purposes of this invention, defensins with a relative permeability index of greater than 0.5 on Fgr are considered permeabilizing.

Production of Transgenic Plant Cells and/or Tissue

Techniques and agents for introducing and selecting for the presence of heterologous DNA in plant cells and/or tissue are well-known. Genetic markers allowing for the selection of heterologous DNA in plant cells are well-known, e.g. genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e. the chimeric gene containing nopaline synthetase promoter, Tn5 neomycin phosphotransferase II and nopaline synthetase 3' non-translated region described by Rogers et al. (1988) *Methods for Plant Molecular Biology*.

Techniques for genetically engineering plant cells and/or tissue with an expression cassette comprising an inducible promoter or chimeric promoter fused to a heterologous coding sequence and a transcription termination sequence are to be introduced into the plant cell or tissue by *Agrobacterium*-mediated transformation, electroporation, microinjection, particle bombardment or other techniques known to the art. The expression cassette advantageously further contains a marker allowing selection of the heterologous DNA in the plant cell, e.g. a gene carrying resistance to an antibiotic such as kanamycin, hygromycin, gentamicin, or bleomycin.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g. calcium phosphate coprecipitation, viral vectors, and other techniques practiced in the art. Suitable plant transformation vectors include those derived from a Ti plasmid of *Agrobacterium tumefaciens*, such as those disclosed by Herrera-Estrella et al. (1983) *EMBO J* 2:987-995; Bevan et al. (1983) *Nucleic Acids Res* 11(2):369-385; Klee et al. (1985) *Bio/Technology* 3:637-642 and EPO publication 120,516 (Schilperoort et al, European Patent Publication 120, 516). In addition to plant transformation vectors derived from the Ti or root-inducing (Ri) plasmids of *Agrobacterium*, alternative methods can be used to insert the DNA constructs of this invention into plant cells.

The choice of vector in which the DNA of interest is operatively linked depends directly, as is well known in the art, on the functional properties desired, e.g. replication, protein expression, and the host cell to be transformed, these being limitations inherent in the art of constructing recombinant DNA molecules. The vector desirably includes a prokaryotic replicon, i.e. a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT tmand pBS available from Stratagene (La Jolla, Calif.). A vector of the present invention may also be a Lambda phage vector as known in the art or a Lambda ZAP vector (available from Stratagene La Jolla, Calif.). Another vector includes, for example, pCMU (Nilsson et al. (1989) *Cell* 58:707). Other appropriate vectors may also be synthesized, according to known methods; for example, vectors pCMU/Kb and pCMUII used in various applications herein are modifications of pCMUIV (Nilsson et al. (1989) supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens*.

A transgenic plant can be produced by any standard means known to the art, including but not limited to *Agrobacterium tumefaciens*-mediated DNA transfer, preferably with a disarmed T-DNA vector, electroporation, direct DNA transfer, and particle bombardment. Techniques are well-known to the art for the introduction of DNA into monocots as well as dicots, as are the techniques for culturing such plant tissues and regenerating those tissues.

Synergy Classification

Synergy is classified as the difference between the observed % fungal growth inhibition caused by the combination of two defensins (Io value) and the expected % fungal growth inhibition of the two defensins based on the sum of the % fungal growth inhibition of each defensin on its own (Ee value calculated according to the Limpel formula used by Richer et al. (1987) supra). The difference, Io-Ee, is the synergy value. A synergy value up to 15 means no significant synergy; 15-30 is a low level of synergy; 30-60 is a medium level of synergy; and >60 is a high level of synergy.

Bioassay Method for In Planta Studies

Preparation of *C. graminicola* Inoculum

*Colletotrichum graminicola* (US isolate Carroll-1A-99) is isolated from *Zea maize* (Pioneer Hi-Bred International, Inc. Johnston, Iowa, USA). Spores are isolated from sporulating cultures grown on V8 agar for approximately 2-3 Weeks. *C. graminicola* spores are collected by scraping the surface of the plates in sterile water and separating spores from hyphal matter by filtration through facial tissue. The concentration of spores in the filtrate is measured using a haemocytometer.

Preparation of *F. graminearum* Inoculum

*Fusarium graminearum* isolate (73B1A) is isolated from *Zea maize* (Pioneer Hi-Bred International, Inc. Johnston, Iowa, USA). Spores are isolated from sporulating cultures grown on SNP agar for approximately 2-3 Weeks. *F. graminearum* spores are collected by scraping the surface of the plates in sterile water. The concentration of spores is measured using a haemocytometer.

Inoculation of Maize Plants

Plants for bioassay are grown in the glasshouse for approximately 8-10 weeks after deflasking.

*C. Gramincola* Inoculation

Two wounds, 2.0 mm in length are made on opposing sides of the maize leaf sheath and then overlaid with $1\times10^6$*C. graminicola* spores/mL. Wounds are then sealed with Glad Press'n'Seal for three days. The area of infection is measured by digital photography 10 days post inoculation.

*F. graminearum* Inoculation

Two wounds, 2.0 mm in length are made on opposing sides of the maize leaf sheath. Wounds are overlaid 6 mm diameter paper discs dipped in $1\times10^6$*F. graminearums* pores/mL. Wounds are then sealed with Glad Press'n'Seal for three days. The area of infection is measured by digital photography 10 days post inoculation.

Analysis of Transgene Expression in Corn Plants ELISA Method Protein extract: leaf sheaths are excised from plants grown in the glasshouse. The tissue (50 mg) is frozen in liquid nitrogen and ground in a mixer mill (Retsch MM300) for 2×15 seconds at frequency 30 s$^{-1}$. Protein extracts are made by adding 450 μL 2% insoluble PVPP (Polyclar)/PBS/ 0.05% v/v Tween 20 and vortexing for 20 seconds. The samples are centrifuged for 10 minutes and the supernatant is collected.

ELISA plates (NuncMaxisorp #442404) are incubated with 100 μL/well of primary antibody in PBS (100 ng/well of anti-defensin antibody). Plates are incubated overnight at 4° C. in a humid box. They are then washed for 2 minutes×4 with PBS/0.05% v/v Tween 20. Plates are blocked with 200 μL/well 3% w/v BSA (Sigma A-7030: 98% ELISA grade) in PBS and incubated for 2 hours at 25° C. Plates are then washed for 2 minutes×4 with PBS/0.05% v/v Tween 20.

Corn sheath protein extracts (100 μL/well diluted in PBS/0.05% v/v Tween 20) are then applied to the plates which are then incubated for 2 hours at 25° C. Plates are then washed for 2 minutes×4 with PBS/0.05% v/v Tween 20 and then 100 μL/well of secondary antibody in PBS (e.g. 75 ng/well biotin-labeled defensin antibody) is applied. The biotin labeled antibody is prepared using the EZ-link Sulfo-NHS-LC-biotinylation kit (Pierce); 2 mL of protein A purified antibody and 2 mg of the biotin reagent are used. Plates are incubated for 1 hour at 25° C. and then washed for 2 minutes×4 with PBS/0.05% v/v Tween 20 and 100 μL/well of NeutriAvidin HRP-conjugate (Pierce #31001; 1:1000 dilution; 0.1 μL/well) in PBS is applied. The plates are incubated for 1 hour at 25° C. and then washed for 2 minutes×2 with PBS/0.05% v/v Tween 20, followed by 2 minutes×2 with H$_2$O. Just before use, the substrate is prepared by dissolving 1 ImmunoPure OPD tablet (Pierce #34006) in 9 mL H$_2$O, then adding 1 mL stable peroxide buffer (10×, Pierce #34062). The substrate is applied at 100 μL/well and plates are incubated at 25° C. until color develops. The reaction is stopped by applying 50 μL 2.5 M sulfuric acid. Absorbance at 490 nm is measured in a plate reader (Molecular Devices).

Example 1

Inhibition of the Growth of Fungal Pathogens in, the Presence of a Permeabilizing Defensin and a Class I Defensin In Vitro The inhibitory effects of a permeabilizing defensin in combination with a Class I defensin on the growth of *Fusarium graminearum* (*Giberellazea*) (Fgr, Pioneer Hybrid International (PHI) isolate 73B1A), *Fusarium oxysporum* f. sp. *vasinfectum* (Fov, Australian isolate VCG01111 isolated from cotton; from Farming Systems Institute, Department of Agriculture, Fisheries & Forestry, Queensland, Australia), *Fusarium solani* (from School of Botany, University of Melbourne, Victoria, Australia), *Colletotrichum graminicola* (Cgr, PHI isolate Carroll-1A-9), *Stenocarpella maydis* (DAR51549) (NSW Department of Primary Industries Agricultural Scientific Collections Trust (ASCU) *Aspergillus niger* (from School of Molecular and Microbial Biosciences, University of Sydney, NSW, Australia), *Candida albicans* (isolate DAY185, Department of Biochemistry and Molecular Biology, Monash University, Victoria, Australia), *Cryptococcus gattii* (isolate BAL11), *Trychophyton interdigitale* or *Trychophyton rubrum* (both obtained from the National Mycology. Reference Centre, South Australia Pathology at the Women's and Children's Hospital, Adelaide, Australia) was measured essentially as described by Broekaert et al. (1990) supra.

Spores were isolated from sporulating fungus spp. growing on synthetic nutrient poor agar (Fgr), V8 agar (Cgr), ½ strength potato dextrose broth agar (Fov. *Aspergillus niger*), yeast extract peptone dextrose agar (*Candida albicans, Cryptococcus gattii*) or ½ strength Sabouraud dextrose agar (*Trichophyton interdigitale, Trichophyton rubrum*). Spores were removed from the plates by the addition of ½ strength potato dextrose broth (PDB). Spore concentrations were measured using a haemocytometer.

Antifungal assays were conducted in 96 well microtitre plates essentially as described in the detailed description (Analysis of antifungal activity of defensins). Wells were loaded with 10 μL of filter sterilized (0.22 μm syringe filter, Millipore) defensin 1 (10× stock for each final concentration) or water, 10 μL of filter sterilized (0.22 μm syringe filter, Millipore) defensin 2 (10× stock for each final concentration) or water and 80 μL of 5×10$^4$ spores/mL in ½ strength PDB. The plates were incubated at 25° C. (Fgr, Cgr, Fov, *F. solani, S. maydis, Aspergillus niger*) or 30° C. (*C. albicans, C. gattii, T. interdigitale, T. rubrum*). Fungal growth was assayed by measuring optical density at 595 nm (A595) using a microtitre plate reader (SpectraMax Pro M2; Molecular Devices. Growth was allowed to proceed until the optical density (OD) of the fungus in the absence of any test defensin reached an OD of 0.2. Each test was performed in duplicate.

Synergy is classified as the difference between the observed % fungal growth inhibition caused by the combination of two defensins (Io value) and the expected % fungal growth inhibition of the two defensins based on the sum of the % fungal growth inhibition of each defensin on its own (Ee value calculated according to the Limpel formula used by Richer et al. (1987) supra). The difference, Io-Ee, is the synergy value. A synergy value up to 15 means no significant synergy; 15-30 is a low level of synergy; 30-60 is a medium level of synergy; and >60 is a high level of synergy. Synergy calculations are presented in Tables 3 through 11 wherein, as indicated above, Ee is the expected effect from the additive response according to Limpel's formula expressed as percent inhibition and Io is the percent inhibition observed. Synergy occurs when Io values are higher than Ee values.

Results

The results are shown in Tables 3 through 11.

Example 2

In Planta Synergy of IMP 4 with SBI6 Against *Fusarium graminearum* and *Colletotrichum graminicola*

Transgenic corn plants are produced by *Agrobacterium*-mediated transformation or particle bombardment using standard protocols such as those described in U.S. Pat. No. 5,981,840; U.S. Pat. No. 7,528,293; U.S. Pat. No. 7,589,176; U.S. Pat. No. 7,785,828; Frame et al. (2002) *Plant Physiology* 129:13-22. A binary vector containing GAT as the selectable marker, a ubiquitin promoter for constitutive expression and a codon optimized sequence encoding either HXP4, SBI6 or HXP4+SBI6 (via a double expression vector) is transferred into an *Agrobacterium tumefaciens* strain by electroporation. Immature corn embryos are infected via immersion in a suspension of *Agrobacterium* followed by a period of co-culture on a solid medium. The embryos are then optionally "rested" during which time they are incubated in the presence of at least one antibiotic which inhibits the growth of *Agrobacterium*. Next, transformed callus is obtained by culturing the infected embryos on solid medium containing glyphosphate which inhibits the growth of non-transformed cells. Transformed callus is then able to be regenerated into plants using standard methods. Plants expressing both HXP4 and SBI6 may also be generated via a cross of individual events.

Levels of HXP4 and SBI6 expression in PCR positive plants are determined, for example, by ELISA screening (see Methods). Plants expressing HXP4>10 ppm and/or SBI6 at >0.9 ppm are assessed for increased resistance to *Fusarium graminearum* and *Colletotrichum graminicola* using the bioassay described in the Methods.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

*Fusarium graminearum*

| Permeabilizing defensin | Class I defensin | Expected inhibition | Observed inhibition | Synergy |
|---|---|---|---|---|
| NaD1 (0.5 μM) | Hordothionin (2 μM) | 26.3 | 93 | 66.7 |
| | Zeathionin-2 (2 μM) | 36.3 | 86.2 | 49.9 |
| | PsD1 (2 μM) | 0 | 75.5 | 75.5 |
| | HXL004 (2 μM) | 18.6 | 70.5 | 51.9 |
| | HXL001 (0.5 μM) | 54.0 | 100.0 | 46.0 |
| | SBI6 (2 μM) | 0 | 80.3 | 80.3 |
| | HXL008 (0.5 μM) | 0 | 91.5 | 91.5 |
| | HXL009 (1 μM) | 0 | 72.3 | 72.3 |
| | HXL012 (1 μM) | 16.7 | 93.4 | 76.7 |
| | HXL015 (0.25 μm) | 0 | 44.7 | 44.7 |
| | HXL021 (0.3 μM) | 4.9 | 70.4 | 65.5 |
| | RsAFP2 (0.125 μM) | 21.5 | 67.2 | 45.7 |
| | HXL002 (0.5 μM) | 39.2 | 93.3 | 54.0 |
| NaD1 (0.25 μM) | SBI6 (0.5 μM) | 21.5 | 52.1 | 30.5 |
| HXP4 (0.125 μM) | Hordothionin (1 μM) | 18.4 | 90.3 | 71.9 |
| | Zeathionin-2 (1 μM) | 12.7 | 85.4 | 72.7 |
| | SBI6 (2 μM) | 22.5 | 87.2 | 64.7 |
| | VP45 (0.5 μM) | 11.2 | 93.3 | 82.1 |
| | SBI6 (1 μM) | 19.3 | 90.8 | 71.5 |
| | HXL008 (0.25 μM) | 34.5 | 97.8 | 63.3 |
| | HXL009 (0.25 μM) | 33.4 | 93.1 | 59.7 |
| | HXL012 (0.25 μM) | 49.6 | 92.5 | 42.9 |
| | HXL015 (0.125 μm) | 41.9 | 91.3 | 49.4 |
| | HXL021 (0.125 μM) | 38.8 | 90.4 | 51.6 |
| | RsAFP2 (0.125 μM) | 58.8 | 89.9 | 31.1 |
| HXP4 (0.125 μM) | HXL012 (0.5 μM) | 8.4 | 80.7 | 72.3 |
| | HXL015 (1 μM) | 17 | 94.2 | 77.2 |
| TPP3 (0.2 μM) | Hordothionin (1 μM) | 5.9 | 85.9 | 80 |
| | PHI-004 (2 μM) | 0 | 67 | 67 |
| | SBI6 (1 μM) | 16.2 | 68.6 | 52.4 |
| HXL001 (0.5 μM) | Hordothionin (4 μM) | 17.7 | 78.9 | 61.2 |
| | HXL004 (4 μM) | 6.1 | 69.4 | 63.3 |
| | HXL010 (4 μM) | 14.2 | 60 | 45.8 |
| | Zeathionin-2 (4 μM) | 3.2 | 43.2 | 40 |
| HXL001 (1 μM) | HXL015 (0.5 μM) | 10 | 93.9 | 83.9 |
| | HXL021 (0.25 μM) | 7.6 | 91.5 | 83.9 |
| HXL007 (0.5 μM) | Hordothionin (4 μM) | 20.8 | 74.3 | 53.5 |
| | HXL004 (4 μM) | 4.9 | 67.2 | 62.3 |
| | HXL010 (4 μM) | 12.7 | 62.2 | 49.5 |
| | Zeathionin-2 (4 μM) | 9.9 | 54.4 | 44.5 |
| HXL008 (0.5 μM) | Hordothionin (4 μM) | 14.9 | 74.6 | 59.7 |
| HXL004 (0.5 μM) | HXL012 (1 μM) | 0 | 55.2 | 55.2 |
| | HXL015 (1 μM) | 12 | 98.3 | 86.3 |
| | HXL008 (0.5 μM) | 28.2 | 73.6 | 45.4 |

TABLE 3-continued

*Fusarium graminearum*

| Permeabilizing defensin | Class I defensin | Expected inhibition | Observed inhibition | Synergy |
|---|---|---|---|---|
| | HXL009 (2 μM) | 37.8 | 60.2 | 22.4 |
| | SBI6 (4 μM) | 4.1 | 82.5 | 78.4 |

TABLE 4

*Colletotrichum graminicola*

| Permeabilizing defensin | Class I defensin | Expected inhibition | Observed inhibition | Synergy |
|---|---|---|---|---|
| NaD1 (1.25 μM) | SBI6 (0.5 μM) | 24.7 | 92.1 | 67.4 |
| | HXL008 (2 μM) | 14.3 | 46.3 | 32.0 |
| NaD1 (5 μM) | Hordothionin (4 μM) | 0 | 80.6 | 80.6 |
| | Zeathionin-2 (4 μM) | 19.5 | 81.6 | 62.1 |
| | DmAMP1 (2 μM) | 13.9 | 61.1 | 47.2 |
| HXP4 (1.25 μM) | HXL008 (2 μM) | 19.9 | 77.0 | 57.1 |
| | HXL009 (2 μM) | 9.5 | 38.3 | 28.8 |
| HXP4 (2.5 μM) | Hordothionin (2 μM) | 11.3 | 41.9 | 30.6 |
| | Zeathionin-2 (2 μM) | 8.4 | 21.1 | 12.7 |
| | SBI6 (2 μM) | 22.5 | 87.2 | 64.7 |
| | PsD1 (4 μM) | 29.9 | 50.9 | 21 |
| PhD2 (5 μM) | Hordothionin (2 μM) | 42.2 | 70.8 | 28.6 |
| | Zeathionin-2 (2 μM) | 35.5 | 55.5 | 20 |
| TPP3 (2 μM) | Hordothionin (1 μM) | 0 | 86.3 | 86.3 |
| | HXL004 (2 μM) | 6.9 | 51.9 | 45 |
| | SBI6 (1 μM) | 0 | 28.7 | 28.7 |
| HXL008 (2.5 μM) | Hordothionin (2 μM) | 6.3 | 95.4 | 89.1 |
| | HXL004 (4 μM) | 0 | 76.4 | 76.4 |
| | HXL010 (4 μM) | 13 | 46.6 | 33.6 |
| | Zeathionin-2 (4 μM) | 1.5 | 29.7 | 28.2 |
| HXL001 (2.5 μM) | Hordothionin (2 μM) | 0 | 59.8 | 59.8 |
| | HXL004 (4 μM) | 2.6 | 44.7 | 42.1 |
| HXL002 (2.5 μM) | HXL008 (4 μM) | 20.9 | 84.6 | 63.7 |
| | HXL012 (1 μM) | 39.4 | 86.4 | 47 |
| | SBI6 (4 MM) | 43.5 | 84.8 | 41.3 |
| | RsAFP2 (4 μM) | 8.4 | 57.9 | 49.5 |
| HXL004 (1.25 μM) | Hordothionin (2 μM) | 21 | 57.6 | 36.6 |
| | RsAFP2 (4 μM) | 20.9 | 66.9 | 46 |
| | HXL008 (1 μM) | 26.5 | 87.8 | 61.3 |
| | HXL012 (1 μM) | 30.7 | 79.7 | 49 |
| | SBI6 (2 μM) | 10.1 | 55.3 | 45.2 |
| | HXL015 (2 μM) | 44.5 | 80.1 | 35.6 |

TABLE 5

*Fusarium solani*

| Permeabilizing defensin | Class I defensin | Expected inhibition | Observed inhibition | Synergy |
|---|---|---|---|---|
| HXP4 (0.125 μM) | SBI6 (2 μM) | 0 | 81.4 | 81.4 |

TABLE 6

*Aspergillus niger*

| Permeabilizing defensin | Class I defensin | Expected inhibition | Observed inhibition | Synergy |
|---|---|---|---|---|
| NaD1 (3 μM) | SBI6 (2 μM) | 31.9 | 93.8 | 61.9 |

TABLE 7

*Stenocarpella maydis*

| Permeabilizing defensin | Class I defensin | Expected inhibition | Observed inhibition | Synergy |
|---|---|---|---|---|
| HXP4 (1.25 μM) | SBI6 (2 μM) | 44.2 | 78.9 | 34.7 |

TABLE 8

*Candida albicans*

| Permeabilizing defensin | Class I defensin | Expected inhibition | Observed inhibition | Synergy |
|---|---|---|---|---|
| NaD1 (4 μM) | HXL008 (4 μM) | 43 | 95.3 | 52.3 |
| | HXL009 (4 μM) | 46 | 97.6 | 51.6 |
| | SBI6 (1 μM) | 18.4 | 93 | 74.6 |
| | HXL021 (4 μM) | 24.3 | 87.6 | 63.3 |
| NaD1 (2 μM) | HXL012 (1 μM) | 26.4 | 94.3 | 67.9 |
| | HXL015 (2 μM) | 11.9 | 99.3 | 87.4 |
| | Hordothionin (4 μM) | 0.7 | 87.9 | 87.2 |
| | RsAFP2 (4 μM) | 12.2 | 43.6 | 31.4 |
| HXP4 (2 μM) | HXL008 (4 μM) | 23.4 | 100 | 76.6 |
| | HXL009 (4 μM) | 0 | 83.4 | 83.4 |
| | HXL012 (0.5 μM) | 0 | 98.6 | 98.6 |
| | SBI6 (2 μM) | 0 | 96.5 | 96.5 |
| | HXL015 (1 μM) | 7.8 | 98.8 | 91 |
| | Hordothionin (2 μM) | 13.2 | 91 | 77.8 |
| | RsAFP2 (4 μM) | 38.1 | 74.8 | 36.7 |
| | HXL021 (4 μM) | 0 | 76.5 | 76.5 |
| HXL001 (4 μM) | HXL008 (4 μM) | 16.3 | 92.8 | 76.5 |
| | HXL009 (4 μM) | 20.7 | 51.2 | 30.5 |
| | HXL012 (1 μM) | 15.5 | 94.4 | 78.9 |
| | SBI6 (2 μM) | 35.8 | 97.6 | 61.8 |
| | HXL015 (2 μM) | 50.2 | 100 | 49.8 |
| | Hordothionin (2 μM) | 23.9 | 82.7 | 58.8 |
| | RsAFP2 (4 μM) | 34.5 | 95.5 | 61 |
| | HXL021 (4 μM) | 34.6 | 87.9 | 53.3 |
| HXL002 (4 μM) | HXL008 (4 μM) | 6.5 | 93 | 86.5 |
| | HXL012 (1 μM) | 26.4 | 100 | 73.6 |
| | SBI6 (2 μM) | 48.2 | 86 | 37.8 |
| | HXL015 (2 μM) | 18.6 | 100 | 81.4 |
| | Hordothionin (2 μM) | 7.3 | 80 | 72.7 |
| | RsAFP2 (4 μM) | 11.8 | 87.8 | 76 |
| | HXL021 (4 μM) | 15.4 | 79.3 | 63.9 |
| HXL004 (2 μM) | HXL008 (4 μM) | 24 | 87.2 | 63.2 |
| | HXL012 (1 μM) | 1 | 85.4 | 84.4 |
| | SBI6 (2 μM) | 0 | 79.6 | 79.6 |
| | HXL015 (2 μM) | 20.1 | 90 | 69.9 |
| | Hordothionin (4 μM) | 3.3 | 89.7 | 86.4 |
| | RsAFP2 (4 μM) | 23 | 87.6 | 64.6 |
| | HXL021 (4 μM) | 0 | 82.2 | 82.2 |

TABLE 9

*Cryptococcus gattii*

| Permeabilizing defensin | Class I defensin | Expected inhibition | Observed inhibition | Synergy |
|---|---|---|---|---|
| NaD1 (1 μM) | HXL008 (2 μM) | 52.8 | 100 | 47.2 |
| | HXL009 (2 μM) | 47.4 | 99.5 | 52.1 |
| | HXL012 (1 μM) | 34.7 | 99.3 | 64.6 |
| | SBI6 (2 μM) | 6.5 | 88.8 | 82.3 |
| | HXL015 (1 μM) | 41.8 | 75.5 | 67.9 |
| | Hordothionin (4 μM) | 66.4 | 88.2 | 21.8 |
| HXP4 (0.5 μM) | HXL008 (2 μM) | 47.7 | 99 | 51.3 |
| | HXL009 (1 μM) | 49.4 | 100 | 50.6 |
| | HXL012 (0.5 μM) | 26.3 | 99 | 72.7 |
| | SBI6 (2 μM) | 34.2 | 95.2 | 61 |
| | Hordothionin (2 μM) | 23.8 | 69.4 | 45.6 |
| | RsAFP2 (4 μM) | 53.8 | 100 | 46.2 |
| HXL001 (1 μM) | HXL012 (1 μM) | 15.8 | 95.8 | 80 |
| HXL002 (1 μM) | HXL008 (4 μM) | 8.6 | 100 | 91.4 |
| | HXL009 (2 μM) | 29.9 | 84.6 | 54.7 |
| | HXL012 (1 μM) | 23.1 | 100 | 76.9 |
| | SBI6 (2 μM) | 18.8 | 91.9 | 73.1 |
| | HXL015 (1 μM) | 0 | 100 | 100 |
| | Hordothionin (2 μM) | 12.4 | 97.7 | 85.3 |
| | RsAFP2 (4 μM) | 26.3 | 85.2 | 58.9 |
| | HXL021 (2 μM) | 29.2 | 58 | 28.8 |
| HXL004 (1 μM) | HXL008 (2 μM) | 0.5 | 71 | 70.5 |
| | HXL012 (1 μM) | 26.5 | 97.3 | 70.8 |
| | SBI6 (2 μM) | 33 | 87 | 54 |
| | HXL015 (1 μM) | 0 | 99 | 99 |
| | Hordothionin (2 μM) | 8 | 62.9 | 54.9 |
| | HXL021 (2 μM) | 11.1 | 90.5 | 79.4 |

TABLE 10

*Trichophyton interdigitale*

| Permeabilising defensin | Class I defensin | Expected inhibition | Observed inhibition | Synergy |
|---|---|---|---|---|
| HXP4 (0.5 μM) | Hordothionin (2 μM) | 51.9 | 87.1 | 35.2 |
| | HXL008 (0.25 μM) | 34.7 | 67.7 | 33.0 |
| NaD1 (0.5 μM) | Hordothionin (1 μM) | 9.8 | 33.7 | 23.9 |
| | HXL009 (0.5 μM) | 28 | 61.2 | 33.2 |
| | HXL008 (0.25 μM) | 29.7 | 72.6 | 42.9 |
| | HXL004(1 μM) | 22.2 | 56.2 | 34.0 |
| HXL001 (0.5 μM) | RsAFP2 (0.5 μM) | 5.9 | 30.6 | 24.7 |
| | Hordothionin(2 μM) | 48 | 76.5 | 28.5 |
| HXL001 (1 μM) | HXL008(0.25 μM) | 10.6 | 51.6 | 41.0 |
| HXL002 (0.5 μM) | Hordothionin(2 μM) | 50.2 | 85.3 | 35.1 |
| | HXL008(0.25 μM) | 27.7 | 69.7 | 42.0 |
| HXL004 (1 μM) | Hordothionin(2 μM) | 57.5 | 93.6 | 36.1 |
| | HXL008(0.25 μM) | 23.0 | 70.4 | 47.4 |

TABLE 11

*Trichophyton rubrum*

| Permeabilizing defensin | Class I defensin | Expected inhibition | Observed inhibition | Synergy |
|---|---|---|---|---|
| NaD1 (1 μM) | HXL009 (2 μM) | 50.8 | 70.2 | 19.4 |
| HXL004 (1 μM) | HXL008 (0.25 μM) | 18.3 | 51.7 | 33.4 |

TABLE 12a

| Defensin | Permeability index | |
|---|---|---|
| HXL007 | 1.2 | 350 |
| NaD1 | 1.0 | 300 |
| HXL002 | 0.9 | 260 |
| HXL008 | 0.8 | 225 |
| HXP4 | 0.7 | 220 |
| DmAMP1 | 0.0 | 0 |

TABLE 12b

| Defensin | Permeability index | |
|---|---|---|
| HXL004 | 1.6 | 500 |
| HXL013 | 1.4 | 450 |
| HXP4 | 1.3 | 400 |
| NaD1 | 1.0 | 320 |
| HXL002 | 1.0 | 320 |

TABLE 12b-continued

| Defensin | Permeability index | |
|---|---|---|
| HXL001 | 0.9 | 300 |
| HXL008 | 0.9 | 300 |
| HXL021 | 0.5 | 150 |
| HXL009 | 0.4 | 120 |
| Hordothionin | 0.4 | 120 |
| RsAFP2 | 0.3 | 100 |

BIBLIOGRAPHY

Alexander et al. (1993) *Proc Natl Acad Sci USA* 90:7327-7331
Allison et al. (1986); MDMV leader (Maize Dwarf Mosaic Virus); *Virology* 154:9-20
Almeida et al. (2000) *Arch Biochem Biophys* 378:278-286, 2000
Balandin et al. (2005) *Plant Mol Biol* 58:269-282
Ballas et al. (1989) *Nucleic Acids Res.* 17:7891-7903
Bevan et al. (1983) *Nucleic Acids Res* 11(2):369-385
Broekaert et al. (1990) *FEMS Microbiol Lett* 69:55-59
Bytebier et al. (1987) *Proc. Natl. Acad. Sci. USA* 84:5345-5349
Campbell and Gowri (1990) *Plant Physiol.* 92:1-11
Castro et al. (1996) *Protein Pept. Lett.* 3:267-274
Chen et al. (2005) *J Agric Food Chem* 53:982-988
Christopherson et al. (1992) *Proc. Natl. Acad. Sci. USA* 89:6314-6318
Christensen et al. (1989) *Plant Mol. Biol.* 12:619-632
Christensen et al. (1992) *Plant Mol. Biol.* 18:675-689
Christou et al. (1988) *Plant Physiol.* 87:671-674
Christou and Ford (1995) *Annals of Botany* 75:407-413
Crossway et al. (1986) *Biotechniques* 4:320-334
D'Halluin et al. (1992) *Plant Cell* 4:1495-1505
Datta et al. (1990) *Biotechnology* 8:736-740
De Wet et al. (1985) in *The Experimental Manipulation of Ovule Tissues*, ed. Chapman et al. (Longman, N.Y.), pp. 197-209
Della-Cioppa et al. (1987) *Plant Physiol.* 84:965-968
Elroy-Stein et al. (1989) *PNAS USA* 86:6126-6130
Finer and McMullen (1991) In *Vitro Cell Dev. Biol.* 27P:175-182
Frame et al. (2002) *Plant Physiology* 129:13-22
Fromm et al. (1990) *Biotechnology* 8:833-839
Gallie et al. (1989) In *Molecular Biology of RNA*, ed. Cech (Liss, New York), pp. 237-256
Gorlach et al. (1996) *Plant Cell* 8:629-643
Greco et al. (1995) *Pharmacol Rev* 47:331-385
Guerineau et al. (1991) *Mol. Gen. Genet.* 262:141-144
Hanks et al. (2005) *Plant Mol Biol* 58:385-399
Herrera-Estrella et al. (1983) *EMBO J* 2:987-995
Hooykaas-Van Slogteren et al. (1984) *Nature* (London) 311:763-764
Ishida et al. (1996) *Nature Biotechnology* 14:745-750
Jobling et al. (1987) *Nature* 325:622-625
Joshi et al. (1987) *Nucleic Acid Res.* 15:9627-9639
Kaeppler et al. (1990) *Plant Cell Reports* 9:415-418
Kaeppler et al. (1992) *Theor. Appl. Genet.* 84:560-566
Klee et al. (1985) *Bio/Technology* 3:637-642
Klein et al. (1988) *Biotechnology* 6:559-563
Klein et al. (1988) *Proc. Natl. Acad. Sci. USA* 85:4305-4309
Klein et al. (1989) *Plant Physiol.* 91:440-444
Last et al. (1991) *Theor. Appl. Genet.* 81:581-588
Lay et al. (2003) *J Mol Biol* 325:175-188
Li et al. (1993) *Plant Cell Reports* 12:250-255
Lin et al. (2007) *Proteins* 68:530-540
Lommel et al. (1991) *Virology* 81:382-385
Macejak et al. (1991) *Nature* 353:90-94
Madala et al. (2010) *Chem Rv* 110(6):1-31
McCabe et al. (1988) *Biotechnology* 6:923-926
McElroy et al. (1990) *Plant Cell* 2:163-171
Mendez et al. (1990) *Eur. J. Biochem.* 194:533-539
Milligan and Gasser (1995) *Plant Mol. Biol.* 28:691-711
Mogen et al. (1990) *Plant Cell* 2:1261-1272
Munroe et al. (1990) *Gene* 91:151-158
Murray et al. (1989) *Nucleic Acids Res.* 17:477-498
Nilsson et al. (1989) *Cell* 58:707
Odell et al. (1985) *Nature* 313:810-812
Oerke and Dehne (2004) *Crop Protection* 23:275-285
Osborn et al. (1995) *FEBS Lett* 368: 257-262
Paszkowski et al. (1984) *EMBO J.* 3:2717-2722
Proudfoot (1991) *Cell* 64:671-674
Richer et. al. (1987) *Pestic Sci* 19:309-315
Riggs et al. (1986) *Proc. Natl. Acad. Sci. USA* 83:5602-5606
Rogers et al. (1988) *Methods for Plant Molecular Biology*
Sagaram et al. (2011) *PLoS One* 6(4):e18550
Sanfacon et al. (1991) *Genes Dev.* 5:141-149
Sanford et al. (1987) *Particulate Science and Technology* 5:27-37
Singh et al. (1998) *Theor. Appl. Genet.* 96:319-324
Schilperoort et al. European Patent Office Publication 120, 516
Spelbrink et al. (2004) *Plant Physiol* 135:2055-2067
Terras et al. (1992) *J Biol Chem* 267:15301-15309
Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin)
Turk and Bode (1991) *FEBS Lett.* 285:213-219
Uknes (1993) *Molecular Plant Microbe Interactions* 6:680-685
Velten et al. (1984) *EMBO J* 3:2723-2730
Weising et. al. (1988) *Ann. Rev. Genet.* 22:421-477
Yarranton (1992) *Curr. Opin. Biotech.* 3:506-511

The invention claimed is:

1. A method for treating fungal pathogen infection of a subject, said method comprising providing cells of said subject with a Class I defensin, wherein the Class I defensin has a mature domain comprising an amino acid sequence selected from the group consisting of SEQ ID NOs: 85, 3, 6, 12, 24, 27, 36, 39 and 45, and a permeabilizing defensin having a mature domain selected from the group consisting of NaDI, TPP3, PhD1A, PhD2, NoD173, SEQ ID NOs: 3, 6, 12, 24, 70, 71 and 72, wherein the Class I defensin and the permeabilizing defensin are not the same.

2. The method of claim 1, wherein the subject is a plant.

3. The method of claim 2, wherein the Class I defensin and permeabilizing defensin are produced by a genetically modified plant cell or both defensins are applied topically to the plant or via the plant's root system or as a seed coating or as a surface spray.

4. The method of claim 1, further comprising providing the cell of said subject with a proteinase inhibitor or precursor form thereof.

5. The method of claim 1, wherein the fungal pathogen is selected from the group consisting of *Fusarium graminearum, Colletotrichum graminicola, Leptosphaeria maculans, Alternaria brassicicola, Alternaria alternata, Aspergillus nidulans, Botrytis cinerea, Cercospora beticola, Cercospora zeae maydis, Cochliobolus heterostrophus, Exserohilum turcicum, Fusarium culmorum, Fusarium oxysporum, Fusarium solani, Fusarium pseudograminearum, Fusarium verticilloides, Gaeumannomyces graminis* var. *tritici, Plasmodiophora brassicae, Sclerotinia sclerotiorum, Stenocarpella maydis, Thielaviopsis basicola, Verticillium dahliae, Ustilago zeae, Puccinia sorghi, Macrophomina phaseolina, Phialophora gregata, Diaporthe phaseolorum, Cercospora sojina, Phytophthora sojae, Rhizoctonia solani, Phakopsora pachyrhizi, Alternaria macrospora, Cercospora gossypina, Phoma exigua, Puccinia schedonnardii, Puccinia cacabata, Phymatotrichopsis omnivora, Fusarium avenaceum, Alternaria brassicae, Alternaria raphani, Erysiphe graminis, Septoria tritici, Septoria nodorum, Mycosphaerella zeae, Rhizoctonia cerealis, Ustilago tritici, Puccinia graminis, Puccinia triticina, Tilletia indica, Tilletia caries,* and *Tilletia controversa, Aspergillus niger, Candida, Cryptococcus, Trichophyton interdigitale* and *Trichophyton rubrum*.

6. The method of claim 2, wherein the plant is a crop plant selected from the group consisting of a forage crop, oilseed crop, grain crop, fruit crop, vegetable crop, fiber crop, spice crop, nut crop, turf crop, sugar crop, beverage crop and a forest crop.

7. The method of claim 6, wherein the crop plant is selected from the group consisting of soybean, canola, corn, cotton and wheat.

8. The method of claim 2, wherein the Class I defensin and permeabilizing defensin are applied as a seed coating.

9. The method of claim 1, wherein the subject is a human or non-human animal.

10. The method of claim 9, wherein the Class I defensin and permeabilizing defensin are applied topically to the human or non-human subject.

11. The method of claim 1, wherein the Class I defensin has a mature domain selected from the group consisting of SEQ ID NOs:6, 12, 24, 27, 36 and 45, and the permeabilizing defensin has a mature domain comprising an amino acid sequence selected from the group consisting of SEQ ID NOs:6, 12, 24 and 70.

12. The method of claim 4, wherein the proteinase inhibitor is a cystatin.

13. The method of claim 5, wherein the *Fusarium oxysporum* is selected from the group consisting of *Fusarium oxysporum* f. sp. *vasinfectum, Fusarium oxysporum* f. sp. *dianthi* and *Fusarium oxysporum* f. sp. *lycopersici*.

* * * * *

SEQUENCE LISTING

```
<160> NUMBER OF SEQ ID NOS: 98

<210> SEQ ID NO 1
<211> LENGTH: 504
<212> TYPE: DNA
<213> ORGANISM: artificial
<220> FEATURE:
<223> OTHER INFORMATION: HXL001 Zea mays na
<220> FEATURE:
<221> NAME/KEY: misc_feature
```

```
<222> LOCATION: (11)..(11)
<223> OTHER INFORMATION: n = A, T, C or G
<220> FEATURE:
<221> NAME/KEY: misc_feature
<222> LOCATION: (14)..(14)
<223> OTHER INFORMATION: n = A, T, C or G
<220> FEATURE:
<221> NAME/KEY: CDS
<222> LOCATION: (120)..(359)
<220> FEATURE:
<221> NAME/KEY: misc_feature
<222> LOCATION: (454)..(454)
<223> OTHER INFORMATION: n = A, T, C or G
<220> FEATURE:
<221> NAME/KEY: misc_feature
<222> LOCATION: (462)..(462)
<223> OTHER INFORMATION: n = A, T, C or G
<220> FEATURE:
<221> NAME/KEY: misc_feature
<222> LOCATION: (477)..(477)
<223> OTHER INFORMATION: n = A, T, C or G
<220> FEATURE:
<221> NAME/KEY: misc_feature
<222> LOCATION: (494)..(494)
<223> OTHER INFORMATION: n = A, T, C or G
<220> FEATURE:
<221> NAME/KEY: misc_feature
<222> LOCATION: (502)..(502)
<223> OTHER INFORMATION: n = A, T, C or G

<400> SEQUENCE: 1
cgtccaccat nctngtcgtt aggacgtaag gtaagacacc caggggcgag ccagtgagta      60
cagagagtag ccttacgtag cgaagctcag agcaagcgag ggtacggtca aggggggtg     119 atg gcg ctg tct cga cgt atg gcg gct ccc gtc ctc gtc ctc atg ctc     167
Met Ala Leu Ser Arg Arg Met Ala Ala Pro Val Leu Val Leu Met Leu
1               5                   10                  15 ctc ctc gtc gcc aca gag ctg ggg acg acc aag gtg gcg gag gcg agg     215
Leu Leu Val Ala Thr Glu Leu Gly Thr Thr Lys Val Ala Glu Ala Arg
            20                  25                  30 cac tgc ctg tcg cag agc cac cgg ttc aag ggc ctg tgc atg agc agc     263
His Cys Leu Ser Gln Ser His Arg Phe Lys Gly Leu Cys Met Ser Ser
        35                  40                  45 aac aac tgc gcc aac gtg tgc cag acc gag aac ttc ccc ggc ggc gag     311
Asn Asn Cys Ala Asn Val Cys Gln Thr Glu Asn Phe Pro Gly Gly Glu
    50                  55                  60 tgc aag gcg gag ggc gcc acg cgc aag tgc ttt tgc aag aag ata tgc     359
Cys Lys Ala Glu Gly Ala Thr Arg Lys Cys Phe Cys Lys Lys Ile Cys
65                  70                  75                  80 tagtagtagc ctcggctttg ctggcgttgg gcggcacagg caggtcgtcg gcacgaaacg     419
caattcaagc atatatatcg gtcctcctcc tgcgntgcgc tgnctaactc gatcccgntt     479
tctctttcga tcganttcat tgntt                                          504

<210> SEQ ID NO 2
<211> LENGTH: 80
<212> TYPE: PRT
<213> ORGANISM: artificial
<220> FEATURE:
<223> OTHER INFORMATION: Synthetic Construct

<400> SEQUENCE: 2

Met Ala Leu Ser Arg Arg Met Ala Ala Pro Val Leu Val Leu Met Leu
1               5                   10                  15

Leu Leu Val Ala Thr Glu Leu Gly Thr Thr Lys Val Ala Glu Ala Arg
            20                  25                  30

His Cys Leu Ser Gln Ser His Arg Phe Lys Gly Leu Cys Met Ser Ser
```

```
                    35                  40                  45
Asn Asn Cys Ala Asn Val Cys Gln Thr Glu Asn Phe Pro Gly Gly Glu
     50                  55                  60
Cys Lys Ala Glu Gly Ala Thr Arg Lys Cys Phe Cys Lys Lys Ile Cys
65                  70                  75                  80

<210> SEQ ID NO 3
<211> LENGTH: 49
<212> TYPE: PRT
<213> ORGANISM: artificial
<220> FEATURE:
<223> OTHER INFORMATION: HXL001 Zea mays mature domain

<400> SEQUENCE: 3

Arg His Cys Leu Ser Gln Ser His Arg Phe Lys Gly Leu Cys Met Ser
1               5                   10                  15

Ser Asn Asn Cys Ala Asn Val Cys Glu Thr Gln Asn Phe Pro Gly Gly
            20                  25                  30

Glu Cys Lys Ala Glu Gly Ala Thr Arg Lys Cys Phe Cys Lys Lys Ile
        35                  40                  45

Cys

<210> SEQ ID NO 4
<211> LENGTH: 662
<212> TYPE: DNA
<213> ORGANISM: artificial
<220> FEATURE:
<223> OTHER INFORMATION: HXL002 Triticum aestivum na
<220> FEATURE:
<221> NAME/KEY: CDS
<222> LOCATION: (94)..(339)

<400> SEQUENCE: 4
```

| | |
|---|---:|
| ccacgcgtcc gcttctccat tcgctttgct aacacagtcc ccagtagcag cagcagcagg | 60 |
| acagctcagt ctcgggtgaa gctgagcaga tcg atg gcg ctc tct cgt cgc atg<br>                                              Met Ala Leu Ser Arg Arg Met<br>                                                 1              5 | 114 |
| gct gcg tcc gcc ctc ctg ctg ctg gtc ctc ctc gtc gcc aca gag atg<br>Ala Ala Ser Ala Leu Leu Leu Leu Val Leu Leu Val Ala Thr Glu Met<br>        10                 15                 20 | 162 |
| ggg gcg acg acg gtc aag ctg gct gag gcg cgg gac tgc ctg tcc cag<br>Gly Ala Thr Thr Val Lys Leu Ala Glu Ala Arg Asp Cys Leu Ser Gln<br>25                     30                 35 | 210 |
| agc cac aag ttc aag ggc gcc tgc ctc agc agc agc aac tgc gcc gcc<br>Ser His Lys Phe Lys Gly Ala Cys Leu Ser Ser Ser Asn Cys Ala Ala<br>40                 45                 50                 55 | 258 |
| gtc tgc cgc acc gag aac ttc ccc gac ggg gag tgc cac acg cac aac<br>Val Cys Arg Thr Glu Asn Phe Pro Asp Gly Glu Cys His Thr His Asn<br>                 60                 65                 70 | 306 |
| ttc gcc cgc aag tgc ttc tgc aag agg gcc tgc tagcccgcct gctcgatcgc<br>Phe Ala Arg Lys Cys Phe Cys Lys Arg Ala Cys<br>               75                 80 | 359 |
| cccggccgcc ctgccggcca gcgccgccac gtccgatgct agctagctgt tagatcgtcc | 419 |
| gtgccttttg gtagatctgt tcgtcagtcc gttcccgttc gtcactagta gctgttcgtg | 479 |
| tggctgtctc ccgtaataaa gtacgaaatc aaccggggtc tcggtagttt ggttcgcagc | 539 |
| acgtcgtgtt tgtcgctgct ttgtgtggta atgtaatatg gtccttgttt cagtatggac | 599 |
| ggacgtgtgc actgcatcta aatctgagga tggtttcata cttaaaccat acttgaacca | 659 |
| aaa | 662 |

<210> SEQ ID NO 5
<211> LENGTH: 82
<212> TYPE: PRT
<213> ORGANISM: artificial
<220> FEATURE:
<223> OTHER INFORMATION: Synthetic Construct

<400> SEQUENCE: 5

```
Met Ala Leu Ser Arg Met Ala Ala Ser Ala Leu Leu Leu Val
1               5                   10                  15

Leu Leu Val Ala Thr Glu Met Gly Ala Thr Thr Val Lys Leu Ala Glu
            20                  25                  30

Ala Arg Asp Cys Leu Ser Gln Ser His Lys Phe Lys Gly Ala Cys Leu
        35                  40                  45

Ser Ser Asn Cys Ala Ala Val Cys Arg Thr Glu Asn Phe Pro Asp
    50                  55                  60

Gly Glu Cys His Thr His Asn Phe Ala Arg Lys Cys Phe Cys Lys Arg
65                  70                  75                  80

Ala Cys
```

<210> SEQ ID NO 6
<211> LENGTH: 49
<212> TYPE: PRT
<213> ORGANISM: artificial
<220> FEATURE:
<223> OTHER INFORMATION: HXL002 Triticum aestivum mature domain

<400> SEQUENCE: 6

```
Arg Asp Cys Leu Ser Gln Ser His Lys Phe Lys Gly Ala Cys Leu Ser
1               5                   10                  15

Ser Ser Asn Cys Ala Ala Val Cys Arg Thr Glu Asn Phe Pro Asp Gly
            20                  25                  30

Glu Cys His Thr His Asn Phe Ala Arg Lys Cys Phe Cys Lys Arg Ala
        35                  40                  45

Cys
```

<210> SEQ ID NO 7
<211> LENGTH: 392
<212> TYPE: DNA
<213> ORGANISM: artificial
<220> FEATURE:
<223> OTHER INFORMATION: HXL003 Triticum aestivum
<220> FEATURE:
<221> NAME/KEY: CDS
<222> LOCATION: (54)..(275)

<400> SEQUENCE: 7

```
ttgaaggtct taatctgtca tagaaccctc tcaatctttc acaggaaaac tag atg      56
                                                            Met
                                                            1 gat cgg tcc atg aag gtc ttt gcg gtc gtc ttc ctg ctc ctt gtg gcc   104
Asp Arg Ser Met Lys Val Phe Ala Val Val Phe Leu Leu Leu Val Ala
            5                   10                  15 aca ggc ttc cag gga gcg gtg cag gtt gct ttg gcg agg gac tgt act   152
Thr Gly Phe Gln Gly Ala Val Gln Val Ala Leu Ala Arg Asp Cys Thr
            20                  25                  30 tca cag agc cac aag ttt gtg ggg ctg tgc ctg agc gac cgc aac tgt   200
Ser Gln Ser His Lys Phe Val Gly Leu Cys Leu Ser Asp Arg Asn Cys
        35                  40                  45 gca agt gtt tgc ctg acc gag tat ttc acc gga ggc aag tgc gac cac   248
```

```
Ala Ser Val Cys Leu Thr Glu Tyr Phe Thr Gly Gly Lys Cys Asp His
 50                  55                  60                  65 cga cgt tgt gtc tgt acc aag ggc tgc tagatggccc gtaatcttct          295
Arg Arg Cys Val Cys Thr Lys Gly Cys
                70 tgcacacatg cttccgtgta ataataataa ctgctgaata ataagactag atctgcatct  355 atgcatgtat gatgcataaa aaaaaaaaaa aaaaaaa                           392

<210> SEQ ID NO 8
<211> LENGTH: 74
<212> TYPE: PRT
<213> ORGANISM: artificial
<220> FEATURE:
<223> OTHER INFORMATION: Synthetic Construct

<400> SEQUENCE: 8

Met Asp Arg Ser Met Lys Val Phe Ala Val Val Phe Leu Leu Leu Val
  1               5                  10                  15

Ala Thr Gly Phe Gln Gly Ala Val Gln Val Ala Leu Ala Arg Asp Cys
                 20                  25                  30

Thr Ser Gln Ser His Lys Phe Val Gly Leu Cys Leu Ser Asp Arg Asn
             35                  40                  45

Cys Ala Ser Val Cys Leu Thr Glu Tyr Phe Thr Gly Gly Lys Cys Asp
         50                  55                  60

His Arg Arg Cys Val Cys Thr Lys Gly Cys
 65                  70

<210> SEQ ID NO 9
<211> LENGTH: 45
<212> TYPE: PRT
<213> ORGANISM: artificial
<220> FEATURE:
<223> OTHER INFORMATION: HXL003 Triticum aestivum

<400> SEQUENCE: 9

Arg Asp Cys Thr Ser Gln Ser His Lys Phe Val Gly Leu Cys Leu Ser
  1               5                  10                  15

Asp Arg Asn Cys Ala Ser Val Cys Leu Thr Glu Tyr Phe Thr Gly Gly
                 20                  25                  30

Lys Cys Asp His Arg Arg Cys Val Cys Thr Lys Gly Cys
             35                  40                  45

<210> SEQ ID NO 10
<211> LENGTH: 478
<212> TYPE: DNA
<213> ORGANISM: artificial
<220> FEATURE:
<223> OTHER INFORMATION: HXL004 Nicotiana benthamiana na
<220> FEATURE:
<221> NAME/KEY: CDS
<222> LOCATION: (31)..(261)
<220> FEATURE:
<221> NAME/KEY: misc_feature
<222> LOCATION: (396)..(396)
<223> OTHER INFORMATION: n = A, T, C or G

<400> SEQUENCE: 10
aacaaattaa agaattttaa gaaaacaag atg gct ggc ttt ccc aaa gtg ctt   54
                                Met Ala Gly Phe Pro Lys Val Leu
                                  1               5 gca act gtt ttc ctt acg ctg atg ctg gtt ttt gct act gag atg gga  102
Ala Thr Val Phe Leu Thr Leu Met Leu Val Phe Ala Thr Glu Met Gly
         10                  15                  20
```

```
cca atg gtg act gag gcg agg acc tgc gag tca cag agc cac cga ttc      150
Pro Met Val Thr Glu Ala Arg Thr Cys Glu Ser Gln Ser His Arg Phe
 25              30                  35                  40 aag ggt ttg tgt ttc agt agg agc aac tgt gcg tct gtt tgc cat act      198
Lys Gly Leu Cys Phe Ser Arg Ser Asn Cys Ala Ser Val Cys His Thr
                 45                  50                  55 gag ggc ttt aac ggt ggc cac tgc cgt gga ttc cgt cgc cgt tgc ttc      246
Glu Gly Phe Asn Gly Gly His Cys Arg Gly Phe Arg Arg Arg Cys Phe
             60                  65                  70 tgc acc aga cac tgt taattattat tattatgtgt actgctgtgt aatatgaacg      301
Cys Thr Arg His Cys
         75 tctcttctcg tttcttctgg tgtttgtcat gaaataagaa tgaccatctg aactcagaaa    361 cagatcagaa tggttaattc ccttccgttt cctangagtt aaatggttgc tggcaacttt    421 taattgcgaa ctctttctgt aactattggg tattacgata tattaaaaaa aaaacca       478

<210> SEQ ID NO 11
<211> LENGTH: 77
<212> TYPE: PRT
<213> ORGANISM: artificial
<220> FEATURE:
<223> OTHER INFORMATION: Synthetic Construct

<400> SEQUENCE: 11

Met Ala Gly Phe Pro Lys Val Leu Ala Thr Val Phe Leu Thr Leu Met
 1               5                  10                  15

Leu Val Phe Ala Thr Glu Met Gly Pro Met Val Thr Glu Ala Arg Thr
             20                  25                  30

Cys Glu Ser Gln Ser His Arg Phe Lys Gly Leu Cys Phe Ser Arg Ser
         35                  40                  45

Asn Cys Ala Ser Val Cys His Thr Glu Gly Phe Asn Gly Gly His Cys
     50                  55                  60

Arg Gly Phe Arg Arg Arg Cys Phe Cys Thr Arg His Cys
 65                  70                  75

<210> SEQ ID NO 12
<211> LENGTH: 47
<212> TYPE: PRT
<213> ORGANISM: artificial
<220> FEATURE:
<223> OTHER INFORMATION: HXL004 Nicotiana benthamiana mature domain aa

<400> SEQUENCE: 12

Arg Thr Cys Glu Ser Gln Ser His Arg Phe Lys Gly Leu Cys Phe Ser
 1               5                  10                  15

Arg Ser Asn Cys Ala Ser Val Cys His Thr Glu Gly Phe Asn Gly Gly
             20                  25                  30

His Cys Arg Gly Phe Arg Arg Arg Cys Phe Cys Thr Arg His Cys
         35                  40                  45

<210> SEQ ID NO 13
<211> LENGTH: 398
<212> TYPE: DNA
<213> ORGANISM: artificial
<220> FEATURE:
<223> OTHER INFORMATION: HXL005 Taraxacum kok-saghyz na
<220> FEATURE:
<221> NAME/KEY: CDS
<222> LOCATION: (70)..(261)
<220> FEATURE:
<221> NAME/KEY: misc_feature
```

```
<222> LOCATION: (340)..(342)
<223> OTHER INFORMATION: n = A, T, C or G
<220> FEATURE:
<221> NAME/KEY: misc_feature
<222> LOCATION: (372)..(375)
<223> OTHER INFORMATION: n = A, T, C or G
<220> FEATURE:
<221> NAME/KEY: misc_feature
<222> LOCATION: (379)..(384)
<223> OTHER INFORMATION: n = A, T, C or G
<220> FEATURE:
<221> NAME/KEY: misc_feature
<222> LOCATION: (387)..(388)
<223> OTHER INFORMATION: n = A, T, C or G
<220> FEATURE:
<221> NAME/KEY: misc_feature
<222> LOCATION: (391)..(394)
<223> OTHER INFORMATION: n = A, T, C or G
<220> FEATURE:
<221> NAME/KEY: misc_feature
<222> LOCATION: (398)..(398)
<223> OTHER INFORMATION: n = A, T, C or G

<400> SEQUENCE: 13
ggccattatg gccggggatt gttttctgt gcatcataat tcaaagtggg aaaaagcctg      60 tttgtgttc atg ttg ctg cct gct ctc ttt gct act gat aag act ttg gtg    111
         Met Leu Leu Pro Ala Leu Phe Ala Thr Asp Lys Thr Leu Val
         1               5                   10 agt gtg acc gaa gca aag atg tgt caa acg acg agc cat gca ttt agt      159
Ser Val Thr Glu Ala Lys Met Cys Gln Thr Thr Ser His Ala Phe Ser
15                  20                  25                  30 tgt gtg aac gac tcg ggt tgc agt ggc tcc tgc gaa aag caa gga ttt      207
Cys Val Asn Asp Ser Gly Cys Ser Gly Ser Cys Glu Lys Gln Gly Phe
                35                  40                  45 gct agc ggc aaa tgt gat gga gta cgt cgt cgt tgt acg tgt tac aag      255
Ala Ser Gly Lys Cys Asp Gly Val Arg Arg Arg Cys Thr Cys Tyr Lys
            50                  55                  60 aag tgt tgagcatata tatgctcttt attaaaacta tgtaaactag tcacgtggtg      311
Lys Cys actttctcct gtaccatctt tggtatctnn nggtatatta aataaagttt gacgtttgtc    371
nnnnaaannn nnnccnnccn nnnaatn                                          398

<210> SEQ ID NO 14
<211> LENGTH: 64
<212> TYPE: PRT
<213> ORGANISM: artificial
<220> FEATURE:
<223> OTHER INFORMATION: Synthetic Construct

<400> SEQUENCE: 14

Met Leu Leu Pro Ala Leu Phe Ala Thr Asp Lys Thr Leu Val Ser Val
1               5                   10                  15

Thr Glu Ala Lys Met Cys Gln Thr Thr Ser His Ala Phe Ser Cys Val
            20                  25                  30

Asn Asp Ser Gly Cys Ser Gly Ser Cys Glu Lys Gln Gly Phe Ala Ser
        35                  40                  45

Gly Lys Cys Asp Gly Val Arg Arg Arg Cys Thr Cys Tyr Lys Lys Cys
    50                  55                  60

<210> SEQ ID NO 15
<211> LENGTH: 45
<212> TYPE: PRT
<213> ORGANISM: artificial
<220> FEATURE:
<223> OTHER INFORMATION: HXL005 Taraxacum kok-saghyz mature domain
```

<400> SEQUENCE: 15

```
Lys Met Cys Gln Thr Thr Ser His Ala Phe Ser Cys Val Asn Asp Ser
1               5                   10                  15

Gly Cys Ser Gly Ser Cys Glu Lys Gln Gly Phe Ala Ser Gly Lys Cys
            20                  25                  30

Asp Gly Val Arg Arg Arg Cys Thr Cys Tyr Lys Lys Cys
        35                  40                  45
```

<210> SEQ ID NO 16
<211> LENGTH: 600
<212> TYPE: DNA
<213> ORGANISM: artificial
<220> FEATURE:
<223> OTHER INFORMATION: HXL006 Triticum aestivum
<220> FEATURE:
<221> NAME/KEY: CDS
<222> LOCATION: (23)..(250)
<220> FEATURE:
<221> NAME/KEY: misc_feature
<222> LOCATION: (566)..(568)
<223> OTHER INFORMATION: n = n = A, T, C or G
<220> FEATURE:
<221> NAME/KEY: misc_feature
<222> LOCATION: (574)..(575)
<223> OTHER INFORMATION: n = n = A, T, C or G

<400> SEQUENCE: 16

```
gcacgaggat aacttgcaat cc atg aat tca tcc cgc aag ttc ttc atg gtt      52
                        Met Asn Ser Ser Arg Lys Phe Phe Met Val
                        1               5                   10 gtt gcc gtc ctt gcc ttg ctc gtc gtg gct aca gtg gtg gcg ccg gcg      100
Val Ala Val Leu Ala Leu Leu Val Val Ala Thr Val Val Ala Pro Ala
            15                  20                  25 cag gcg gta gac tgc agg aca gcg agc acc cgg ttc aac ggc ata tgc      148
Gln Ala Val Asp Cys Arg Thr Ala Ser Thr Arg Phe Asn Gly Ile Cys
        30                  35                  40 atc ctg gac agc agt tgc gcc aac atg tgc atc acc gag ggg ttc ctg      196
Ile Leu Asp Ser Ser Cys Ala Asn Met Cys Ile Thr Glu Gly Phe Leu
        45                  50                  55 gct ggc ggg gag tgt gaa ggt ctc cac cga cgc tgc atg tgc aaa aca      244
Ala Gly Gly Glu Cys Glu Gly Leu His Arg Arg Cys Met Cys Lys Thr
    60                  65                  70 cca tgc taggcgaagc atatgcatag tctggactgc ttcatcagga agttttccg       300
Pro Cys
75 atttagataa aaacaaggaa aaagattttt ttttctaaaa gaaaagaaaa tggagttgta    360 acacatactg tgttctttta gttttttttt tcacatgttc ctttgggaga ttgtggttgt    420 gcatttgatg cattttgtt gatcgtacaa tccagtttga tgtgttttg ttgtaaactt      480 gaagttggcc attttgtcat tgtgtaagat tattttccaa gattcattca tttgtgatca    540 tgcaatgcag tattgtacta ccaaannnaa aannaaaaa aaaaaaaaaa aaccctccgg      600
```

<210> SEQ ID NO 17
<211> LENGTH: 76
<212> TYPE: PRT
<213> ORGANISM: artificial
<220> FEATURE:
<223> OTHER INFORMATION: Synthetic Construct

<400> SEQUENCE: 17

```
Met Asn Ser Ser Arg Lys Phe Phe Met Val Val Ala Val Leu Ala Leu
1               5                   10                  15
```

```
Leu Val Val Ala Thr Val Val Ala Pro Ala Gln Ala Val Asp Cys Arg
            20                  25                  30

Thr Ala Ser Thr Arg Phe Asn Gly Ile Cys Ile Leu Asp Ser Ser Cys
        35                  40                  45

Ala Asn Met Cys Ile Thr Glu Gly Phe Leu Ala Gly Gly Glu Cys Glu
50                  55                  60

Gly Leu His Arg Arg Cys Met Cys Lys Thr Pro Cys
65                  70                  75

<210> SEQ ID NO 18
<211> LENGTH: 48
<212> TYPE: PRT
<213> ORGANISM: artificial
<220> FEATURE:
<223> OTHER INFORMATION: HXL006 Triticum aestivum

<400> SEQUENCE: 18

Val Asp Cys Arg Thr Ala Ser Thr Arg Phe Asn Gly Ile Cys Ile Leu
1               5                   10                  15

Asp Ser Ser Cys Ala Asn Met Cys Ile Thr Glu Gly Phe Leu Ala Gly
            20                  25                  30

Gly Glu Cys Glu Gly Leu His Arg Arg Cys Met Cys Lys Thr Pro Cys
        35                  40                  45

<210> SEQ ID NO 19
<211> LENGTH: 563
<212> TYPE: DNA
<213> ORGANISM: artificial
<220> FEATURE:
<223> OTHER INFORMATION: HXL007 Cyamopsis tetragonoloba na
<220> FEATURE:
<221> NAME/KEY: CDS
<222> LOCATION: (106)..(330)

<400> SEQUENCE: 19
gcacgaggaa attatatatt taaacaagta gtagttaatc atcaataata ctatagaatc      60
gaattgaatt gaatactgta attaattaag ctaaggtagc tagct atg gag aag aaa    117
                                                Met Glu Lys Lys
                                                  1 tca ctg gct gga ttc tgc tgc ctc ttc ctc att ctc ttt ctt gct caa     165
Ser Leu Ala Gly Phe Cys Cys Leu Phe Leu Ile Leu Phe Leu Ala Gln
 5                  10                  15                  20 gaa ata gtg gtg aaa aca gag gca agg aca tgt gag agt ctg gca gac     213
Glu Ile Val Val Lys Thr Glu Ala Arg Thr Cys Glu Ser Leu Ala Asp
                25                  30                  35 aca tac agg gga ccc tgt ttc aca gat ggt agc tgc gat gat cac tgc     261
Thr Tyr Arg Gly Pro Cys Phe Thr Asp Gly Ser Cys Asp Asp His Cys
            40                  45                  50 aag aac aaa gag cac tta atc agt gga aga tgc aga aat gat ttt cgc     309
Lys Asn Lys Glu His Leu Ile Ser Gly Arg Cys Arg Asn Asp Phe Arg
        55                  60                  65 tgt tgg tgc acc aga aac tgt taaattctgg actttccccc atcaagatgc         360
Cys Trp Cys Thr Arg Asn Cys
    70              75 atgcacaacg aaccttaatt attatatata catcaataat aaacaaaata taaataaaac     420
tagctgcctc tgtatcttga ccatgtatta ttactagtac cacctctgtc tgaatttcat     480
acatactatt ttaaatgttc tgagtacata acggatgagt tatgtacttt atgtcaaaca     540
ataataaact gttgttatgt acc                                             563
```

-continued

<210> SEQ ID NO 20
<211> LENGTH: 75
<212> TYPE: PRT
<213> ORGANISM: artificial
<220> FEATURE:
<223> OTHER INFORMATION: Synthetic Construct

<400> SEQUENCE: 20

```
Met Glu Lys Lys Ser Leu Ala Gly Phe Cys Cys Leu Phe Leu Ile Leu
1               5                   10                  15

Phe Leu Ala Gln Glu Ile Val Val Lys Thr Glu Ala Arg Thr Cys Glu
            20                  25                  30

Ser Leu Ala Asp Thr Tyr Arg Gly Pro Cys Phe Thr Asp Gly Ser Cys
        35                  40                  45

Asp Asp His Cys Lys Asn Lys Glu His Leu Ile Ser Gly Arg Cys Arg
    50                  55                  60

Asn Asp Phe Arg Cys Trp Cys Thr Arg Asn Cys
65                  70                  75
```

<210> SEQ ID NO 21
<211> LENGTH: 47
<212> TYPE: PRT
<213> ORGANISM: artificial
<220> FEATURE:
<223> OTHER INFORMATION: HXL007 Cyamopsis tetragonoloba mature domain

<400> SEQUENCE: 21

```
Arg Thr Cys Glu Ser Leu Ala Asp Thr Tyr Arg Gly Pro Cys Phe Thr
1               5                   10                  15

Asp Gly Ser Cys Asp Asp His Cys Lys Asn Lys Glu His Leu Ile Ser
            20                  25                  30

Gly Arg Cys Arg Asn Asp Phe Arg Cys Trp Cys Thr Arg Asn Cys
        35                  40                  45
```

<210> SEQ ID NO 22
<211> LENGTH: 512
<212> TYPE: DNA
<213> ORGANISM: artificial
<220> FEATURE:
<223> OTHER INFORMATION: HXL008 Picramnia pentandra na
<220> FEATURE:
<221> NAME/KEY: CDS
<222> LOCATION: (31)..(261)
<220> FEATURE:
<221> NAME/KEY: misc_feature
<222> LOCATION: (330)..(330)
<223> OTHER INFORMATION: n = A, T, C or G
<220> FEATURE:
<221> NAME/KEY: misc_feature
<222> LOCATION: (408)..(409)
<223> OTHER INFORMATION: n = A, T, C or G
<220> FEATURE:
<221> NAME/KEY: misc_feature
<222> LOCATION: (412)..(412)
<223> OTHER INFORMATION: n = A, T, C or G
<220> FEATURE:
<221> NAME/KEY: misc_feature
<222> LOCATION: (425)..(425)
<223> OTHER INFORMATION: n = A, T, C or G
<220> FEATURE:
<221> NAME/KEY: misc_feature
<222> LOCATION: (452)..(452)
<223> OTHER INFORMATION: n = A, T, C or G
<220> FEATURE:
<221> NAME/KEY: misc_feature
<222> LOCATION: (457)..(457)
<223> OTHER INFORMATION: n = A, T, C or G
<220> FEATURE:

```
<221> NAME/KEY: misc_feature
<222> LOCATION: (465)..(465)
<223> OTHER INFORMATION: n = A, T, C or G
<220> FEATURE:
<221> NAME/KEY: misc_feature
<222> LOCATION: (488)..(490)
<223> OTHER INFORMATION: n = A, T, C or G
<220> FEATURE:
<221> NAME/KEY: misc_feature
<222> LOCATION: (512)..(512)
<223> OTHER INFORMATION: n = A, T, C or G

<400> SEQUENCE: 22
ataatcgcta ctttgttttt ctggaaaaaa atg gac aag aag ttg ttt ggg ttt      54
                                    Met Asp Lys Lys Leu Phe Gly Phe
                                    1               5 tta ctg ttg atg ttc atc tta ttt gct tca cag gaa agc atg gtt caa     102
Leu Leu Leu Met Phe Ile Leu Phe Ala Ser Gln Glu Ser Met Val Gln
    10              15                  20 gtt gaa gca aaa gtt tgc acc aaa ccg agt aag ttc ttc aag ggt tta     150
Val Glu Ala Lys Val Cys Thr Lys Pro Ser Lys Phe Phe Lys Gly Leu
25              30                  35                  40 tgc ggc act gac ggg gca tgt acc aca gct tgc agg aag gaa ggc tta     198
Cys Gly Thr Asp Gly Ala Cys Thr Thr Ala Cys Arg Lys Glu Gly Leu
                45                  50                  55 cac agt ggg tat tgt cag ctt aag ggg ttt ctt aat tcc gtt tgc gtt     246
His Ser Gly Tyr Cys Gln Leu Lys Gly Phe Leu Asn Ser Val Cys Val
            60                  65                  70 tgc aga aag cat tgt taaattcaaa cagacaatgt actatctccc tatacatgtc     301
Cys Arg Lys His Cys
        75 gctgcctaaa atacactata ggcctttanc ccctttggt accaaataat attaatataa     361 catcaaccac ataaatattt ggatgagcca aacttatgat accaagnnaa naaaaaaaac    421 cccnaggggg ggcccgtacc attcccccta natganccta ttanattaac ggcctcgttt    481 aaactcnnna cgggaaaacc tgggttacaa n                                   512

<210> SEQ ID NO 23
<211> LENGTH: 77
<212> TYPE: PRT
<213> ORGANISM: artificial
<220> FEATURE:
<223> OTHER INFORMATION: Synthetic Construct

<400> SEQUENCE: 23

Met Asp Lys Lys Leu Phe Gly Phe Leu Leu Leu Met Phe Ile Leu Phe
1               5                   10                  15

Ala Ser Gln Glu Ser Met Val Gln Val Glu Ala Lys Val Cys Thr Lys
            20                  25                  30

Pro Ser Lys Phe Phe Lys Gly Leu Cys Gly Thr Asp Gly Ala Cys Thr
        35                  40                  45

Thr Ala Cys Arg Lys Glu Gly Leu His Ser Gly Tyr Cys Gln Leu Lys
    50                  55                  60

Gly Phe Leu Asn Ser Val Cys Val Cys Arg Lys His Cys
65                  70                  75

<210> SEQ ID NO 24
<211> LENGTH: 50
<212> TYPE: PRT
<213> ORGANISM: artificial
<220> FEATURE:
<223> OTHER INFORMATION: HXL008 Picramnia pentandra mature domain aa
```

-continued

```
<400> SEQUENCE: 24

Lys Val Cys Thr Lys Pro Ser Lys Phe Phe Lys Gly Leu Cys Gly Thr
1               5                   10                  15

Asp Gly Ala Cys Thr Thr Ala Cys Arg Lys Glu Gly Leu His Ser Gly
            20                  25                  30

Tyr Cys Gln Leu Lys Gly Phe Leu Asn Ser Val Cys Val Cys Arg Lys
        35                  40                  45

His Cys
    50

<210> SEQ ID NO 25
<211> LENGTH: 441
<212> TYPE: DNA
<213> ORGANISM: artificial
<220> FEATURE:
<223> OTHER INFORMATION: HXL009 Zea mays na
<220> FEATURE:
<221> NAME/KEY: CDS
<222> LOCATION: (8)..(241)

<400> SEQUENCE: 25 aataacc atg gcg gca tct aac aag att gca gcg gca cat gtc gtc ttc        49
        Met Ala Ala Ser Asn Lys Ile Ala Ala Ala His Val Val Phe
        1               5                   10 gtc ctt gcc ttg ctc ctt gtg gcc tat cgt gcg gag gca act gtc tgc       97
Val Leu Ala Leu Leu Leu Val Ala Tyr Arg Ala Glu Ala Thr Val Cys
15                  20                  25                  30 atg agg cat aac aat ttc tat cac ggc cca tgc atg agc aac aag gac      145
Met Arg His Asn Asn Phe Tyr His Gly Pro Cys Met Ser Asn Lys Asp
                35                  40                  45 tgt gcc aac tcg tgc gtt caa cat aac ctc ggt gtc ggc ggg tat tgc      193
Cys Ala Asn Ser Cys Val Gln His Asn Leu Gly Val Gly Gly Tyr Cys
            50                  55                  60 agg ggc aag atc cca ttc aac aaa gaa tgc atg tgt aca ttt gaa tgc      241
Arg Gly Lys Ile Pro Phe Asn Lys Glu Cys Met Cys Thr Phe Glu Cys
65                  70                  75 ccatgagtca aaagccacta tatctgacgg gcgcaacttg ttatatatct agggatggga    301
tgtcgtttgg catgtcctcc attttgaaag tgtccaagtg agactttata catatatgca    361
gttgagagat ggaattaata ataagagcaa acaattatgt tgttgtgcat gttttaaaaa    421
aaaaaaaaaa aaaaaaaaaa                                                 441

<210> SEQ ID NO 26
<211> LENGTH: 78
<212> TYPE: PRT
<213> ORGANISM: artificial
<220> FEATURE:
<223> OTHER INFORMATION: Synthetic Construct

<400> SEQUENCE: 26

Met Ala Ala Ser Asn Lys Ile Ala Ala Ala His Val Val Phe Val Leu
1               5                   10                  15

Ala Leu Leu Leu Val Ala Tyr Arg Ala Glu Ala Thr Val Cys Met Arg
            20                  25                  30

His Asn Asn Phe Tyr His Gly Pro Cys Met Ser Asn Lys Asp Cys Ala
        35                  40                  45

Asn Ser Cys Val Gln His Asn Leu Gly Val Gly Gly Tyr Cys Arg Gly
    50                  55                  60

Lys Ile Pro Phe Asn Lys Glu Cys Met Cys Thr Phe Glu Cys
65                  70                  75
```

```
<210> SEQ ID NO 27
<211> LENGTH: 51
<212> TYPE: PRT
<213> ORGANISM: artificial
<220> FEATURE:
<223> OTHER INFORMATION: HXL009 Zea mays mature domain aa

<400> SEQUENCE: 27

Thr Val Cys Met Arg His Asn Asn Phe Tyr His Gly Pro Cys Met Ser
1               5                   10                  15

Asn Lys Asp Cys Ala Asn Ser Cys Val Gln His Asn Leu Gly Val Gly
            20                  25                  30

Gly Tyr Cys Arg Gly Lys Ile Pro Phe Asn Lys Glu Cys Met Cys Thr
        35                  40                  45

Phe Glu Cys
    50

<210> SEQ ID NO 28
<211> LENGTH: 545
<212> TYPE: DNA
<213> ORGANISM: artificial
<220> FEATURE:
<223> OTHER INFORMATION: HXL010 Triticum aestivum
<220> FEATURE:
<221> NAME/KEY: CDS
<222> LOCATION: (45)..(290)

<400> SEQUENCE: 28
ttccttcctt ccctccccc  ttcattcctt cattccttgg agac atg gcg atg gcg      56
                                             Met Ala Met Ala
                                               1 gcg ccc aag ctc atg gtg cca ggc ctg tgc ctg ctt ctg ctg atc atg     104
Ala Pro Lys Leu Met Val Pro Gly Leu Cys Leu Leu Leu Leu Ile Met
 5                  10                  15                  20 ccg ctc ctc ttg ctc cct gga tct caa ggg gcg act tgc aag gag ctg     152
Pro Leu Leu Leu Leu Pro Gly Ser Gln Gly Ala Thr Cys Lys Glu Leu
                25                  30                  35 agc aag acc tat gac tct ccc aac tgc gag acc ggc cga tgc gtg gag     200
Ser Lys Thr Tyr Asp Ser Pro Asn Cys Glu Thr Gly Arg Cys Val Glu
            40                  45                  50 cac tgc caa gtg gag ggc tac ggt agc ggg gtg tgc cag ggg agc tac     248
His Cys Gln Val Glu Gly Tyr Gly Ser Gly Val Cys Gln Gly Ser Tyr
        55                  60                  65 ttc gac ccc tac aag ata ctc tgc ttc tgc aac aaa aac tgc               290
Phe Asp Pro Tyr Lys Ile Leu Cys Phe Cys Asn Lys Asn Cys
    70                  75                  80 tgagccgcca gcgacggcgc attgcttcgg gccggggtgt aataagatgt tagctaaggc    350
gagccgtcgt cgatgcgcga ctcgcacaag tttgtagctg taataggttt catctgtacc    410
aattttattt tcaactgctc gtctcccag ttaagagatt ggtcgtcagc ttgcggaaat     470
ggatcgcttg ttccgctctt ttcatttcgt tcctgttgaa aggaatttc tatctaaaaa     530 aaaaaaaaaa aaaaa                                                     545

<210> SEQ ID NO 29
<211> LENGTH: 82
<212> TYPE: PRT
<213> ORGANISM: artificial
<220> FEATURE:
<223> OTHER INFORMATION: Synthetic Construct

<400> SEQUENCE: 29
```

```
Met Ala Met Ala Ala Pro Lys Leu Met Val Pro Gly Leu Cys Leu Leu
1               5                   10                  15

Leu Leu Ile Met Pro Leu Leu Leu Pro Gly Ser Gln Gly Ala Thr
            20                  25                  30

Cys Lys Glu Leu Ser Lys Thr Tyr Asp Ser Pro Asn Cys Glu Thr Gly
        35                  40                  45

Arg Cys Val Glu His Cys Gln Val Glu Gly Tyr Gly Ser Gly Val Cys
    50                  55                  60

Gln Gly Ser Tyr Phe Asp Pro Tyr Lys Ile Leu Cys Phe Cys Asn Lys
65                  70                  75                  80

Asn Cys
```

```
<210> SEQ ID NO 30
<211> LENGTH: 52
<212> TYPE: PRT
<213> ORGANISM: artificial
<220> FEATURE:
<223> OTHER INFORMATION: HXL010 Triticum aestivum

<400> SEQUENCE: 30
```

```
Ala Thr Cys Lys Glu Leu Ser Lys Thr Tyr Asp Ser Pro Asn Cys Glu
1               5                   10                  15

Thr Gly Arg Cys Val Glu His Cys Gln Val Glu Gly Tyr Gly Ser Gly
            20                  25                  30

Val Cys Gln Gly Ser Tyr Phe Asp Pro Tyr Lys Ile Leu Cys Phe Cys
        35                  40                  45

Asn Lys Asn Cys
        50
```

```
<210> SEQ ID NO 31
<211> LENGTH: 550
<212> TYPE: DNA
<213> ORGANISM: artificial
<220> FEATURE:
<223> OTHER INFORMATION: HXL011 Eucalyptus grandis na
<220> FEATURE:
<221> NAME/KEY: CDS
<222> LOCATION: (8)..(223)

<400> SEQUENCE: 31
```

```
gcacgag gag aag agc aag atg aga tgc atg ggg ctt ttc atg atg gtg      49
        Glu Lys Ser Lys Met Arg Cys Met Gly Leu Phe Met Met Val
        1               5                   10 ctc ctc gtc ctc gct gcc cag gag gcg gag ggg agg gtg tgc gag tcc      97
Leu Leu Val Leu Ala Ala Gln Glu Ala Glu Gly Arg Val Cys Glu Ser
15                  20                  25                  30 cag agc cac ggc ttc aag ggg gct tgc gcc agc aac cac aac tgc gcc      145
Gln Ser His Gly Phe Lys Gly Ala Cys Ala Ser Asn His Asn Cys Ala
                35                  40                  45 ctg gtc tgc cgc aac gag ggc ttc tcc ggc ggc cgt tgc cgt gga ttc      193
Leu Val Cys Arg Asn Glu Gly Phe Ser Gly Gly Arg Cys Arg Gly Phe
            50                  55                  60 cgg cac cgc tgc ttc tgc acc aag ctt tgt tgacggccaa tgcacgtgca       243
Arg His Arg Cys Phe Cys Thr Lys Leu Cys
65                  70 tgcaaccgaa taacgaagtg ttggatgact agctgaggct ggtgtgtgcc gtgtcgtagt    303
gagtgagcga gtgagccaaa taaatatgtt cgaagattct gagttcctta gtttctaagc    363
tttctaggac tttgatgtgc tttgaccatt cactgttctc tctcttctat cgctttgcgt    423
```

```
aatttcttga ttcggggaa aaaaaaaaaa aaaaaaaaaa aaaaaaaaaa aaaaaaaaaa    483
aaaaaaaaaa aaaaaaaaaa aaaaaaaaaa aaaaaaaaaa aaaaaaaaaa aaaaaaaaaa    543
aaaaaaa                                                              550
```

<210> SEQ ID NO 32
<211> LENGTH: 72
<212> TYPE: PRT
<213> ORGANISM: artificial
<220> FEATURE:
<223> OTHER INFORMATION: Synthetic Construct

<400> SEQUENCE: 32

```
Glu Lys Ser Lys Met Arg Cys Met Gly Leu Phe Met Met Val Leu Leu
1               5                   10                  15

Val Leu Ala Ala Gln Glu Ala Glu Gly Arg Val Cys Glu Ser Gln Ser
            20                  25                  30

His Gly Phe Lys Gly Ala Cys Ala Ser Asn His Asn Cys Ala Leu Val
        35                  40                  45

Cys Arg Asn Glu Gly Phe Ser Gly Gly Arg Cys Arg Gly Phe Arg His
    50                  55                  60

Arg Cys Phe Cys Thr Lys Leu Cys
65                  70
```

<210> SEQ ID NO 33
<211> LENGTH: 47
<212> TYPE: PRT
<213> ORGANISM: artificial
<220> FEATURE:
<223> OTHER INFORMATION: HXL011 eucalyptus grandis mature domain aa

<400> SEQUENCE: 33

```
Arg Val Cys Glu Ser Gln Ser His Gly Phe Lys Gly Ala Cys Ala Ser
1               5                   10                  15

Asn His Asn Cys Ala Leu Val Cys Arg Asn Glu Gly Phe Ser Gly Gly
            20                  25                  30

Arg Cys Arg Gly Phe Arg His Arg Cys Phe Cys Thr Lys Leu Cys
        35                  40                  45
```

<210> SEQ ID NO 34
<211> LENGTH: 482
<212> TYPE: DNA
<213> ORGANISM: artificial
<220> FEATURE:
<223> OTHER INFORMATION: HXL012 Amaranthus retroflectus na
<220> FEATURE:
<221> NAME/KEY: CDS
<222> LOCATION: (31)..(252)

<400> SEQUENCE: 34

```
gcacgaggat caagatcctc aaattaatca atg aag aca ttt gga gct ttc gtt     54
                                Met Lys Thr Phe Gly Ala Phe Val
                                 1               5 ctt att ttt ctt ctt gca tcc ttc gcc ata aca ggg cca aga atg acg    102
Leu Ile Phe Leu Leu Ala Ser Phe Ala Ile Thr Gly Pro Arg Met Thr
        10                  15                  20 gaa gca agg atg tgc aaa gct ccg agc aaa ctg ttt agg gga atg tgt    150
Glu Ala Arg Met Cys Lys Ala Pro Ser Lys Leu Phe Arg Gly Met Cys
25                  30                  35                  40 ggt att agg gat tcc aac tgt gat agt gtt tgc agg gcg gaa gga atg    198
Gly Ile Arg Asp Ser Asn Cys Asp Ser Val Cys Arg Ala Glu Gly Met
                45                  50                  55
```

```
gct gct gga gat tgc cat ggc ctt cgt aga cga tgc att tgc agc agg    246
Ala Ala Gly Asp Cys His Gly Leu Arg Arg Arg Cys Ile Cys Ser Arg
            60                  65                  70 cct tgt ccttaaatta ccttatgtaa tctcctaaaa ataatgataa caaatgtttc    302
Pro Cys tatcttcacc attagcttta attattatca cctggctagt agctacatgc atataatgta    362
atcttatata gcgtcttgct atcactctat ctctatgttt aaataatttc gtcttttatg    422
tattaattgt ttcttttcac atctataaat taacgataag atatctgtat tcgtacactt    482
```

<210> SEQ ID NO 35
<211> LENGTH: 74
<212> TYPE: PRT
<213> ORGANISM: artificial
<220> FEATURE:
<223> OTHER INFORMATION: Synthetic Construct

<400> SEQUENCE: 35

```
Met Lys Thr Phe Gly Ala Phe Val Leu Ile Phe Leu Leu Ala Ser Phe
1               5                   10                  15

Ala Ile Thr Gly Pro Arg Met Thr Glu Ala Arg Met Cys Lys Ala Pro
            20                  25                  30

Ser Lys Leu Phe Arg Gly Met Cys Gly Ile Arg Asp Ser Asn Cys Asp
        35                  40                  45

Ser Val Cys Arg Ala Glu Gly Met Ala Ala Gly Asp Cys His Gly Leu
    50                  55                  60

Arg Arg Arg Cys Ile Cys Ser Arg Pro Cys
65                  70
```

<210> SEQ ID NO 36
<211> LENGTH: 48
<212> TYPE: PRT
<213> ORGANISM: artificial
<220> FEATURE:
<223> OTHER INFORMATION: HXL012 Amaranthus retroflectus mature domain aa

<400> SEQUENCE: 36

```
Arg Met Cys Lys Ala Pro Ser Lys Leu Phe Arg Gly Met Cys Gly Ile
1               5                   10                  15

Arg Asp Ser Asn Cys Asp Ser Val Cys Arg Ala Glu Gly Met Ala Ala
            20                  25                  30

Gly Asp Cys His Gly Leu Arg Arg Arg Cys Ile Cys Ser Arg Pro Cys
        35                  40                  45
```

<210> SEQ ID NO 37
<211> LENGTH: 486
<212> TYPE: DNA
<213> ORGANISM: artificial
<220> FEATURE:
<223> OTHER INFORMATION: HXL013 Glycine max na
<220> FEATURE:
<221> NAME/KEY: CDS
<222> LOCATION: (30)..(251)

<400> SEQUENCE: 37

```
gaaacaattc aattcaatct gcctcgatc atg gag agg aaa aca ttt ggg ttt    53
                                Met Glu Arg Lys Thr Phe Gly Phe
                                1               5 ttg ttc ttg ctc ctc ctt gtc tta gct tct gat gtg acg gtg aag aga    101
Leu Phe Leu Leu Leu Leu Val Leu Ala Ser Asp Val Thr Val Lys Arg
    10                  15                  20 gca gag gcg aaa gat tgc ttg aca agg agg cac ggg ttc cag ggt aga    149
```

```
                  Ala Glu Ala Lys Asp Cys Leu Thr Arg Arg His Gly Phe Gln Gly Arg
                   25                  30                  35                  40 tgc tta ttc gac agg caa tgt gca cat gtg tgc agg agc gat ggt ttc        197
Cys Leu Phe Asp Arg Gln Cys Ala His Val Cys Arg Ser Asp Gly Phe
                 45                  50                  55 atc ggt ggt cag tgc cga ggc cct ctt cgc aaa tgc ttt tgc agc agg        245
Ile Gly Gly Gln Cys Arg Gly Pro Leu Arg Lys Cys Phe Cys Ser Arg
 60                  65                  70 cca tgt tgatcgaaat tactactgcc aaagaggcca tgaaataaac aaacaaacaa         301
Pro Cys ataaataaat agctttaacc gacacatatg tacttagtgt cggtaggtac gtgtgtcttt      361
tgttatcgat cctagtttgg tggagcaagt atggcatcat gatctagtta tatatatgtc      421
gtgatcatct tgctctgttc agcaataaat tataatggaa attaataaat tagttatgcc      481
ttttc                                                                  486
```

```
<210> SEQ ID NO 38
<211> LENGTH: 74
<212> TYPE: PRT
<213> ORGANISM: artificial
<220> FEATURE:
<223> OTHER INFORMATION: Synthetic Construct

<400> SEQUENCE: 38

Met Glu Arg Lys Thr Phe Gly Phe Leu Phe Leu Leu Leu Val Leu
 1               5                  10                  15

Ala Ser Asp Val Thr Val Lys Arg Ala Glu Ala Lys Asp Cys Leu Thr
                 20                  25                  30

Arg Arg His Gly Phe Gln Gly Arg Cys Leu Phe Asp Arg Gln Cys Ala
             35                  40                  45

His Val Cys Arg Ser Asp Gly Phe Ile Gly Gly Gln Cys Arg Gly Pro
         50                  55                  60

Leu Arg Lys Cys Phe Cys Ser Arg Pro Cys
 65                  70

<210> SEQ ID NO 39
<211> LENGTH: 47
<212> TYPE: PRT
<213> ORGANISM: artificial
<220> FEATURE:
<223> OTHER INFORMATION: HXL013 Glycine max mature domain aa

<400> SEQUENCE: 39

Lys Asp Cys Leu Thr Arg Arg His Gly Phe Gln Gly Arg Cys Leu Phe
 1               5                  10                  15

Asp Arg Gln Cys Ala His Val Cys Arg Ser Asp Gly Pro Ile Gly Gly
                 20                  25                  30

Gln Cys Arg Gly Pro Leu Arg Lys Cys Phe Cys Ser Arg Pro Cys
             35                  40                  45

<210> SEQ ID NO 40
<211> LENGTH: 416
<212> TYPE: DNA
<213> ORGANISM: artificial
<220> FEATURE:
<223> OTHER INFORMATION: HXL014 Tulipa gesneriana na
<220> FEATURE:
<221> NAME/KEY: CDS
<222> LOCATION: (3)..(230)
<220> FEATURE:
<221> NAME/KEY: misc_feature
<222> LOCATION: (355)..(355)
```

```
<223> OTHER INFORMATION: n = A, T, C or G
<220> FEATURE:
<221> NAME/KEY: misc_feature
<222> LOCATION: (380)..(380)
<223> OTHER INFORMATION: n = A, T, C or G
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (395)..(396)
<223> OTHER INFORMATION: n = A, T, C or G
<220> FEATURE:
<221> NAME/KEY: misc_feature
<222> LOCATION: (405)..(405)
<223> OTHER INFORMATION: n = A, T, C or G

<400> SEQUENCE: 40 gg aag ctc agc ata gct ctc ctc tgc tct ttc ttc gct ctc ttc        47
   Lys Leu Ser Ile Ala Leu Leu Cys Ser Phe Phe Ala Leu Phe
   1               5                  10                  15 tta ctg ctg gct tct ggg cct gga gtg gaa gct agt ctc ctc tgc cga   95
Leu Leu Leu Ala Ser Gly Pro Gly Val Glu Ala Ser Leu Leu Cys Arg
            20                  25                  30 agg gtt tcg agc aat ggg ttc aaa gga ctg tgc ttc agc agc gac aag   143
Arg Val Ser Ser Asn Gly Phe Lys Gly Leu Cys Phe Ser Ser Asp Lys
        35                  40                  45 tgt gcc aag gtt tgc atg agc gag ggc aac cgc agt ggt ggt tct tgc   191
Cys Ala Lys Val Cys Met Ser Glu Gly Asn Arg Ser Gly Gly Ser Cys
    50                  55                  60 gat ggc gtt cgc cgt cgg tgc atg tgt aag cca aac tgc tgaaccacag    240
Asp Gly Val Arg Arg Arg Cys Met Cys Lys Pro Asn Cys
65                  70                  75 gcctccgaga acggctgta tctgtagctg ctaagttact ctatctgtag tacgttgagt   300
atgtatgttt tgtgaccaaa ataaagaag aaaaggctca tgatcttgtt ggccngctcc    360
tcgtgtcttg aatatttaan gttangagaa aaagtnactc agttncccca ggtgtt       416

<210> SEQ ID NO 41
<211> LENGTH: 76
<212> TYPE: PRT
<213> ORGANISM: artificial
<220> FEATURE:
<223> OTHER INFORMATION: Synthetic Construct

<400> SEQUENCE: 41

Lys Leu Ser Ile Ala Leu Leu Cys Ser Phe Phe Ala Leu Phe Leu
1               5                  10                  15

Leu Leu Ala Ser Gly Pro Gly Val Glu Ala Ser Leu Leu Cys Arg Arg
            20                  25                  30

Val Ser Ser Asn Gly Phe Lys Gly Leu Cys Phe Ser Ser Asp Lys Cys
        35                  40                  45

Ala Lys Val Cys Met Ser Glu Gly Asn Arg Ser Gly Gly Ser Cys Asp
    50                  55                  60

Gly Val Arg Arg Arg Cys Met Cys Lys Pro Asn Cys
65                  70                  75

<210> SEQ ID NO 42
<211> LENGTH: 49
<212> TYPE: PRT
<213> ORGANISM: artificial
<220> FEATURE:
<223> OTHER INFORMATION: HXL014 tulipa gesneriana mature domain aa
```

<400> SEQUENCE: 42

Leu Leu Cys Arg Arg Val Ser Ser Asn Gly Phe Lys Gly Leu Cys Phe
1               5                   10                  15

Ser Ser Asp Lys Cys Ala Lys Val Cys Met Ser Glu Gly Asn Arg Ser
            20                  25                  30

Gly Gly Ser Cys Asp Gly Val Arg Arg Cys Met Cys Lys Pro Asn
        35                  40                  45

Cys

<210> SEQ ID NO 43
<211> LENGTH: 515
<212> TYPE: DNA
<213> ORGANISM: artificial
<220> FEATURE:
<223> OTHER INFORMATION: HXL015 Oryza sativa na
<220> FEATURE:
<221> NAME/KEY: CDS
<222> LOCATION: (43)..(282)

<400> SEQUENCE: 43

```
ctcatcactc atcagtgagc gcagttcgag tcgccggtac ag atg gct ccg tct        54
                                              Met Ala Pro Ser
                                              1 cgt cgc atg gtc gcg tcc gcc ttc ctc ctc ctg gcc atc ctc gtc gcc     102
Arg Arg Met Val Ala Ser Ala Phe Leu Leu Leu Ala Ile Leu Val Ala
5                   10                  15                  20 aca gag atg ggg acg acc aag gtg gcg gag gcg agg cac tgc ctg tcg     150
Thr Glu Met Gly Thr Thr Lys Val Ala Glu Ala Arg His Cys Leu Ser
                25                  30                  35 cag agc cac agg ttc aag ggc atg tgc gtg agc agc aac aac tgc gcc     198
Gln Ser His Arg Phe Lys Gly Met Cys Val Ser Ser Asn Asn Cys Ala
            40                  45                  50 aac gtg tgc agg acg gag agc ttc ccc gac ggc gag tgc aag tcg cac     246
Asn Val Cys Arg Thr Glu Ser Phe Pro Asp Gly Glu Cys Lys Ser His
        55                  60                  65 ggc ctc gag cgc aag tgc ttc tgc aag aag gtc tgc tagtgcatgc           292
Gly Leu Glu Arg Lys Cys Phe Cys Lys Lys Val Cys
    70                  75                  80 tagccccgct gtctctgcag tcgcattgct cgtcggctgt gtatctgcag agattgtagt    352
cgcgtgttct cctttgtctg ttgttcatga cgagcttctg ttcttggctt acaggctagt    412
tgagttgctt tcgattatcc ttgcttagaa taagtaataa gtacgcgctg gatacatgct    472
ccagcttagt tagttgttgg gtatttgcaa gctgctgtca tgt                      515
```

<210> SEQ ID NO 44
<211> LENGTH: 80
<212> TYPE: PRT
<213> ORGANISM: artificial
<220> FEATURE:
<223> OTHER INFORMATION: Synthetic Construct

<400> SEQUENCE: 44

Met Ala Pro Ser Arg Arg Met Val Ala Ser Ala Phe Leu Leu Leu Ala
1               5                   10                  15

Ile Leu Val Ala Thr Glu Met Gly Thr Thr Lys Val Ala Glu Ala Arg
            20                  25                  30

His Cys Leu Ser Gln Ser His Arg Phe Lys Gly Met Cys Val Ser Ser
        35                  40                  45

Asn Asn Cys Ala Asn Val Cys Arg Thr Glu Ser Phe Pro Asp Gly Glu
    50                  55                  60

```
Cys Lys Ser His Gly Leu Glu Arg Lys Cys Phe Cys Lys Lys Val Cys
 65                  70                  75                  80

<210> SEQ ID NO 45
<211> LENGTH: 49
<212> TYPE: PRT
<213> ORGANISM: artificial
<220> FEATURE:
<223> OTHER INFORMATION: HXL015 Oryza sativa mature domain aa

<400> SEQUENCE: 45

Arg His Cys Leu Ser Gln Ser His Arg Phe Lys Gly Met Cys Val Ser
 1               5                  10                  15

Ser Asn Asn Cys Ala Asn Val Cys Arg Thr Glu Ser Phe Pro Asp Gly
             20                  25                  30

Glu Cys Lys Ser His Gly Leu Glu Arg Lys Cys Phe Cys Lys Lys Val
         35                  40                  45

Cys

<210> SEQ ID NO 46
<211> LENGTH: 635
<212> TYPE: DNA
<213> ORGANISM: artificial
<220> FEATURE:
<223> OTHER INFORMATION: HXL016 Triticum aestivum na
<220> FEATURE:
<221> NAME/KEY: CDS
<222> LOCATION: (102)..(347)

<400> SEQUENCE: 46
gcacgagtca gtttgctagc cagctaacac agtccccgt atgtagcagc agcagaatag      60
ctcggtccag tacgtcgtct cgggtgaagc agagcagatc g atg gcg ctc tct cgt    116
                                              Met Ala Leu Ser Arg
                                               1               5 cgc atg gcc gcg tcc acc ctc ctg ctc gtc ctc ctc gtc gcc act          164
Arg Met Ala Ala Ser Thr Leu Leu Leu Val Leu Leu Val Ala Thr
                 10                  15                  20 gag atg ggg gcg acg acg acc aag acg gcg gag gcg cgg gac tgc ctg      212
Glu Met Gly Ala Thr Thr Thr Lys Thr Ala Glu Ala Arg Asp Cys Leu
             25                  30                  35 tcg cag agc cac aag ttc aat ggc gcg tgc ctc agc agc agc aac tgc      260
Ser Gln Ser His Lys Phe Asn Gly Ala Cys Leu Ser Ser Ser Asn Cys
         40                  45                  50 gcc ggc gtg tgc cgc acc gag aac ttc ccc gac ggc gag tgc cac acg      308
Ala Gly Val Cys Arg Thr Glu Asn Phe Pro Asp Gly Glu Cys His Thr
     55                  60                  65 cag cac ttc gag cgc aag tgc ttc tgc aag agg gtc tgc tagccgccct       357
Gln His Phe Glu Arg Lys Cys Phe Cys Lys Arg Val Cys
 70                  75                  80 gccggccagc gccgccacgt cccatggtag ctagctagct gctagatcgt ccgtgccttt    417
tgctagatct gttcgtcagt gcgttcgcat tcgtcagtag ttgttcgtgt gagttgactc    477
tgtatcccat aataaagtag gaaatcaacc ggggactcgg tagtttggtt ggccgcacgt    537
agtgtttgtg gctgctttgt gtcgtaaagt gtaataaggt cgtaatttca gcatggacgg    597
acgtgtgcac tgcatcccct ctttctatac atcagcat                            635

<210> SEQ ID NO 47
<211> LENGTH: 82
<212> TYPE: PRT
<213> ORGANISM: artificial
```

```
<220> FEATURE:
<223> OTHER INFORMATION: Synthetic Construct

<400> SEQUENCE: 47

Met Ala Leu Ser Arg Arg Met Ala Ala Ser Thr Leu Leu Leu Val
1               5                   10                  15

Leu Leu Val Ala Thr Glu Met Gly Ala Thr Thr Lys Thr Ala Glu
            20                  25                  30

Ala Arg Asp Cys Leu Ser Gln Ser His Lys Phe Asn Gly Ala Cys Leu
        35                  40                  45

Ser Ser Ser Asn Cys Ala Gly Val Cys Arg Thr Glu Asn Phe Pro Asp
    50                  55                  60

Gly Glu Cys His Thr Gln His Phe Glu Arg Lys Cys Phe Cys Lys Arg
65                  70                  75                  80

Val Cys

<210> SEQ ID NO 48
<211> LENGTH: 49
<212> TYPE: PRT
<213> ORGANISM: artificial
<220> FEATURE:
<223> OTHER INFORMATION: HXL016 Triticum aestivum mature domain aa

<400> SEQUENCE: 48

Arg Asp Cys Leu Ser Gln Ser His Lys Phe Asn Gly Ala Cys Leu Ser
1               5                   10                  15

Ser Ser Asn Cys Ala Gly Val Cys Arg Thr Glu Asn Phe Pro Asp Gly
            20                  25                  30

Glu Cys His Thr Gln His Phe Glu Arg Lys Cys Phe Cys Lys Arg Val
        35                  40                  45

Cys

<210> SEQ ID NO 49
<211> LENGTH: 403
<212> TYPE: DNA
<213> ORGANISM: artificial
<220> FEATURE:
<223> OTHER INFORMATION: HXL017 Zea mays na
<220> FEATURE:
<221> NAME/KEY: CDS
<222> LOCATION: (27)..(281)

<400> SEQUENCE: 49
aaaaacaaat ctccctaatt tcagtc atg aag gcc cag gtc gca gca gca act       53
                             Met Lys Ala Gln Val Ala Ala Ala Thr
                             1               5 gtc ttg gtc ttg ctc ctc cta atc ttt gct gcg gag gct cgt acg tgc      101
Val Leu Val Leu Leu Leu Leu Ile Phe Ala Ala Glu Ala Arg Thr Cys
10                  15                  20                  25 atg tcg cga agc cag gaa cag aaa ggg agg tgc ttt cac gat acg gat      149
Met Ser Arg Ser Gln Glu Gln Lys Gly Arg Cys Phe His Asp Thr Asp
                30                  35                  40 tgt gcc gcc gtc tgc gtc aaa cag agc ttc acc gga ggc tta tgc aac      197
Cys Ala Ala Val Cys Val Lys Gln Ser Phe Thr Gly Gly Leu Cys Asn
            45                  50                  55 ggg cgg ccg ccg ttc aag cag tgc ttc tgc act aag cca tgc aag aga      245
Gly Arg Pro Pro Phe Lys Gln Cys Phe Cys Thr Lys Pro Cys Lys Arg
        60                  65                  70 gag aga gct gat gct aca ctc cgg tcg tca ggc ctc tgatcatgtg           291
Glu Arg Ala Asp Ala Thr Leu Arg Ser Ser Gly Leu
75                  80                  85
```

```
tgcttgatcc acatgacagc gcgactctcg catgtatgcc taggttgatg tgtatgtaat    351
aaataaacaa aatagtaaat gacatgtttt cttaaaaaaa aaaaaaaaaa aa            403
```

```
<210> SEQ ID NO 50
<211> LENGTH: 85
<212> TYPE: PRT
<213> ORGANISM: artificial
<220> FEATURE:
<223> OTHER INFORMATION: Synthetic Construct

<400> SEQUENCE: 50

Met Lys Ala Gln Val Ala Ala Thr Val Leu Val Leu Leu Leu Leu
1               5                   10                  15

Ile Phe Ala Ala Glu Ala Arg Thr Cys Met Ser Arg Ser Gln Glu Gln
            20                  25                  30

Lys Gly Arg Cys Phe His Asp Thr Asp Cys Ala Ala Val Cys Val Lys
        35                  40                  45

Gln Ser Phe Thr Gly Gly Leu Cys Asn Gly Arg Pro Pro Phe Lys Gln
    50                  55                  60

Cys Phe Cys Thr Lys Pro Cys Lys Arg Glu Arg Ala Asp Ala Thr Leu
65                  70                  75                  80

Arg Ser Ser Gly Leu
                85

<210> SEQ ID NO 51
<211> LENGTH: 49
<212> TYPE: PRT
<213> ORGANISM: artificial
<220> FEATURE:
<223> OTHER INFORMATION: HXL017 Zea mays mture domain aa

<400> SEQUENCE: 51

Arg Thr Cys Met Ser Arg Ser Gln Glu Gln Leu Gly Arg Cys Phe His
1               5                   10                  15

Asp Thr Asp Cys Ala Ala Val Cys Val Lys Gln Ser Phe Thr Gly Gly
            20                  25                  30

Leu Cys Asn Gly Arg Pro Pro Phe Lys Gln Cys Pro Cys Thr Lys Pro
        35                  40                  45

Cys

<210> SEQ ID NO 52
<211> LENGTH: 469
<212> TYPE: DNA
<213> ORGANISM: artificial
<220> FEATURE:
<223> OTHER INFORMATION: HXL018 Parthenium argentatum na
<220> FEATURE:
<221> NAME/KEY: CDS
<222> LOCATION: (25)..(258)
<220> FEATURE:
<221> NAME/KEY: misc_feature
<222> LOCATION: (428)..(428)
<223> OTHER INFORMATION: n = A, T, C or G
<220> FEATURE:
<221> NAME/KEY: misc_feature
<222> LOCATION: (433)..(433)
<223> OTHER INFORMATION: n = A, T, C or G
<220> FEATURE:
<221> NAME/KEY: misc_feature
<222> LOCATION: (442)..(442)
<223> OTHER INFORMATION: n = A, T, C or G
<220> FEATURE:
<221> NAME/KEY: misc_feature
<222> LOCATION: (469)..(469)
```

-continued

<223> OTHER INFORMATION: n = A, T, C or G

<400> SEQUENCE: 52

```
ctctctctct ctctctcggt caag atg aag tct tcc atg aag ctg ttt gca              51
                           Met Lys Ser Ser Met Lys Leu Phe Ala
                           1               5 gca tta ttg ctt gtt gtc atg tgt ctg atg gcc aat gaa atg ggt ggt             99
Ala Leu Leu Leu Val Val Met Cys Leu Met Ala Asn Glu Met Gly Gly
 10              15                  20                  25 ccg atg gtg gtg gaa gcg agg aca tgt gag tcg caa agc cac aag ttc            147
Pro Met Val Val Glu Ala Arg Thr Cys Glu Ser Gln Ser His Lys Phe
                 30                  35                  40 aag ggg aca tgt tta agt gac acc aat tgt ggt aat gtg tgc cac tct            195
Lys Gly Thr Cys Leu Ser Asp Thr Asn Cys Gly Asn Val Cys His Ser
             45                  50                  55 gag ggg ttt ccg ggt gga aag tgt cgt ggg ctt cga cgc cgg tgt ttc            243
Glu Gly Phe Pro Gly Gly Lys Cys Arg Gly Leu Arg Arg Arg Cys Phe
         60                  65                  70 tgc acc aag aat tgc tagatcgaac caatatgttt catggccggt tgtttgagag            298
Cys Thr Lys Asn Cys
 75 ttatgtttga gttgtttta aagttcactt gtgtttgtgc gttacatgtt gcctgaataa           358 gtttccaact ccttggtggt tgggtgggtt gggttttcc aaaacaataa tcccgtaccc           418 ttgggggtcn tttcntataa aaangaaaat ggtgaattgg ttcaacccac n                   469
```

<210> SEQ ID NO 53
<211> LENGTH: 78
<212> TYPE: PRT
<213> ORGANISM: artificial
<220> FEATURE:
<223> OTHER INFORMATION: Synthetic Construct

<400> SEQUENCE: 53

```
Met Lys Ser Ser Met Lys Leu Phe Ala Ala Leu Leu Leu Val Val Met
1               5                   10                  15

Cys Leu Met Ala Asn Glu Met Gly Gly Pro Met Val Val Glu Ala Arg
            20                  25                  30

Thr Cys Glu Ser Gln Ser His Lys Phe Lys Gly Thr Cys Leu Ser Asp
        35                  40                  45

Thr Asn Cys Gly Asn Val Cys His Ser Glu Gly Phe Pro Gly Gly Lys
    50                  55                  60

Cys Arg Gly Leu Arg Arg Arg Cys Phe Cys Thr Lys Asn Cys
65                  70                  75
```

<210> SEQ ID NO 54
<211> LENGTH: 47
<212> TYPE: PRT
<213> ORGANISM: artificial
<220> FEATURE:
<223> OTHER INFORMATION: HXL018 Parthenium argentatum mature domain aa

<400> SEQUENCE: 54

```
Arg Thr Cys Glu Ser Gln Ser His Lys Phe Lys Gly Thr Cys Leu Ser
1               5                   10                  15

Asp Thr Asn Cys Gly Asn Val Cys His Ser Glu Gly Phe Pro Gly Gly
            20                  25                  30

Lys Cys Arg Gly Leu Arg Arg Arg Cys Phe Cys Thr Lys Asn Cys
        35                  40                  45
```

```
<210> SEQ ID NO 55
<211> LENGTH: 498
<212> TYPE: DNA
<213> ORGANISM: artificial
<220> FEATURE:
<223> OTHER INFORMATION: HXL019 Nicotiana benthamiana na
<220> FEATURE:
<221> NAME/KEY: CDS
<222> LOCATION: (1)..(258)

<400> SEQUENCE: 55 atg gct aaa tac aca gcc ttc att acc ctc atc ttc tgt ctt ctc ctt      48
Met Ala Lys Tyr Thr Ala Phe Ile Thr Leu Ile Phe Cys Leu Leu Leu
1               5                  10                  15 gtt gct gct act gaa atg caa atg gca gaa gca aaa tac tgc tgg aag      96
Val Ala Ala Thr Glu Met Gln Met Ala Glu Ala Lys Tyr Cys Trp Lys
                20                  25                  30 aaa agt cac aag tgg cat ggg cct tgc cac tat tct tac aaa tgt agc     144
Lys Ser His Lys Trp His Gly Pro Cys His Tyr Ser Tyr Lys Cys Ser
            35                  40                  45 cac cat tgc aag cag tat ttt gga gct gaa tat gga att tgt aag aaa     192
His His Cys Lys Gln Tyr Phe Gly Ala Glu Tyr Gly Ile Cys Lys Lys
        50                  55                  60 tac caa tgg gga cac aaa cat cac cac tgg gca aaa tat gct tgc tat     240
Tyr Gln Trp Gly His Lys His His His Trp Ala Lys Tyr Ala Cys Tyr
65                  70                  75                  80 tgc tat tct cct tgc cat taatcatgag gaattgactt tagagtctca            288
Cys Tyr Ser Pro Cys His
                85 acaattggct tggactgata tatacaaata agaagctgac ttcttgttaa tgcagagaac   348 taaatactgc atcaataatt agttagtgtg attttattgt gtgtttgtgt gtcacaatgt   408 aataagtttt gctaagtcta gcttgacttt tggtcgagct aatagcatat gcctgaacaa   468 ttatgctgct ttcatttaat ttatgttcca                                    498

<210> SEQ ID NO 56
<211> LENGTH: 86
<212> TYPE: PRT
<213> ORGANISM: artificial
<220> FEATURE:
<223> OTHER INFORMATION: Synthetic Construct

<400> SEQUENCE: 56

Met Ala Lys Tyr Thr Ala Phe Ile Thr Leu Ile Phe Cys Leu Leu Leu
1               5                  10                  15

Val Ala Ala Thr Glu Met Gln Met Ala Glu Ala Lys Tyr Cys Trp Lys
                20                  25                  30

Lys Ser His Lys Trp His Gly Pro Cys His Tyr Ser Tyr Lys Cys Ser
            35                  40                  45

His His Cys Lys Gln Tyr Phe Gly Ala Glu Tyr Gly Ile Cys Lys Lys
        50                  55                  60

Tyr Gln Trp Gly His Lys His His His Trp Ala Lys Tyr Ala Cys Tyr
65                  70                  75                  80

Cys Tyr Ser Pro Cys His
                85

<210> SEQ ID NO 57
<211> LENGTH: 58
<212> TYPE: PRT
<213> ORGANISM: artificial
<220> FEATURE:
<223> OTHER INFORMATION: HXL019 Nictoiana benthamiana mature domain aa
```

<400> SEQUENCE: 57

Lys Tyr Cys Trp Lys Lys Ser His Lys Trp His Gly Pro Cys His Tyr
1               5                   10                  15

Ser Tyr Lys Cys Ser His His Cys Lys Gln Tyr Phe Gly Ala Glu Tyr
            20                  25                  30

Gly Ile Cys Lys Lys Tyr Gln Trp Gly His Lys His His Trp Ala
        35                  40                  45

Lys Tyr Ala Cys Tyr Cys Tyr Ser Pro Cys
    50                  55

<210> SEQ ID NO 58
<211> LENGTH: 538
<212> TYPE: DNA
<213> ORGANISM: artificial
<220> FEATURE:
<223> OTHER INFORMATION: HXL020 Triticum aestivum na
<220> FEATURE:
<221> NAME/KEY: CDS
<222> LOCATION: (89)..(331)

<400> SEQUENCE: 58

```
gcacgaggat cagaagccat agcttgtttc acctaaagag agaaaaaaag gctttgctcc     60
atcaacctac ctaccccac agaagcaa atg gag ttc aag ccc aag gcg acc        112
                              Met Glu Phe Lys Pro Lys Ala Thr
                                1               5 gtg tgc gcg atg atg ctg gtg ctg ctc ctg ctt tcc tcc tac agc ggc      160
Val Cys Ala Met Met Leu Val Leu Leu Leu Leu Ser Ser Tyr Ser Gly
 10              15                  20 ggc ggt ggc atc ggc gtg gcg gag gcg cgc att tgc acg ggg aag agc      208
Gly Gly Gly Ile Gly Val Ala Glu Ala Arg Ile Cys Thr Gly Lys Ser
25              30                  35                  40 cag cac cac tcg ttc ccg tgc gtc tcg gac aag agc tgc acc aag acg      256
Gln His His Ser Phe Pro Cys Val Ser Asp Lys Ser Cys Thr Lys Thr
            45                  50                  55 tgc ctc agc gag cac ggc gca aaa tgg acg gcc ggc tac tgc aaa atc      304
Cys Leu Ser Glu His Gly Ala Lys Trp Thr Ala Gly Tyr Cys Lys Ile
        60                  65                  70 agg cgc tgc acc tgc cag agg gag tgc tagggcagac gctccgcgcg            351
Arg Arg Cys Thr Cys Gln Arg Glu Cys
    75                  80 cgagctcccc caccccgcc ccgtccatgg cgccgtctgt caaacgaagc cacctatgta     411
tcttaagtct taactaccat gtacccactc gccgcctctg tcaggagatg taataaaacg    471
tggcgcggcg accgccggc gcgtcaccgc tgtacgtagc atgatgcatg ccacgcgttg    531
cttttgt                                                              538
```

<210> SEQ ID NO 59
<211> LENGTH: 81
<212> TYPE: PRT
<213> ORGANISM: artificial
<220> FEATURE:
<223> OTHER INFORMATION: Synthetic Construct

<400> SEQUENCE: 59

Met Glu Phe Lys Pro Lys Ala Thr Val Cys Ala Met Met Leu Val Leu
1               5                   10                  15

Leu Leu Leu Ser Ser Tyr Ser Gly Gly Gly Gly Ile Gly Val Ala Glu
            20                  25                  30

Ala Arg Ile Cys Thr Gly Lys Ser Gln His His Ser Phe Pro Cys Val

-continued

```
                  35                  40                  45

Ser Asp Lys Ser Cys Thr Lys Thr Cys Leu Ser Glu His Gly Ala Lys
     50                  55                  60

Trp Thr Ala Gly Tyr Cys Lys Ile Arg Arg Cys Thr Cys Gln Arg Glu
65                  70                  75                  80

Cys

<210> SEQ ID NO 60
<211> LENGTH: 48
<212> TYPE: PRT
<213> ORGANISM: artificial
<220> FEATURE:
<223> OTHER INFORMATION: HXL020 Triticum aestivum mature domain aa

<400> SEQUENCE: 60

Arg Ile Cys Thr Gly Lys Ser Gln His His Ser Phe Pro Cys Val Ser
1               5                   10                  15

Asp Lys Ser Cys Thr Lys Thr Cys Leu Ser Glu His Gly Ala Lys Trp
                20                  25                  30

Thr Ala Gly Tyr Gly Lys Ile Arg Arg Cys Thr Cys Gln Arg Glu Cys
            35                  40                  45

<210> SEQ ID NO 61
<211> LENGTH: 461
<212> TYPE: DNA
<213> ORGANISM: artificial
<220> FEATURE:
<223> OTHER INFORMATION: HXL021 Arachis hypogaea na
<220> FEATURE:
<221> NAME/KEY: CDS
<222> LOCATION: (44)..(268)
<220> FEATURE:
<221> NAME/KEY: misc_feature
<222> LOCATION: (305)..(305)
<223> OTHER INFORMATION: n = A, T, C or G
<220> FEATURE:
<221> NAME/KEY: misc_feature
<222> LOCATION: (319)..(319)
<223> OTHER INFORMATION: n = A, T, C or G
<220> FEATURE:
<221> NAME/KEY: misc_feature
<222> LOCATION: (357)..(357)
<223> OTHER INFORMATION: n = A, T, C or G
<220> FEATURE:
<221> NAME/KEY: misc_feature
<222> LOCATION: (372)..(372)
<223> OTHER INFORMATION: n = A, T, C or G
<220> FEATURE:
<221> NAME/KEY: misc_feature
<222> LOCATION: (400)..(400)
<223> OTHER INFORMATION: n = A, T, C or G
<220> FEATURE:
<221> NAME/KEY: misc_feature
<222> LOCATION: (406)..(406)
<223> OTHER INFORMATION: n = A, T, C or G
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (443)..(443)
<223> OTHER INFORMATION: n = A, T, C or G
<220> FEATURE:
<221> NAME/KEY: misc_feature
<222> LOCATION: (452)..(452)
<223> OTHER INFORMATION: n = A, T, C or G
<220> FEATURE:
<221> NAME/KEY: misc_feature
<222> LOCATION: (455)..(455)
<223> OTHER INFORMATION: n = A, T, C or G
```

<400> SEQUENCE: 61

```
gatatcaata tatctatata gctgtttact ttaatcataa gcc atg gcg ggg aaa        55
                                             Met Ala Gly Lys
                                             1 tct cta acc ggg ttt tgc ttc atc ctc ctc ctc gtt gtt gct cag           103
Ser Leu Thr Gly Phe Cys Phe Ile Leu Leu Leu Val Val Ala Gln
5                   10                  15                  20 gaa atg gtg gtc caa agt gag gca gca acg tgt gag aac ctg gcg gat       151
Glu Met Val Val Gln Ser Glu Ala Ala Thr Cys Glu Asn Leu Ala Asp
            25                  30                  35 acc tac agg gga cca tgc ttc acc acc gga agc tgc gac gac cac tgc       199
Thr Tyr Arg Gly Pro Cys Phe Thr Thr Gly Ser Cys Asp Asp His Cys
        40                  45                  50 aag aac aag gag cac ctg ctc agc ggc cgc tgc cgc gac gat ttc cgc       247
Lys Asn Lys Glu His Leu Leu Ser Gly Arg Cys Arg Asp Asp Phe Arg
    55                  60                  65 tgt tgg tgc acc aga aac tgt taaattacgc atcatgagct acgtacgcag          298
Cys Trp Cys Thr Arg Asn Cys
70                  75 atcgatncaa gatgctggat ntgagctagc tagctaagga gcatatatat acataaatna     358
tacttctaag ctancactgc atttaaatat gttaccaaaa anttttgnaa gggtggaatt     418
gnaatgccct attgcctaat acatnacggg ccanttntgt tcg                       461
```

<210> SEQ ID NO 62
<211> LENGTH: 75
<212> TYPE: PRT
<213> ORGANISM: artificial
<220> FEATURE:
<223> OTHER INFORMATION: Synthetic Construct

<400> SEQUENCE: 62

```
Met Ala Gly Lys Ser Leu Thr Gly Phe Cys Phe Ile Leu Leu Leu Leu
1               5                   10                  15

Val Val Ala Gln Glu Met Val Val Gln Ser Glu Ala Ala Thr Cys Glu
            20                  25                  30

Asn Leu Ala Asp Thr Tyr Arg Gly Pro Cys Phe Thr Thr Gly Ser Cys
        35                  40                  45

Asp Asp His Cys Lys Asn Lys Glu His Leu Leu Ser Gly Arg Cys Arg
    50                  55                  60

Asp Asp Phe Arg Cys Trp Cys Thr Arg Asn Cys
65                  70                  75
```

<210> SEQ ID NO 63
<211> LENGTH: 47
<212> TYPE: PRT
<213> ORGANISM: artificial
<220> FEATURE:
<223> OTHER INFORMATION: HXL021 Arachis hypogaea mature domain aa

<400> SEQUENCE: 63

```
Ala Thr Cys Glu Asn Leu Ala Asp Thr Tyr Arg Gly Pro Cys Phe Thr
1               5                   10                  15

Thr Gly Ser Cys Asp Asp His Cys Lys Asn Lys Glu His Leu Leu Ser
            20                  25                  30

Gly Arg Cys Arg Asp Asp Phe Arg Cys Trp Cys Thr Arg Asn Cys
        35                  40                  45
```

<210> SEQ ID NO 64

-continued

```
<211> LENGTH: 464
<212> TYPE: DNA
<213> ORGANISM: artificial
<220> FEATURE:
<223> OTHER INFORMATION: HXL022 Cyamopsis tetragonoloba na
<220> FEATURE:
<221> NAME/KEY: misc_feature
<222> LOCATION: (1)..(2)
<223> OTHER INFORMATION: n = A, T, C or G
<220> FEATURE:
<221> NAME/KEY: CDS
<222> LOCATION: (32)..(253)

<400> SEQUENCE: 64
nnaagaatta attaagtgaa tttaagcaat t atg gag aag aaa tca gtc gct         52
                                   Met Glu Lys Lys Ser Val Ala
                                   1               5 ggt ttt tgc tgc ctc ctc ctt gtc ctc ttt gtt gct cag gaa ata gtg      100
Gly Phe Cys Cys Leu Leu Leu Val Leu Phe Val Ala Gln Glu Ile Val
        10                  15                  20 gtg aaa aca gag gca aga aca tgt gag agt ccg gca gac aca tac agg      148
Val Lys Thr Glu Ala Arg Thr Cys Glu Ser Pro Ala Asp Thr Tyr Arg
 25                  30                  35 gga ccc tgt ttc act gag ggt agc tgc gat gat cat tgc aag aac aaa      196
Gly Pro Cys Phe Thr Glu Gly Ser Cys Asp Asp His Cys Lys Asn Lys
 40                  45                  50                  55 gaa cac tta atc agt gga aca tgc aaa cag tta gcc tgc tgg tgc acc      244
Glu His Leu Ile Ser Gly Thr Cys Lys Gln Leu Ala Cys Trp Cys Thr
                 60                  65                  70 aga aac tgt taattaatta ctaatattat tggatgcagt acagtgcctt              293
Arg Asn Cys aattaattat tactatcaat aaataaatta ctgtatacaa ataacagcac ttaaactgct    353
tcttaattat gtatcggtgc cactatacat actcatatat atgtactgcg tacataacac    413
ctctgttatg tactttatgt taaacaaata aacgatcttg ttattgcttg c             464

<210> SEQ ID NO 65
<211> LENGTH: 74
<212> TYPE: PRT
<213> ORGANISM: artificial
<220> FEATURE:
<223> OTHER INFORMATION: Synthetic Construct

<400> SEQUENCE: 65

Met Glu Lys Lys Ser Val Ala Gly Phe Cys Cys Leu Leu Leu Val Leu
1               5                  10                  15

Phe Val Ala Gln Glu Ile Val Val Lys Thr Glu Ala Arg Thr Cys Glu
            20                  25                  30

Ser Pro Ala Asp Thr Tyr Arg Gly Pro Cys Phe Thr Glu Gly Ser Cys
        35                  40                  45

Asp Asp His Cys Lys Asn Lys Glu His Leu Ile Ser Gly Thr Cys Lys
    50                  55                  60

Gln Leu Ala Cys Trp Cys Thr Arg Asn Cys
65                  70

<210> SEQ ID NO 66
<211> LENGTH: 46
<212> TYPE: PRT
<213> ORGANISM: artificial
<220> FEATURE:
<223> OTHER INFORMATION: HXL022 Cyamopsis tetragonoloba mature domain aa

<400> SEQUENCE: 66
```

```
Arg Thr Cys Gly Ser Pro Ala Asp Thr Tyr Arg Gly Pro Cys Phe Thr
1               5                   10                  15
Glu Gly Ser Cys Asp Asp His Cys Lys Asn Lys Glu His Leu Ile Ser
            20                  25                  30
Gly Thr Cys Lys Gln Leu Ala Cys Trp Cys Thr Arg Asn Cys
        35                  40                  45

<210> SEQ ID NO 67
<211> LENGTH: 681
<212> TYPE: DNA
<213> ORGANISM: artificial
<220> FEATURE:
<223> OTHER INFORMATION: HXL023 Triticum aestivum na
<220> FEATURE:
<221> NAME/KEY: CDS
<222> LOCATION: (83)..(328)

<400> SEQUENCE: 67
gcacgaggct tgctacgta gcagcagcag ggtagctcct cagtccaata cgtcgtctcg      60
agtgaagaag atcagcagct cg atg gcg ctc tct cgt cgc agc gcc gca tcc     112
                        Met Ala Leu Ser Arg Arg Ser Ala Ala Ser
                         1               5                  10 gcc ctc ctg ctt ctc gtg ctc ctc gtg gcc aca gag atg ggg acg acg     160
Ala Leu Leu Leu Leu Val Leu Leu Val Ala Thr Glu Met Gly Thr Thr
                15                  20                  25 acg acc aag ctg gcg gag gcg cgg gac tgc ctg tcg cag agt cac aac     208
Thr Thr Lys Leu Ala Glu Ala Arg Asp Cys Leu Ser Gln Ser His Asn
            30                  35                  40 ttc aag ggc gcc tgc ctc agc agc agc aac tgc gcc ggc gtc tgc cac     256
Phe Lys Gly Ala Cys Leu Ser Ser Ser Asn Cys Ala Gly Val Cys His
        45                  50                  55 acc gag agc ttc ccc ggc ggc gag tgc cac acg cag cac ttc gag cgc     304
Thr Glu Ser Phe Pro Gly Gly Glu Cys His Thr Gln His Phe Glu Arg
    60                  65                  70 aag tgc ttc tgc aag agg gtc tgc tagcccgcct gctcgccccg ccgccctgc     358
Lys Cys Phe Cys Lys Arg Val Cys
75                  80 cggccagcgc cgagacgtcc gatcatccgt gccgtgcctc cacgttcgtc agtagtagta   418
tttctgttcc gtgacgttag atagttcatc cgtgccgtta gctactttg ttctgttcgt    478 ccgtgtgtcc ctcttagtat agaatagaac tataataaag tagaaaacca atcggggtct   538
cggttgttta gttcgctgta cgcctgtttg tgcctgattt gtgtgtggtg atgtactaaa   598
tatggatcgt tatttcagca tgcaggacat gtcaatgcag tccccctctc tctcaaggcg   658
ttaacatgac tagtaacaaa gag                                           681

<210> SEQ ID NO 68
<211> LENGTH: 82
<212> TYPE: PRT
<213> ORGANISM: artificial
<220> FEATURE:
<223> OTHER INFORMATION: Synthetic Construct

<400> SEQUENCE: 68

Met Ala Leu Ser Arg Arg Ser Ala Ala Ser Ala Leu Leu Leu Leu Val
1               5                   10                  15
Leu Leu Val Ala Thr Glu Met Gly Thr Thr Thr Thr Lys Leu Ala Glu
            20                  25                  30
Ala Arg Asp Cys Leu Ser Gln Ser His Asn Phe Lys Gly Ala Cys Leu
        35                  40                  45
```

Ser Ser Ser Asn Cys Ala Gly Val Cys His Thr Glu Ser Phe Pro Gly
            50                  55                  60

Gly Glu Cys His Thr Gln His Phe Glu Arg Lys Cys Phe Cys Lys Arg
 65                  70                  75                  80

Val Cys

<210> SEQ ID NO 69
<211> LENGTH: 49
<212> TYPE: PRT
<213> ORGANISM: artificial
<220> FEATURE:
<223> OTHER INFORMATION: HXL023 Tricticum aestivum mature domain aa

<400> SEQUENCE: 69

Arg Asp Cys Leu Ser Gln Ser His Asn Phe Lys Gly Ala Cys Leu Ser
 1               5                  10                  15

Ser Ser Asn Cys Ala Gly Val Cys His Thr Glu Ser Phe Pro Gly Gly
                20                  25                  30

Glu Cys His Thr Gln His Phe Glu Arg Lys Cys Phe Cys Lys Arg Val
             35                  40                  45

Cys

<210> SEQ ID NO 70
<211> LENGTH: 47
<212> TYPE: PRT
<213> ORGANISM: artificial
<220> FEATURE:
<223> OTHER INFORMATION: Amino acid sequence of HXP4 (NaD2 Loop1B
      [NaD2L1B] in NaD1)

<400> SEQUENCE: 70

Arg Glu Cys Lys Thr Glu Ser His Arg Phe Lys Gly Pro Cys Ile Thr
 1               5                  10                  15

Lys Pro Pro Cys Arg Lys Ala Cys Ile Ser Glu Lys Phe Thr Asp Gly
                20                  25                  30

His Cys Ser Lys Ile Leu Arg Arg Cys Leu Cys Thr Lys Pro Cys
             35                  40                  45

<210> SEQ ID NO 71
<211> LENGTH: 47
<212> TYPE: PRT
<213> ORGANISM: artificial
<220> FEATURE:
<223> OTHER INFORMATION: Amino acid sequence of HXP34 (Zea2 Loop1B
      [Zea2L1B] in NaD1)

<400> SEQUENCE: 71

Arg Glu Cys Lys Thr Glu Ser Gln His His Ser Phe Pro Cys Ile Thr
 1               5                  10                  15

Lys Pro Pro Cys Arg Lys Ala Cys Ile Ser Glu Lys Phe Thr Asp Gly
                20                  25                  30

His Cys Ser Lys Ile Leu Arg Arg Cys Leu Cys Thr Lys Pro Cys
             35                  40                  45

<210> SEQ ID NO 72
<211> LENGTH: 47
<212> TYPE: PRT
<213> ORGANISM: artificial
<220> FEATURE:
<223> OTHER INFORMATION: Amino acid sequence of HXP35 (PsD1 Loop1B
      [PsDL1B] in NaD1)

<400> SEQUENCE: 72

```
Arg Glu Cys Lys Thr Glu Ser Asp Thr Tyr Arg Gly Val Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
            35                  40                  45
```

<210> SEQ ID NO 73
<211> LENGTH: 46
<212> TYPE: PRT
<213> ORGANISM: artificial
<220> FEATURE:
<223> OTHER INFORMATION: Amino acid sequence of HXP37 (VrD1 Loop1B
      [VrD1l1B] in NaD1)

<400> SEQUENCE: 73

```
Arg Glu Cys Lys Thr Glu Ser Glu Gly Trp Gly Lys Cys Ile Thr Lys
1               5                   10                  15

Pro Pro Cys Arg Lys Ala Cys Ile Ser Glu Lys Phe Thr Asp Gly His
            20                  25                  30

Cys Ser Lys Ile Leu Arg Arg Cys Leu Cys Thr Lys Pro Cys
            35                  40                  45
```

<210> SEQ ID NO 74
<211> LENGTH: 47
<212> TYPE: PRT
<213> ORGANISM: artificial
<220> FEATURE:
<223> OTHER INFORMATION: Amino acid sequence of HXP58 (DMAMP1 Loop1B
      [DMAMPL1B] in NaD1)

<400> SEQUENCE: 74

```
Arg Glu Cys Lys Thr Glu Ser Lys Thr Trp Ser Gly Asn Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
            35                  40                  45
```

<210> SEQ ID NO 75
<211> LENGTH: 49
<212> TYPE: PRT
<213> ORGANISM: artificial
<220> FEATURE:
<223> OTHER INFORMATION: Amino acid sequence of HXP72 (NaD2 Loop1B
      [NaD2L1B] in PhD2)

<400> SEQUENCE: 75

```
Gly Thr Cys Lys Ala Glu Cys His Arg Phe Lys Gly Pro Cys Ile Asn
1               5                   10                  15

Lys Ala Pro Cys Val Lys Cys Cys Lys Ala Gln Pro Glu Lys Phe Thr
            20                  25                  30

Asp Gly His Cys Ser Lys Ile Leu Arg Arg Cys Leu Cys Thr Lys Pro
            35                  40                  45

Cys
```

<210> SEQ ID NO 76
<211> LENGTH: 47
<212> TYPE: PRT
<213> ORGANISM: artificial
<220> FEATURE:
<223> OTHER INFORMATION: Amino acid sequence of HXP91 (msDeF1 Loop1B

[MsDef1L1b] in NaD1)

<400> SEQUENCE: 76

```
Arg Glu Cys Lys Thr Glu Ser Asp Lys Tyr Arg Gly Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 77
<211> LENGTH: 47
<212> TYPE: PRT
<213> ORGANISM: artificial
<220> FEATURE:
<223> OTHER INFORMATION: amino acid sequence of HXP92 (SoD1 Loop1B [SoD1L1B] in NaD1)

<400> SEQUENCE: 77

```
Arg Glu Cys Lys Thr Glu Ser Lys Thr Phe Lys Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 78
<211> LENGTH: 47
<212> TYPE: PRT
<213> ORGANISM: artificial
<220> FEATURE:
<223> OTHER INFORMATION: Amino acid sequence of HXP95 (NaD2 Loop1B [NaD2L1B] in NaD1

<400> SEQUENCE: 78

```
Lys Asp Cys Lys Arg Glu Ser His Arg Phe Lys Gly Pro Cys Ile Thr
1               5                   10                  15

Lys Leu Pro Cys Arg Arg Ala Cys Ile Ser Glu Lys Phe Ala Asp Gly
            20                  25                  30

His Cys Ser Lys Ile Leu Arg Arg Cys Leu Cys Thr Lys Pro Cys
        35                  40                  45
```

<210> SEQ ID NO 79
<211> LENGTH: 48
<212> TYPE: PRT
<213> ORGANISM: artificial
<220> FEATURE:
<223> OTHER INFORMATION: TPP3 backbone with NaD2 Loop1B

<400> SEQUENCE: 79

```
Gln Gln Ile Cys Lys Ala Pro Ser His Arg Phe Lys Gly Pro Cys Phe
1               5                   10                  15

Met Asp Ser Ser Cys Arg Lys Tyr Cys Ile Lys Glu Lys Phe Thr Gly
            20                  25                  30

Gly His Cys Ser Lys Leu Gln Arg Lys Cys Leu Cys Thr Lys Pro Cys
        35                  40                  45
```

<210> SEQ ID NO 80
<211> LENGTH: 84
<212> TYPE: PRT
<213> ORGANISM: artificial
<220> FEATURE:
<223> OTHER INFORMATION: VP42 full length aa

<400> SEQUENCE: 80

Met Glu Ser Thr Ser Arg His Met Val Ala Ser Val Leu Leu Val Leu
1               5                   10                  15

Leu Leu Leu Val Ala Thr Glu Met Gly Thr Thr Arg Val Ala Glu Ala
                20                  25                  30

Arg His Arg His Cys Glu Ser Gln Ser His Arg Tyr Arg Gly Ala Cys
            35                  40                  45

Trp Arg Asp Asp Asn Cys Lys His Val Cys Asn Thr Glu Gly Phe Pro
        50                  55                  60

Ser Gly Lys Cys Lys Phe His Gly Phe Glu Ser Lys Cys Val Cys Thr
65                  70                  75                  80

Lys Pro Cys Gln

<210> SEQ ID NO 81
<211> LENGTH: 49
<212> TYPE: PRT
<213> ORGANISM: artificial
<220> FEATURE:
<223> OTHER INFORMATION: VP42 mature domain

<400> SEQUENCE: 81

Arg His Cys Glu Ser Gln Ser His Arg Tyr Arg Gly Ala Cys Trp Arg
1               5                   10                  15

Asp Asp Asn Cys Lys His Val Cys Asn Thr Glu Gly Phe Pro Ser Gly
                20                  25                  30

Lys Cys Lys Phe His Gly Phe Glu Ser Lys Cys Val Cys Thr Lys Pro
            35                  40                  45

Cys

<210> SEQ ID NO 82
<211> LENGTH: 79
<212> TYPE: PRT
<213> ORGANISM: artificial
<220> FEATURE:
<223> OTHER INFORMATION: VP45 full length aa

<400> SEQUENCE: 82

Met Ala Ala Ser Asn Lys Ile Ala Ala Ala His Val Val Phe Val Leu
1               5                   10                  15

Ala Leu Leu Leu Val Ala Tyr Arg Ala Glu Ala Thr Val Cys Met Arg
                20                  25                  30

His Asn Asn Phe Tyr His Gly Pro Cys Met Ser Asn Lys Asp Cys Ala
            35                  40                  45

Asn Ser Cys Val Gln His Asn Leu Gly Val Gly Gly Tyr Cys Arg Gly
        50                  55                  60

Lys Ile Pro Phe Asn Lys Glu Cys Met Cys Thr Phe Glu Cys Pro
65                  70                  75

<210> SEQ ID NO 83
<211> LENGTH: 51
<212> TYPE: PRT
<213> ORGANISM: artificial
<220> FEATURE:
<223> OTHER INFORMATION: VP45 mature domain

<400> SEQUENCE: 83

Thr Val Cys Met Arg His Asn Asn Phe Tyr His Gly Pro Cys Met Ser
1               5                   10                  15

```
Asn Lys Asp Cys Ala Asn Ser Cys Val Gln His Asn Leu Gly Val Gly
            20                  25                  30

Gly Tyr Cys Arg Gly Lys Ile Pro Phe Asn Lys Glu Cys Met Cys Thr
            35                  40                  45

Phe Glu Cys
    50

<210> SEQ ID NO 84
<211> LENGTH: 74
<212> TYPE: PRT
<213> ORGANISM: artificial
<220> FEATURE:
<223> OTHER INFORMATION: VP135 full length aa

<400> SEQUENCE: 84

Met Glu Arg Lys Ala Phe Gly Leu Ile Phe Leu Ile Leu Thr Val Leu
1               5                   10                  15

Ala Ser Gln Asn Met Leu Leu Pro Thr Glu Ala Arg Ile Cys Ser Ser
            20                  25                  30

Leu Ser His Gly Tyr Lys Gly Pro Cys Ala Ser Asp His Asn Cys Ala
            35                  40                  45

Leu Val Cys Arg Asn Glu Gly Phe Ser Gly Gly Asp Cys His Gly Leu
        50                  55                  60

Arg Arg Arg Cys Phe Cys Thr Lys Ala Cys
65                  70

<210> SEQ ID NO 85
<211> LENGTH: 47
<212> TYPE: PRT
<213> ORGANISM: artificial
<220> FEATURE:
<223> OTHER INFORMATION: VP135 mature domain

<400> SEQUENCE: 85

Arg Ile Cys Ser Ser Leu Ser His Gly Tyr Lys Gly Pro Cys Ala Ser
1               5                   10                  15

Asp His Asn Cys Ala Leu Val Cys Arg Asn Glu Gly Phe Ser Gly Gly
            20                  25                  30

Asp Cys His Gly Leu Arg Arg Arg Cys Phe Cys Thr Lys Ala Cys
            35                  40                  45

<210> SEQ ID NO 86
<211> LENGTH: 5
<212> TYPE: PRT
<213> ORGANISM: artificial
<220> FEATURE:
<223> OTHER INFORMATION: MGEV Linker
<220> FEATURE:
<221> NAME/KEY: MISC_FEATURE
<222> LOCATION: (1)..(1)
<223> OTHER INFORMATION: X1 = E or D
<220> FEATURE:
<221> NAME/KEY: MISC_FEATURE
<222> LOCATION: (2)..(2)
<223> OTHER INFORMATION: X2 = E or D
<220> FEATURE:
<221> NAME/KEY: MISC_FEATURE
<222> LOCATION: (3)..(3)
<223> OTHER INFORMATION: X3 = K or R
<220> FEATURE:
<221> NAME/KEY: MISC_FEATURE
<222> LOCATION: (4)..(4)
<223> OTHER INFORMATION: X4 = K or R
<220> FEATURE:
<221> NAME/KEY: MISC_FEATURE
<222> LOCATION: (5)..(5)
```

<223> OTHER INFORMATION: X4 = N or Q

<400> SEQUENCE: 86

Xaa Xaa Xaa Xaa Xaa
1               5

<210> SEQ ID NO 87
<211> LENGTH: 629
<212> TYPE: DNA
<213> ORGANISM: artificial
<220> FEATURE:
<223> OTHER INFORMATION: HXL032 Triticum aestirum

<400> SEQUENCE: 87

```
gcacgaggct agacaggaca gcctatattg acgtagacgc agcaggagca gcagcagcga    60
actctgtcag ttctctagca tctccggtga agcaagcaag cagagagatg gcgtcccctc   120
gtcgcatggc cgccgcgccc gccgtcctcc tcctcgtcct gctcctcctc gtcgccacgg   180
agatggggac gatgaagacg gcggaggccc ggacgtgcct gtcgcagagc acaagttca   240
agggcacctg cctcagcaac agcaactgcg ccggcgtgtg ccgcaccgag aacttccccg   300
acggcgagtg caactcccac cgcctcgagc gcaagtgctt ctgcaagcgc acctgctaag   360
caagcccagt ccgcgctact ggctctggct agctagactg ctagatcagc agccatgccg   420
tcagttagat ctgttcgtcc ctactttgt ttccgtttgc tttacgttgc tcttggggat    480
gactgaaaat aaagtagcta cctacatcct ctgcattggc tgttccactg catgttgtct   540
aagtgtttct ggctttagtt tgtgctgttg atgtaataac gatgccacta acaatttggc   600
ttctatgtgt tgtgttgaaa cttggaatc                                    629
```

<210> SEQ ID NO 88
<211> LENGTH: 83
<212> TYPE: PRT
<213> ORGANISM: artificial
<220> FEATURE:
<223> OTHER INFORMATION: HXL032 Triticum aestirum

<400> SEQUENCE: 88

Met Ala Ser Pro Arg Arg Met Ala Ala Ala Pro Ala Val Leu Leu Leu
1               5                   10                  15

Val Leu Leu Leu Leu Val Ala Thr Glu Met Gly Thr Met Lys Thr Ala
                20                  25                  30

Glu Ala Arg Thr Cys Leu Ser Gln Ser His Lys Phe Lys Gly Thr Cys
            35                  40                  45

Leu Ser Asn Ser Asn Cys Ala Gly Val Cys Arg Thr Glu Asn Phe Pro
        50                  55                  60

Asp Gly Glu Cys Asn Ser His Arg Leu Glu Arg Lys Cys Phe Cys Lys
65                  70                  75                  80

Arg Thr Cys

<210> SEQ ID NO 89
<211> LENGTH: 49
<212> TYPE: PRT
<213> ORGANISM: artificial
<220> FEATURE:
<223> OTHER INFORMATION: HXL032 Triticum aestirum

<400> SEQUENCE: 89

Arg Thr Cys Leu Ser Gln Ser His Lys Phe Lys Gly Thr Cys Leu Ser
1               5                   10                  15

Asn Ser Asn Cys Ala Gly Val Cys Arg Thr Glu Asn Phe Pro Asp Gly
            20                  25                  30

Glu Cys Asn Ser His Arg Leu Glu Arg Lys Cys Phe Cys Lys Arg Thr
            35                  40                  45

Cys

<210> SEQ ID NO 90
<211> LENGTH: 469
<212> TYPE: DNA
<213> ORGANISM: artificial
<220> FEATURE:
<223> OTHER INFORMATION: HXL033 Parthenium argentatum
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t

<400> SEQUENCE: 90
ctctctctct ctctctcggt caagatgaag tcttccatga agctgtttgc agcattattg      60
cttgttgtca tgtgtctgat ggccaatgaa atgggtggtc cgatggtggt ggaagcgagg     120
acatgtgagt cgcaaagcca caagttcaag gggacatgtt taagtgacac caattgtggt     180
aatgtgtgcc actctgaggg gtttccgggt ggaaagtgtc gtgggcttcg acgccggtgt     240
ttctgcacca agaattgcta gatcgaacca atatgtttca tggccggttg tttgagagtt     300
atgtttgagt tgttttttaaa gttcacttgt gtttgtgcgt tacatgttgc ctgaataagt     360
ttccaactcc ttggtggttg ggtgggttgg gttttttccaa aacaataatc ccgtaccctt     420
gggggtcntt tcntataaaa angaaaatgg tgaattggtt caacccacn               469

<210> SEQ ID NO 91
<211> LENGTH: 78
<212> TYPE: PRT
<213> ORGANISM: artificial
<220> FEATURE:
<223> OTHER INFORMATION: HXL033 Parthenium argentatum

<400> SEQUENCE: 91

Met Lys Ser Ser Met Lys Leu Phe Ala Ala Leu Leu Leu Val Val Met
1               5                   10                  15

Cys Leu Met Ala Asn Glu Met Gly Gly Pro Met Val Val Glu Ala Arg
            20                  25                  30

Thr Cys Glu Ser Gln Ser His Lys Phe Lys Gly Thr Cys Leu Ser Asp
            35                  40                  45

Thr Asn Cys Gly Asn Val Cys His Ser Glu Gly Phe Pro Gly Gly Lys
        50                  55                  60

Cys Arg Gly Leu Arg Arg Arg Cys Phe Cys Thr Lys Asn Cys
65                  70                  75

<210> SEQ ID NO 92
<211> LENGTH: 47
<212> TYPE: PRT

<213> ORGANISM: artificial
<220> FEATURE:
<223> OTHER INFORMATION: HXL033 Parthenium argentatum

<400> SEQUENCE: 92

| Arg | Thr | Cys | Glu | Ser | Gln | Ser | His | Lys | Phe | Lys | Gly | Thr | Cys | Leu | Ser |
|---|---|---|---|---|---|---|---|---|---|---|---|---|---|---|---|
| 1 | | | | 5 | | | | | 10 | | | | | 15 | |

| Asp | Thr | Asn | Cys | Gly | Asn | Val | Cys | His | Ser | Glu | Gly | Phe | Pro | Gly | Gly |
|---|---|---|---|---|---|---|---|---|---|---|---|---|---|---|---|
| | | | 20 | | | | 25 | | | | | 30 | | | |

| Lys | Cys | Arg | Gly | Leu | Arg | Arg | Arg | Cys | Phe | Cys | Thr | Lys | Asn | Cys |
|---|---|---|---|---|---|---|---|---|---|---|---|---|---|---|
| | | 35 | | | | 40 | | | | | 45 | | | |

<210> SEQ ID NO 93
<211> LENGTH: 494
<212> TYPE: DNA
<213> ORGANISM: artificial
<220> FEATURE:
<223> OTHER INFORMATION: HXL034 Nicotiana benthamiana
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t

<400> SEQUENCE: 93

```
ctaagctgcc tctctctgtc aaaaaatact tttgtctgtg aaaatggcaa aatccatgcg      60
cttctttgcc actgtgttac ttctggcaat gcttgtcatg ctactgaga tgggaccaat     120
gacagttgcc gaggcaagac gttgcgagtc gaaaagccaa cgttttaagg gaccatgtgt    180
tagagtgaaa aattgtgccg ccgtttgtga gaccgaagga ttttccggtg gtgactgccg    240
tggactccgt cgccgttgtt tttgtactag gccatgctaa gaatgttact atatgttata   300
tatgtaaaac ctgaatttga gaaactattg aataagcatt atgattgttc aacgattaac   360
gtgctagttt gttactaatt aaactatcgt gatctttgac cgttatgcaa atataangna  420
catttaaggg ggttgtgatt tccaagggng aattcccgtg ttccgcaacg ttatggataa    480
attctccttc aacc                                                      494
```

<210> SEQ ID NO 94
<211> LENGTH: 78
<212> TYPE: PRT
<213> ORGANISM: artificial
<220> FEATURE:
<223> OTHER INFORMATION: HXL034 Nicotiana benthamiana

<400> SEQUENCE: 94

| Met | Ala | Lys | Ser | Met | Arg | Phe | Phe | Ala | Thr | Val | Leu | Leu | Ala | Met |
|---|---|---|---|---|---|---|---|---|---|---|---|---|---|---|
| 1 | | | | 5 | | | | | 10 | | | | | 15 |

| Leu | Val | Met | Ala | Thr | Glu | Met | Gly | Pro | Met | Thr | Val | Ala | Glu | Ala | Arg |
|---|---|---|---|---|---|---|---|---|---|---|---|---|---|---|---|
| | | | 20 | | | | 25 | | | | | 30 | | | |

| Arg | Cys | Glu | Ser | Lys | Ser | Gln | Arg | Phe | Lys | Gly | Pro | Cys | Val | Arg | Val |
|---|---|---|---|---|---|---|---|---|---|---|---|---|---|---|---|
| | | 35 | | | | 40 | | | | | 45 | | | | |

| Lys | Asn | Cys | Ala | Ala | Val | Cys | Glu | Thr | Glu | Gly | Phe | Ser | Gly | Gly | Asp |
|---|---|---|---|---|---|---|---|---|---|---|---|---|---|---|---|
| | 50 | | | | 55 | | | | | 60 | | | | | |

| Cys | Arg | Gly | Leu | Arg | Arg | Arg | Cys | Phe | Cys | Thr | Arg | Pro | Cys |
|---|---|---|---|---|---|---|---|---|---|---|---|---|---|
| 65 | | | | 70 | | | | | 75 | | | | |

<210> SEQ ID NO 95
<211> LENGTH: 47
<212> TYPE: PRT
<213> ORGANISM: artificial
<220> FEATURE:
<223> OTHER INFORMATION: HXL034 Nicotiana benthamiana

<400> SEQUENCE: 95

```
Arg Arg Cys Glu Ser Lys Ser Gln Arg Phe Lys Gly Pro Cys Val Arg
1               5                   10                  15

Val Lys Asn Cys Ala Ala Val Cys Glu Thr Glu Gly Phe Ser Gly Gly
            20                  25                  30

Asp Cys Arg Gly Leu Arg Arg Arg Cys Phe Cys Thr Arg Pro Cys
        35                  40                  45
```

<210> SEQ ID NO 96
<211> LENGTH: 318
<212> TYPE: DNA
<213> ORGANISM: artificial
<220> FEATURE:
<223> OTHER INFORMATION: Nod173 Nicotiana occidentalis

<400> SEQUENCE: 96

```
atggctcgct ccttgtgctt catgggattt gctatcttgg caatgatgct ctttgttgcc      60
tatgaggtgc aagctagaca atgcaaagca gaaagcaata cattcactgg aatatgcatt     120
gccaaaccac catgcagaca agcttgtatc cgtgagaaat ttactgatgg tcattgtagc     180
aaagtcctca gaaggtgtct atgcactaag cgatgtgtgt ttgatgagaa gatgatcgaa     240
acaggagctg aaaccttagc tgaggaagca aaaacttttg ctgcagcttt gcttgaagaa     300
gagataatgg ataactga                                                   318
```

<210> SEQ ID NO 97
<211> LENGTH: 105
<212> TYPE: PRT
<213> ORGANISM: artificial
<220> FEATURE:
<223> OTHER INFORMATION: NoD173 Nicotiana occidentalis

<400> SEQUENCE: 97

```
Met Ala Arg Ser Leu Cys Phe Met Gly Phe Ala Ile Leu Ala Met Met
1               5                   10                  15

Leu Phe Val Ala Tyr Glu Val Gln Ala Arg Gln Cys Lys Ala Glu Ser
            20                  25                  30

Asn Thr Phe Thr Gly Ile Cys Ile Ala Lys Pro Pro Cys Arg Gln Ala
        35                  40                  45

Cys Ile Arg Glu Lys Phe Thr Asp Gly His Cys Ser Lys Val Leu Arg
    50                  55                  60

Arg Cys Leu Cys Thr Lys Arg Cys Val Phe Asp Glu Lys Met Ile Glu
65                  70                  75                  80

Thr Gly Ala Glu Thr Leu Ala Glu Glu Ala Lys Thr Phe Ala Ala Ala
                85                  90                  95

Leu Leu Glu Glu Glu Ile Met Asp Asn
            100                 105
```

<210> SEQ ID NO 98
<211> LENGTH: 47
<212> TYPE: PRT
<213> ORGANISM: artificial
<220> FEATURE:

```
<223> OTHER INFORMATION: NoD173 Nictoniana occidentalis

<400> SEQUENCE: 98

Arg Gln Cys Lys Ala Glu Ser Asn Thr Phe Thr Gly Ile Cys Ile Ala
1               5                   10                  15

Lys Pro Pro Cys Arg Gln Ala Cys Ile Arg Glu Lys Phe Thr Asp Gly
            20                  25                  30

His Cys Ser Lys Val Leu Arg Arg Cys Leu Cys Thr Lys Arg Cys
        35                  40                  45
```